(12) United States Patent
Barrangou et al.

(10) Patent No.: US 11,261,451 B2
(45) Date of Patent: *Mar. 1, 2022

(54) METHODS FOR SCREENING BACTERIA, ARCHAEA, ALGAE, AND YEAST USING CRISPR NUCLEIC ACIDS

(71) Applicant: North Carolina State University, Raleigh, NC (US)

(72) Inventors: Rodolphe Barrangou, Raleigh, NC (US); Kurt M. Selle, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,052

(22) Filed: Oct. 5, 2018

(65) Prior Publication Data

US 2019/0021343 A1    Jan. 24, 2019

Related U.S. Application Data

(63) Continuation of application No. 15/167,727, filed on May 27, 2016, now Pat. No. 10,136,649.

(60) Provisional application No. 62/296,853, filed on Feb. 18, 2016, provisional application No. 62/168,355, filed on May 29, 2015.

(51) Int. Cl.
| | | |
|---|---|---|
| *C12N 15/63* | (2006.01) | |
| *C12N 15/10* | (2006.01) | |
| *A01N 37/46* | (2006.01) | |
| *A01N 63/60* | (2020.01) | |

(52) U.S. Cl.
CPC .............. *C12N 15/63* (2013.01); *A01N 37/46* (2013.01); *A01N 63/60* (2020.01); *C12N 15/1034* (2013.01); *C12N 15/1079* (2013.01)

(58) Field of Classification Search
None
See application file for complete search history.

(56) References Cited

U.S. PATENT DOCUMENTS

| | | |
|---|---|---|
| 8,993,233 B2 | 3/2015 | Zhang et al. |
| 9,023,649 B2 | 5/2015 | Mali et al. |
| 9,260,723 B2 | 2/2016 | Mali et al. |
| 2006/0199190 A1 | 9/2006 | Russell et al. |
| 2009/0007301 A1 | 1/2009 | Wintz et al. |
| 2013/0288251 A1 | 10/2013 | Horvath et al. |
| 2014/0068797 A1 | 3/2014 | Doudna et al. |
| 2014/0113376 A1 | 4/2014 | Sorek et al. |
| 2014/0273233 A1 | 9/2014 | Chen et al. |
| 2014/0356867 A1 | 12/2014 | Peter et al. |
| 2014/0356956 A1 | 12/2014 | Church et al. |
| 2015/0050699 A1 | 2/2015 | Siksnys et al. |
| 2015/0056628 A1 | 2/2015 | Russell et al. |
| 2015/0064138 A1 | 3/2015 | Lu et al. |
| 2015/0093473 A1 | 4/2015 | Barrangou et al. |
| 2015/0098954 A1 | 4/2015 | Hyde et al. |
| 2015/0132263 A1 | 5/2015 | Liu et al. |
| 2015/0291961 A1 | 10/2015 | Siksnys et al. |
| 2015/0315576 A1 | 11/2015 | Caliando et al. |
| 2015/0353901 A1 | 12/2015 | Liu et al. |
| 2016/0017366 A1 | 1/2016 | Chen et al. |
| 2016/0024510 A1 | 1/2016 | Bikard et al. |
| 2016/0186152 A1 | 6/2016 | Brouns et al. |
| 2016/0186213 A1 | 6/2016 | Zhang et al. |
| 2016/0289700 A1 | 10/2016 | Barrangou et al. |
| 2016/0298096 A1 | 10/2016 | Charpentier et al. |
| 2016/0324938 A1* | 11/2016 | Bikard .................. C12N 15/74 |
| 2016/0333348 A1 | 11/2016 | Clube et al. |
| 2016/0345578 A1 | 12/2016 | Barrangou et al. |
| 2017/0002339 A1 | 1/2017 | Barrangou et al. |
| 2017/0028083 A1 | 2/2017 | Beisel et al. |
| 2017/0196225 A1 | 7/2017 | Clube et al. |
| 2017/0246221 A1 | 8/2017 | Clube et al. |
| 2017/0260546 A1* | 9/2017 | Qimron .................. C12N 15/63 |
| 2017/0275648 A1 | 9/2017 | Barrangou et al. |
| 2018/0064114 A1 | 3/2018 | Clube |
| 2018/0064115 A1 | 3/2018 | Clube et al. |
| 2018/0070594 A1 | 3/2018 | Clube et al. |
| 2018/0084785 A1 | 3/2018 | Clube |
| 2018/0084786 A1 | 3/2018 | Clube |
| 2018/0146681 A1 | 5/2018 | Clube |
| 2018/0155729 A1 | 6/2018 | Beisel et al. |
| 2018/0200387 A1 | 7/2018 | Porteus |
| 2018/0258411 A1 | 9/2018 | Kadiyala et al. |
| 2018/0273937 A1 | 9/2018 | Beisel et al. |

FOREIGN PATENT DOCUMENTS

| | | |
|---|---|---|
| EP | 286267 | 4/2015 |
| EP | 2860267 | 4/2015 |
| WO | 2006/113709 | 10/2006 |
| WO | WO 2010/054154 | 5/2010 |
| WO | WO 2010/075424 | 7/2010 |
| WO | 2013/098244 | 7/2013 |
| WO | 2013/141680 | 9/2013 |
| WO | WO 2013/141680 | 9/2013 |
| WO | 2013/176772 | 11/2013 |
| WO | WO 2013176772 | 11/2013 |
| WO | WO 2013/188638 | 12/2013 |
| WO | WO 2013188522 | 12/2013 |

(Continued)

OTHER PUBLICATIONS

Milani C et al. Genomic encyclopedia of type strains of the genus *Bifidobacterium*. Applied and Environmental Microbiology. Oct. 2014; 80(20): 6290-6302.

(Continued)

*Primary Examiner* — Channing S Mahatan
(74) *Attorney, Agent, or Firm* — Myers Bigel, P.A.

(57) ABSTRACT

This invention relates to the use of CRISPR nucleic acids to screen for essential and non-essential genes and expendable genomic islands in bacteria, archaea, algae and/or yeast, to kill bacteria, archaea, algae and/or yeast, to identify the phenotype of a gene or genes, and/or to screen for reduced genome size and/or a gene deletion in bacteria, archaea, algae and/or yeast.

12 Claims, 35 Drawing Sheets

Specification includes a Sequence Listing.

(56) References Cited

FOREIGN PATENT DOCUMENTS

| WO | 2014/022702 | 2/2014 |
|---|---|---|
| WO | WO 2014/022702 | 2/2014 |
| WO | WO 2014/071235 | 5/2014 |
| WO | WO 2014065596 | 5/2014 |
| WO | 2014/093479 | 6/2014 |
| WO | WO 2014110006 | 7/2014 |
| WO | WO 2014113493 | 7/2014 |
| WO | WO 2014/124226 | 8/2014 |
| WO | WO 2014144155 | 9/2014 |
| WO | WO 2014144592 | 9/2014 |
| WO | WO 2014150624 | 9/2014 |
| WO | WO 2014186686 | 11/2014 |
| WO | WO 2014/204727 | 12/2014 |
| WO | WO 2014191128 | 12/2014 |
| WO | WO 2014191518 | 12/2014 |
| WO | WO 2014201015 | 12/2014 |
| WO | WO 20142014727 | 12/2014 |
| WO | WO 2015021353 | 2/2015 |
| WO | WO 2015026886 | 2/2015 |
| WO | WO 2015/034872 | 3/2015 |
| WO | WO 2015035139 | 3/2015 |
| WO | WO 2015040402 | 3/2015 |
| WO | WO 2015/053995 | 4/2015 |
| WO | WO 2015/070193 | 5/2015 |
| WO | WO 2015077290 | 5/2015 |
| WO | 2015/089486 | 6/2015 |
| WO | WO 2015089277 | 6/2015 |
| WO | WO 2015089406 | 6/2015 |
| WO | 2015112896 A2 | 7/2015 |
| WO | WO 2015116686 | 8/2015 |
| WO | WO 2015119941 | 8/2015 |
| WO | WO 2015139139 | 9/2015 |
| WO | 2015/159068 | 10/2015 |
| WO | WO 2015/148680 | 10/2015 |
| WO | WO 2015/155686 | 10/2015 |
| WO | WO 2015/159086 | 10/2015 |
| WO | WO 2015/159087 | 10/2015 |
| WO | WO 2015153791 | 10/2015 |
| WO | WO 2015153889 | 10/2015 |
| WO | WO 2015153940 | 10/2015 |
| WO | WO 2015160683 | 10/2015 |
| WO | WO 2015189693 | 12/2015 |
| WO | WO 2015200555 | 12/2015 |
| WO | WO 2016/084088 | 6/2016 |
| WO | WO 2016/177682 | 11/2016 |
| WO | 2017/027423 | 2/2017 |
| WO | 2017/066497 | 4/2017 |
| WO | 2017/112620 | 6/2017 |
| WO | 2017/147507 | 8/2017 |

OTHER PUBLICATIONS

Database GenBank [online], NBI, U.S. National Library of Medicine. Aug. 5, 2014. "CRISPER-associated protein, Csn1 family [Bifidobacterium bombi DSM 19703]." XP002785852, retrieved from NCBI accession No. GenBank: KFF31259. Database accession No. KFF31259. 1 page.
Notification of Transmittal of the International Search Report and the Written Opinion of the International Searching Authority, or the Declaration, PCT/US2016/034812, dated Sep. 15, 2016, 9 pages.
Barrangou R. "CRISPR-Cas systems and RNA-guided interference", *Wiley interdisciplinary reviews, RNA* (2013) 4: pp. 267-278.
Barrangou R., et al. "CRISPR: new horizons in phage resistance and strain identification" *Annu Rev Food Sci Technol* (2012) 3, pp. 143-162.
Barrangou R., et al. "CRISPR-Cas systems: prokaryotes upgrade to adaptive immunity", *Mol Cell* (2014) 54(2): pp. 234-244.
Barrangou, R. "Diversity of CRISPR-Cas immune systems and molecular machines", *Genome Biology* (2015) 16:247, 11 pages.
Barrangou, R., et al. "CRISPR provides acquired resistance against viruses in prokaryotes", *Science* (2007) 315(5819): pp. 1709-1712.

Bhaya et al. "CRISPR-Cas Systems in Bacteria and Archaea: Versatile Small RNAs for Adaptive Defense and Regulation", *Annu. Rev. Genet.* (2011) 45: pp. 273-297.
Bikard D. et al. "Programmable repression and activation of bacterial gene expression using an engineered CRISPR-Cas system" *Nucleic Acids Res* (2013) 41(15): pp. 7429-7437.
Bikard D., et al. "CRISPR interference can prevent natural transformation and virulence acquisition during in vivo bacterial infection", *Cell Host & Microbe* (2012), 10 pages.
Bikard D., et al. "Exploiting CRISPR-Cas nucleases to produce sequence-specific antimicrobial", *Nature Biotechnology* 2014, 6 pages.
Briner et al. "Guide RNA Functional Modules Direct Cas9 Activity and Orthogonality", *Molecular Cell.* (2014) 56(2): pp. 333-339.
Brouns SJJ, et al. "Small CRISPR RNAs guide antiviral defense in prokaryotes", *Science* (2008) 321:5891, pp. 960-964.
Citorik R., et al. "Sequence-specific antimicrobials using efficiently delivered RNA-guided nucleases", *Nature Biotechnology* 2014, 7 pages.
Cong et al., "Multiplex Genome Engineering Using CRISPR/Cas Systems" *Science* (2013) vol. 339 (6121): pp. 819-823.
Darmon E, Leach DF "Bacterial Genome Instability", *Microbiol. Mol. Biol. Rev.* (2014) vol. 78, pp. 1-39.
Deltcheva, E. et al. "CRISPR RNA maturation by trans-encoded small RNA and host factor RNase III", *Nature*, vol. 471, (Mar. 2011) pp. 602-607.
Edgar R., et al. "The *Escherichia coli* CRISPR System Protects from Lysogenization, Lysogens, and Prophage Induction", *Journal of Bacteriology* (2010), vol. 192, No. 23, pp. 6292-6294.
Garneau JE, et al. "The CRISPR/Cas bacterial immune system cleaves bacteriophage and plasmid DNA" *Nature* (2010) 468(7320): pp. 67-71.
Gasiunas et al. "Cas9-crRNA ribonucleoprotein complex mediates specific DNA cleavage for adaptive immunity in bacteria", *Proc. Natl. Acad. Sci.* (2012), 109:E2579-E2586.
Gilbert, L. A. et al. "CRISPR-Mediated Modular RNA-Guided Regulation of Transcription in Eukaryotes", *Cell* 154, (2013) pp. 442-451.
Gomaa AA, et al. "Programmable Removal of Bacterial Strains by Use of Genome-Targeting CRISPR-Cas Systems", *mBio* (2014), 5(1):e00928-13.
Haurwitz et al. "Sequence- and Structure-Specific RNA Processing by a CRISPR Endonuclease", *Science* (2010) 329: pp. 1355-1358.
Horvath and Barrangou "CRISPR/Cas, the Immune System of Bacteria and Archaea", *Science* (2010) 327, pp. 167-170.
Jiang, W. et al. "Dealing with the Evolutionary Downside of CRISPR Immunity: Bacteria and Beneficial Plasmids", *PLOS Genetics* (2013) vol. 9, issue 9, 13 pages.
Jiang, W. et al. "RNA-guided editing of bacterial genomes using CRISPR-Cas systems", *Nat. Biotechnol.* (2013) vol. 31, pp. 233-239.
Jinek et al. "A Programmable Dual-RNA-Guided DNA Endonuclease in Adaptive Bacterial Immunity", *Science* (2012) vol. 337, pp. 816-821.
Jinek, M. et al.,"Structures of Cas9 endonucleases reveal RNA-mediated conformational activation", *Science* (2014) vol. 343, 6176, 28 pages.
Karvelis et al. "crRNA and tracrRNA guide Cas9-mediated DNA interference in *Streptococcus* thermophilus", *RNA Biol.* (2013) vol. 10: pp. 841-851.
Kobayashi K, et al. "Essential Bacillus subtilis genes", *Proc. Natl. Acad. Sci. U.S.A.* (2003) vol. 100, pp. 4678-4683.
Labrie SJ et al. "Bacteriophage resistance mechanisms" *Nat. Rev. Microbiol* (2010) vol. 8, pp. 317-327.
Luo, M. et al., "Repurposing endogenous type I CRISPR-Cas systems for programmable gene repression", *Nucleic Acid Research* (2014) 8 pages.
Magadan et al. "Cleavage of Phage DNA by the *Streptococcus* thermophilus CRISPR3-Cas System", *PLoS One* (2012) 7:e40913. 8 pages.
Mahillon J. et al. "Insertion sequences", *Microbiol Mol Biol Rev* (1998) vol. 62(3): pp. 725-774.

(56) References Cited

OTHER PUBLICATIONS

Makarova and Koonin "Annotation and Classification of CRISPR-Cas Systems", *Methods Mol Biol.* (2015), 1311: pp. 47-75.

Makarova et al. "An updated evolutionary classification of CRISPR-Cas systems", *Nat Rev Microbiol.* 13:722-736 (2015), 15 pages.

Makarova et al. "Unification of Cas protein families and a simple scenario for the origin and evolution of CRISPRCas systems", *Biol Direct.* (2011) vol. 6:38, 27 pages.

Makarova, K. S et al. "Evolution and classification of the CRISPR-Cas systems", *Nat Rev Microbiol* (2011) vol. 9, pp. 467-477.

Marraffini and Sontheimer "CRISPR Interference Limits Horizontal Gene Transfer in *Staphylococci* by Targeting DNA", *Science* (2008) vol. 322: pp. 1843-1845.

Mojica, F. et al. "Short motif sequences determine the targets of the prokaryotic CRISPR defence system", *Microbiology* (2009) vol. 155, 8 pages.

Nishimasu, H., et al. "Crystal Structure of Cas9 in Complex with Guide RNA and Target DNA", *Cell* (2014) vol. 156, pp. 935-949.

Oh JH and van Pijkeren JP "CRISPR-Cas9-assisted recombineering in Lactobacillus reuteri", *Nucleic Acids Res* (2014) vol. 10.1093/nar/gku623.

Qi, L. S. et al. "Repurposing CRISPR as an RNA-Guided Platform for Sequence-Specific Control of Gene Expression", *Cell* 152, 1173-1183 (2013), 11 pages.

Sander JD, and Joung JK. "CRISPR-Cas systems for editing, regulating and targeting genomes", *Nat. Biotechnol.* (2014) vol. 32, pp. 347-355.

Sapranauskas et al. "The *Streptococcus* thermophilus CRISPR/Cas system provides immunity in *Escherichia coli*", *Nucleic Acid Res.* (2011) vol. 39: pp. 9275-9282.

Selle K, Barrangou R. "Harnessing CRISPR-Cas systems for bacterial genome editing", *Cell Press: Trends Microbiol.* (2015) vol. 23(4): pp. 225-32.

Selle, K. et al. "CRISPR-based screening of genomic island excision events in bacteria", *Proc Natl Acad Sci USA*, (2015); 112(26): pp. 8076-8081.

Selle, K. et al., "CRISPR-Based Technologies and the Future of Food Science", *Journal of Food Science* (2015) vol. 80, 6 pages.

Sinkuna, T. et al. "In vitro reconstitution of Cascade-mediated CRISPR immunity in *Streptococcus* thermophilus", *The EMBO Journal* (2013) vol. 32, pp. 385-394.

Stern, A. et al., "Self-targeting by CRISPR: gene regulation or autoimmunity?", *Cell Press: Trends in Genetics*, (2010) vol. 26, No. 8, 6 pages.

Terns and Terns "CRISPR-based adaptive immune systems", *Curr. Opin. Microbiol.* (2011) vol. 14: pp. 321-327.

Vercoe RB, et al. "Cytotoxic chromosomal targeting by CRISPR/Cas systems can reshape bacterial genomes and expel or remodel pathogenicity islands", *PLoS Genet* (2013) vol. 9(4):e1003454.

Westra et al. "The CRISPRs, They Are A-Changin': How Prokaryotes Generate Adaptive Immunity", *Annu. Rev. Genet.* (2012) vol. 46: pp. 311-339.

Tautvydas Karvelis et al., "crRNA and tracerRNK guide Cas9-mediated DNA interference in *Streptococcus* themophilas," RNA Biology, 2013, vol. 10, Issue 5, pp. 841-851.

Karvelis Tautvydas et al., "Programmable DNA cleavage in vitro by Cas9," Biochem. Soc. Trans. 2013. vol. 41, part 6, pp. 1401-1406.

International Search Report and Written Opinion for PCT/US2015/047136 dated Nov. 26, 2015, 10 pages.

Briner AE, Bartangou R. "LactoPaclRjs. buchneri Genotyping on the Basis of Clustered Regularly Interspaced Short Palindromic Repeat (CRISPR) Locus Diversity", *Appl Environ Microbiol.* 80:994-1001, (2014).

Carte et al. "The three major types of CRISPR-Cas systems function independently in CRISPR RNA biogenesis in *Streptococcus* thermophilus", *Molecular Microbiology*, 93(1), pp. 98-112 (2014).

Chylinski et al. "Classification and evolution of type II CRISPR-Cas Systems", *Nucleic Acids Research*, (2014) 15 pages.

Chylinski Krzysztof et al., "The tracrRNA and Cas9 families of type II CRISPR-Cas immunity systems", *RNA biology*, 10:5, 13 pages (2013).

Doench et al. "Rational design of highly active sgRNAs for CRISPR-Cas9-mediated gene inactivation", *Nature Biotechnology*, 32:12 (2014) 8 pages.

Dupuis ME et al., "CRISPR-Cas and restriction-modification systems are compatible and increase phage resistance", *Nat Commun.*, vol. 4, p. 2087 (2013).

Estvelt et al. "Orthogonal Cas9 proteins for RNA-guided gene regulaton and editing", *Nature Methods*, 10:11 (2013) pp. 1116-1121.

Fonfara, I. et al. "Phylogeny of Cas9 determines functional exchangeability of dual-RNA and Cas9 among orthologous type II CRISPR-Cas systems", *Nucleic Acids Res* (2013) 14 pages.

Fu et al. "Improving CRISPR-Cas nuclease specificity using truncated guide RNAs", *Nature Biotechnology*, 32:3: (2013) 9 pages.

Gilbert et al. "Genome-Scale CRISPR-Mediated Control of Gene Repression and Activation", *Cell* 159 (2014) pp. 647-661.

Hsu et al. "DNA targeting specificity of RNA-guided Cas9 nucleases", *Nature Biotechnology*, 31:9 (2013) pp. 827-834.

Notification of International Preliminary Report on Patentability corresponding to International Application No. PCT/IB2015/052515; dated Oct. 12, 2016, 7 pages.

Notification and Transmittal of International Search Report and Written Opinion of the International Searching Authority for International Application No. PCT/IB2015/052615; dated Oct. 10, 2015; 12 pages.

Novagen "pCDF-1b Vector" Sep. 10, 2003, Retrieved from the Internet on Sep. 1, 2015, at http://www.helmholtz-muenchen.de/fieadmin/PEPF/pCDF_vectors/pCDF-1b_map.pdf, 2 pages.

Seed Kimberley D. et al., "A bacteriophage encodes its own CRISPR/Cas adaptive response to evade host innate immunity", *Nature*, 494:7438, pp. 489-491 (2013).

Semenova et al. "Interference by clustered regularly interspaced short palindromic repeat: (CRISPR) RNA is governed by a seed sequence", *PNAS*, 108:25 (2011) 6 pages.

Sternberg et al. "DNA interrogation by the CRISPR RNA-guided endonuclease Cas9", *Nature*, vol. 507, (2014) 17 pages.

Wiedenheft et al. "RNA-guided complex from a bacterial immune system enhances target recognition through seed sequence interactions", *PNAS*, 108:36 (2011) 7 pages.

Written Opinion and International Search Report corresponding to International Application No. PCT/US2016/037493, dated Sep. 15, 2016, 8 pages.

Citorik RJ. et al, "Sequence-specific antimicrobials using efficiently delivered RNA-guiding nucleases Supplemental Material," Nature Biotechnology, Sep. 21, 2014; 32(11): 1141-1145. DOI:10.1038/nbt.3011, 14 pages.

Beisel CL et al. A CRISPR design for next-generation antimicrobials. Genome Biology. 2014; 15: 516, 4 pages.

Ramakrishna Suresh et al. "Gene disruption by cell-penetrating peptide-mediated delivery of Cas9 protein and guide RNA", Genome Research, 24:1020-1027 (2014).

Hainl, Stefan et al., "Insights into the completely annotated genome of Lactobacillus buchneri CD034, a strain isolated from stable grass silage", Journal of Biotechnology, 161:153-166 (2012).

Marcotte, H. et al, "Proteomes—Lactobacillus gasseri DSM 14869", NCBI Reference Sequence CP006803, (2013) URL: https://www.uniprot.org/proteomes/UP00217220, retrieved Jul. 20, 2018.

Ajdic et al. "hypothetical protein SMU_1405c [*Streptococcus* mutans UA159]", Proc. Natl. Acad. Sci. U.S.A. 99 (22), 14434-14439 (2002) URL: https://www.nobl.nlm.nlh.gov/protein/NP_721764.1/, retrieved Jul. 20, 2018.

Cochrane Kyla et al., "Complete genome sequences and analysis of the Fusobacterium nucleatum subspecies *animalis* 7-1. bacteriophage PHIFunu 1 and PHIFunu2", Anaerobe, 38:125-129 (2016).

Nale Janet Y. et al., "Diverse temperate bacteriophage carriage in Clostridium difficile 027 strains", PLoS One, 7(5) 1-9 (2012).

Uchiyama Jumpei et al., "Characterization of Helicobacter pylori bacteriophage KHP30", Applied and environmental microbiology, 79(10):3176-3184 (2013).

(56) References Cited

OTHER PUBLICATIONS

Written Opinion of the International Search Report regarding International Application No. PCT/US2016/067657, dated Mar. 6, 2017, 9 pages.
Claesson et al. NCBI reference sequence NC_007929, direct submission Dec. 16, 2005, p. 1 (2005).
Cong et al. Supplementary Materials for "Multiplex Genome Engineering Using CRISPR/Cas Systems" Science (2013) vol. 339 (6121): pp. 819-823.
Grissa et al. "The CRISPRdb database and tools to display CRISPRs and to generate dictionaries of spacers and repeats" BMC Bioinformatics, 8(172):1-10 (2007).
Spath et al. "Lactobacillus plantarum and Lactobacillus buchneri as Expression Systems: Evaluation of Different Origins of Replication for the Design of Suitable Shuttle Vectors" Mol. Biotechnol., 52:40-48 (2012).
Rath et al. "The CRISPR-Cas immune system: Biology, mechanisms and applications" Biochimie, 117:119-128 (2015).
Beloglazova et al. "Structure and activity of the Cas3 HD nuclease MJ0384, an effector enzyme of the CRISPR Interference" The EMBO Journal, 30(22):4616-4627 (2011).
Edgar et al. Supplemental Material "The *Escherichia coli* CRISPR System Protects from Lysogenization, Lysogens, and Prophage Induction" Journal of Bacteriology, 192(23): 6292-6294 2010.
Shinkai "Structure and Function of CRISPR-Cas System" Seibutsu Butsuri, 54(5):247-252 (2014) Abstract Only.
Extended European Search Report regarding European Application No. EP19196063, dated Jun. 26, 2020 12 pages.
Third Party Observations corresponding to European Patent Application No. 16804164.8, dated Jul. 24, 2019 60 pages.
Third Party Observations corresponding to European Patent Application No. 16812275.2, dated May 15, 2020 108 pages.
International Preliminary Report on Patentability Notification, PCT/US2018/034322, dated Dec. 5, 2019, 7 pages.
Anderson et al. "Lactobacillus gasseri CRISPR-Cas9 characterization In Vitro reveals a flexible mode of protospacer-adjacent motif recognition" PLOS ONE, 13(2) 14 pages 2018.
Gasiunas et al. "Molecular mechanisms of CRISPR-mediated microbial immunity" Cellular and Molecular Life Sciences, 71:449-465 (2014).
GenBank Accession No. FN692037.1, "Lactobacillus crispatus ST1 complete genome, strain ST1" Feb. 27, 2015.
Hidalgo-Cantabrana et al. "Genome editing using the endogenous type I CRISPR-Cas system in Lactobacillus crispatus" PNAS, 116)32):15774-15783 (2019).
International Search Report and Written Opinion corresponding to PCT/US2019/52883, dated Dec. 23, 2019, 9 pages.
International Search Report and Written Opinion corresponding to PCT/US2019/52878, dated Dec. 27, 2019, 14 pages.
International Search Report and Written Opinion corresponding to PCT/US2019/52864, dated Dec. 17, 2019, 15 pages.
International Search Report and Written Opinion corresponding to PCT/US2019/52861, dated Feb. 12, 2020, 18 pages.
Ojala et al. "Comparative genomics of Lactobacillus crispatus suggests novel mechanisms for the competitive exclusion of Garnerella vaginalis" BNC Genomics, 15:1070 (2014).
Sanozky-Dawes et al. "Occurrence and activity of a type II CRISPR-Cas system in Lactobacillus gasseri" Microbiology, 161:1752-1761 2015.
Westra et al. "CRISPR Immunity Relies on the Consecutive Binding and Degradation of Negatively Supercoiled Invader DNA by Cascade and Cas3" Molecular Cell, 46:595-605 (2012).
Yosef et al. "High-temperature protein G is essential for activity of the *Escherichia coli* clustered regularly interspaced short palindromic repeats (CRISPR)/Cas system" Proc Natl Acad Sci, 108(50):20136-20141 (2011).
Boudry et al. "Function of CRISPR-Cas System of the Human Pathogen Clostridium difficile" mBio, 6(5):1-15 2015.
Skennerton et al. "Phage Encoded H-NS: A Potential Achilles Heel in the Bacterial Defence System" PLoS ONE, 6(5) 7 pages 2011.
Takeda et al. "Distribution of Genes Encoding Nucleoid-Associated Protein Homologs in Plasmids" International Journal of Evolutionary Biology, 30 pages 2011.
Vega et al. "Collective Antibiotic Resistance: Mechanisms and Implications" Curr Opin Microbiol., 21:28-34 2014.
Final Office Action, U.S. Appl. No. 15/113,656, dated Jul. 30, 2018, 8 pages.
Final Office Action, U.S. Appl. No. 15/302,655, dated Nov. 2, 2018, 21 pp.
International Search Report and Written Opinion, PCT/US2018/034322, dated Sep. 13, 2018. 7 pages.
Liu S et al. Complete genome sequence of Lactobacillus buchneri NRRL B-30929, a novel strain from a commercial ethanol plant. Journal of Bacteriology. Aug. 2011; 194(15): 4019-4020.
Liu S et al. NCBI (2011) CRISPR-associated protein, Csn1 family [Lactobacillus buchneri], pp. 1-3.
Chauthaiwale, V. M. et al. "Bacteriophage Lamda as a Cloning Vector" Microbiological Reviews, 56(4):577-591 (1992).
Dang, Y. et al. "Optimizing sgRNA structure to improve CRISPR-Cas9 knockout efficiency" Genome Biology, 16(280):1-10 (2015).
Edgar, R. et al. "Reversing Bacterial Resistance to Antibiotics by Phage-Mediated Delivery of Dominant Sensitive Genes" Applied and Environmental Microbiology, 78(3):744-751 (2011).
Extended European Search Report corresponding to European Patent Application No. 18806333.3 (8 pages) (dated Feb. 9, 2021).
Third Party Observation filed in European Patent Application No. 16804164.8 on Feb. 19, 2021, 15 pages.
Third Party Observation filed in European Patent Application No. 16812275.2 on Feb. 19, 2021, 38 pages.
Yosef, I. et al. "Temperate and lytic bacteriophages programmed to sensitize and kill antibiotic-resistant bacteria" PNAS, 112(23):7267-7272 (2015).
Luo et al. "The CRISPR RNA-guided surveillance complex in *Escherichia coli* accommodates extended RNA Spacers" Nucleic Acids Research, 44(15):7385-7394 2016.
Gutierrez et al. "Predicting CRISPR-Cas9 activity in *E. coli*" bioRxviv, https://doi.org/10.1101/308148, pp. 1-22 2018.
Hochstrassera et al. "CasA mediates Cas3-catalyzed target degradation during CRISPR RNA-guided interference" PNAS, 111(18):6618-23 2014.
Nizet et al. "Bacterial sepsis and meningitis" Remington and Klein's Infectious diseases of the fetus and newborn infant, 8th Edition, pp. 217-271 2011.
Verco et al. "Cytotoxic Chromosomal Targeting by CRISPR/Cas Systems Can Reshape Bacterial Genomes and Expel or Remodel Pathogenicity Islands" PLOS Genetics, 9(4):1-13 2013.

* cited by examiner

Fig. 1

CRISPR1

LacZ: GTTTTTGTACTCTCAAGATTTAAGTAACTGTACAAC AATCCCCATAGCAGAACAATATAGTTGTT TTTTTTGTACTCTCAAGATTTAAGTAACTGTACAAAC

Spacer / Repeat

CRISPR335

Repeat / Spacer / Repeat

LacZ: GTTTTAGAGCTGTGTTGTTTCGAATGGTTCCAAAAC AGTATTTTTGAATCTCTTGAAGAATTTTCTGA GTTTTAGAGCTGTGTTGTTTCGAATGGTTCCAAAAC

ABC: GTTTTAGAGCTGTGTTGTTTCGAATGGTTCCAAAAC GATAACACGAGATAAAACATCCAGCCCACC GTTTTAGAGCTGTGTTGTTTCGAATGGTTCCAAAAC prtS: GTTTTAGAGCTGTGTTGTTTCGAATGGTTCCAAAAC GTTGTAGCTTTGAGGTCTGAGAATACACGC GTTTTAGAGCTGTGTTGTTTCGAATGGTTCCAAAAC Cu: GTTTTAGAGCTGTGTTGTTTCGAATGGTTCCAAAAC GATTGCTCAATCAATCGTTTCAGCTGCTAA GTTTTAGAGCTGTGTTGTTTCGAATGGTTCCAAAAC Fig. 5A IS1191
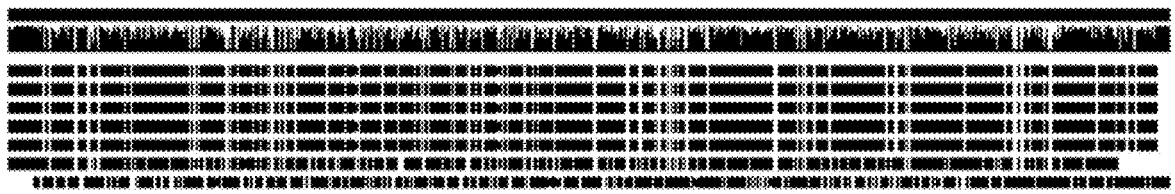
Fig. 5B Sth6
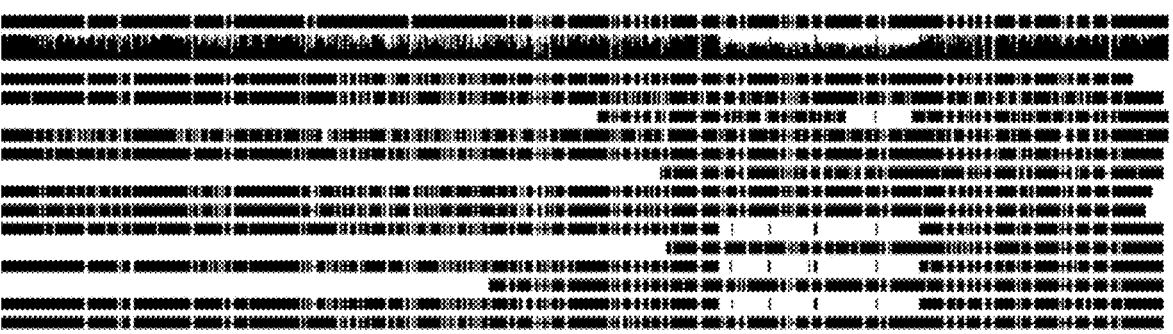
Fig. 5C IS1193
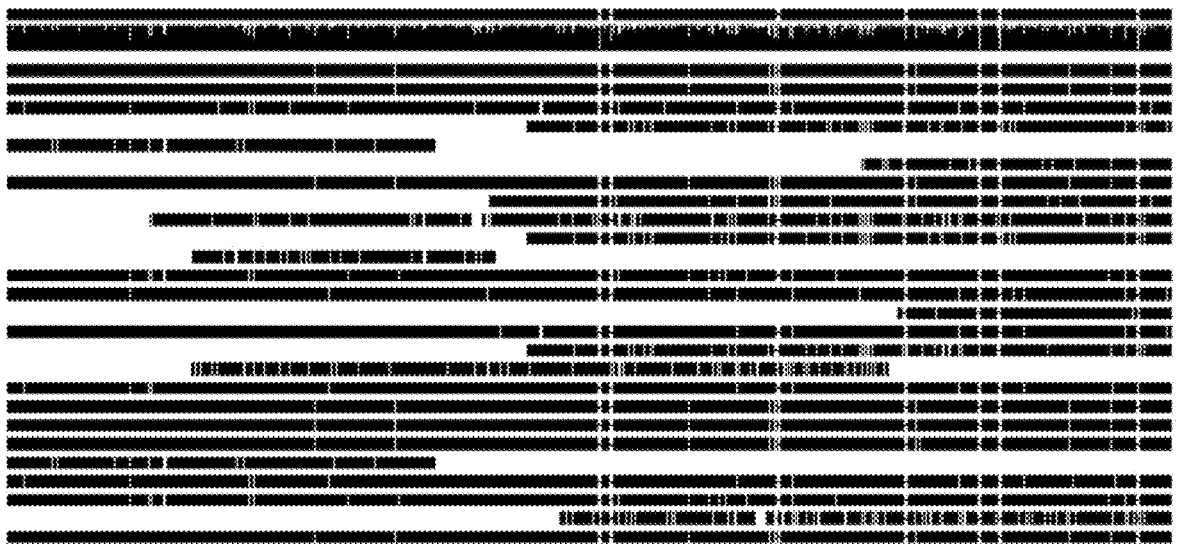
Fig. 5D IS1167
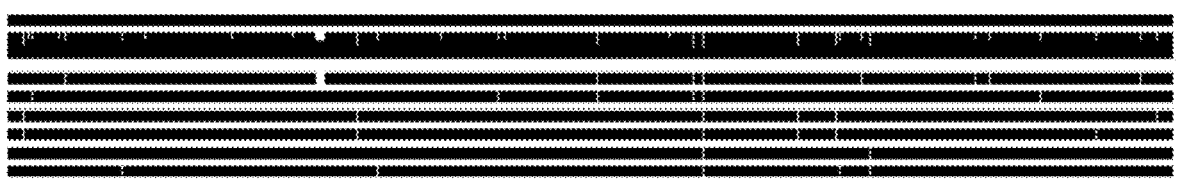

Fig. 7B
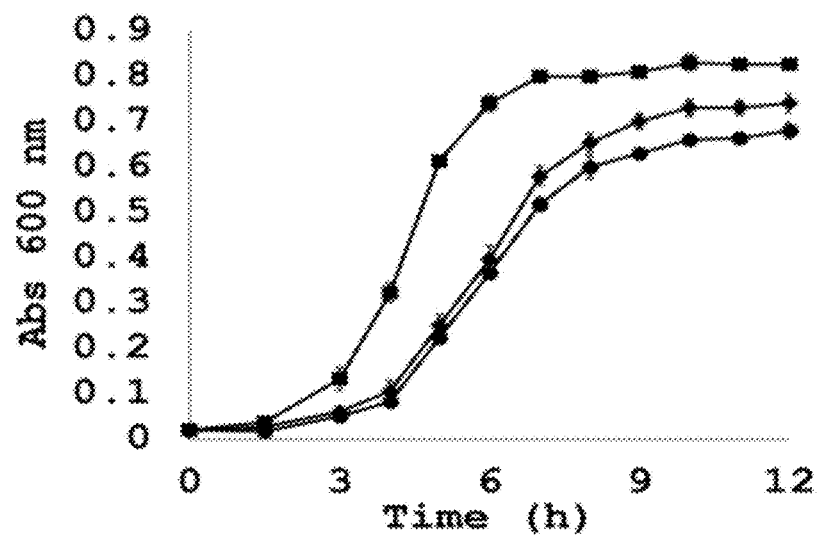
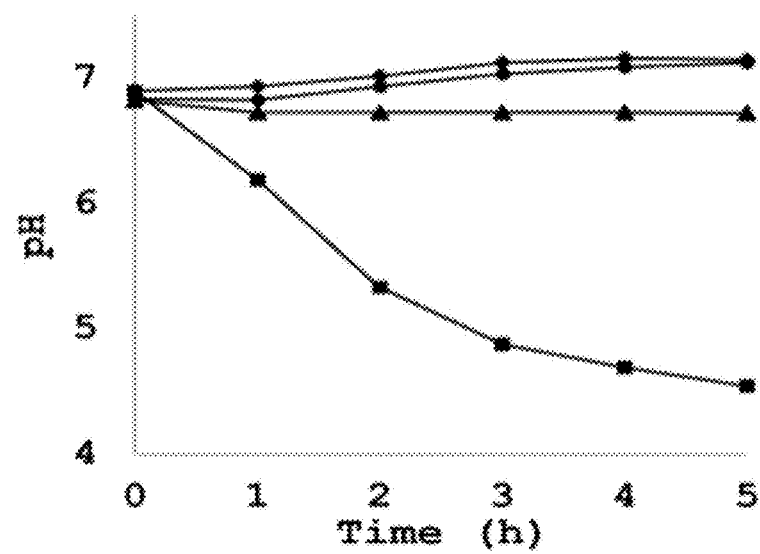

Fig. 13
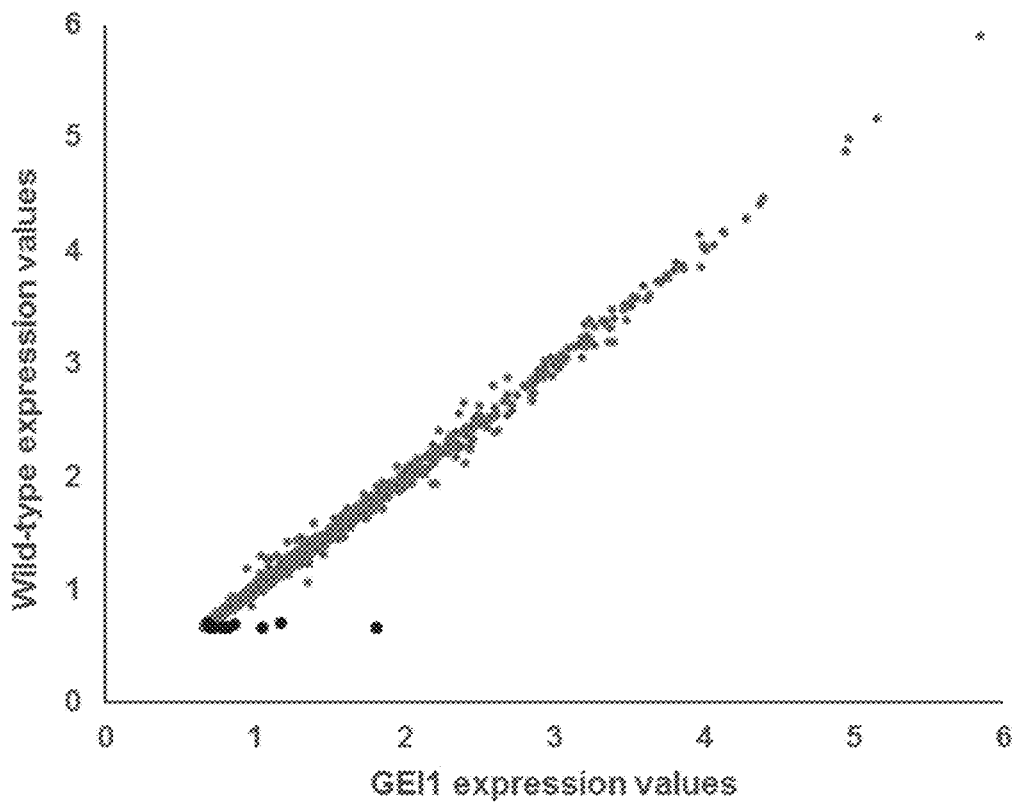
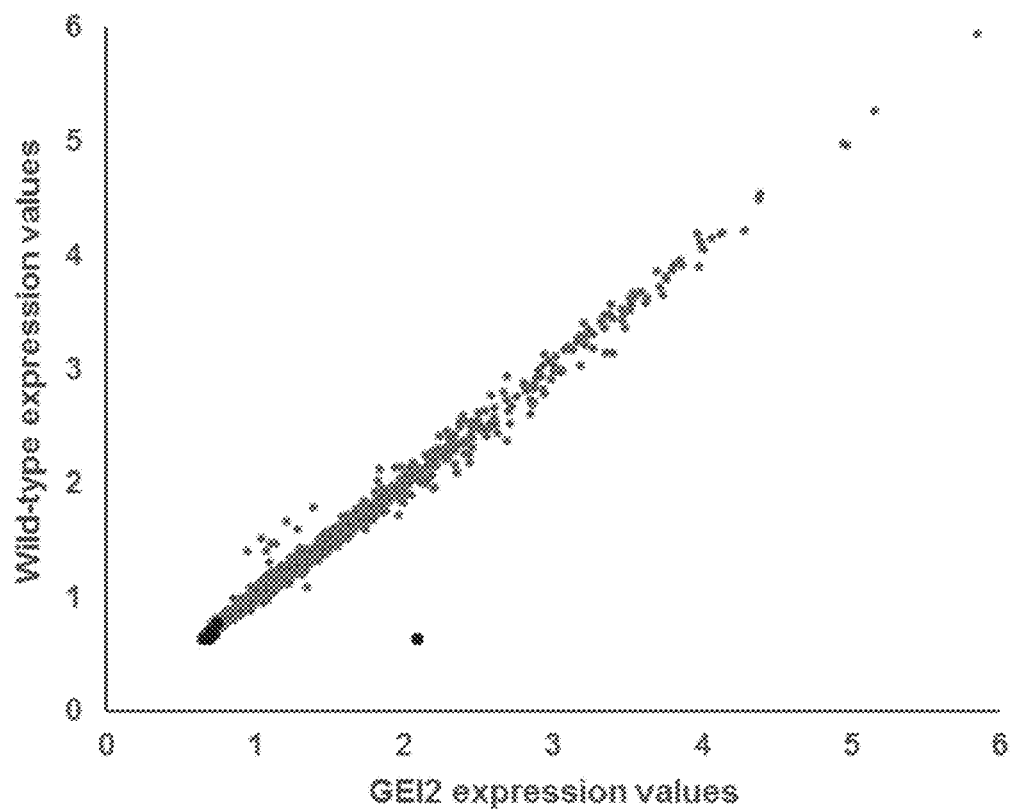

Fig. 13, cont'd.
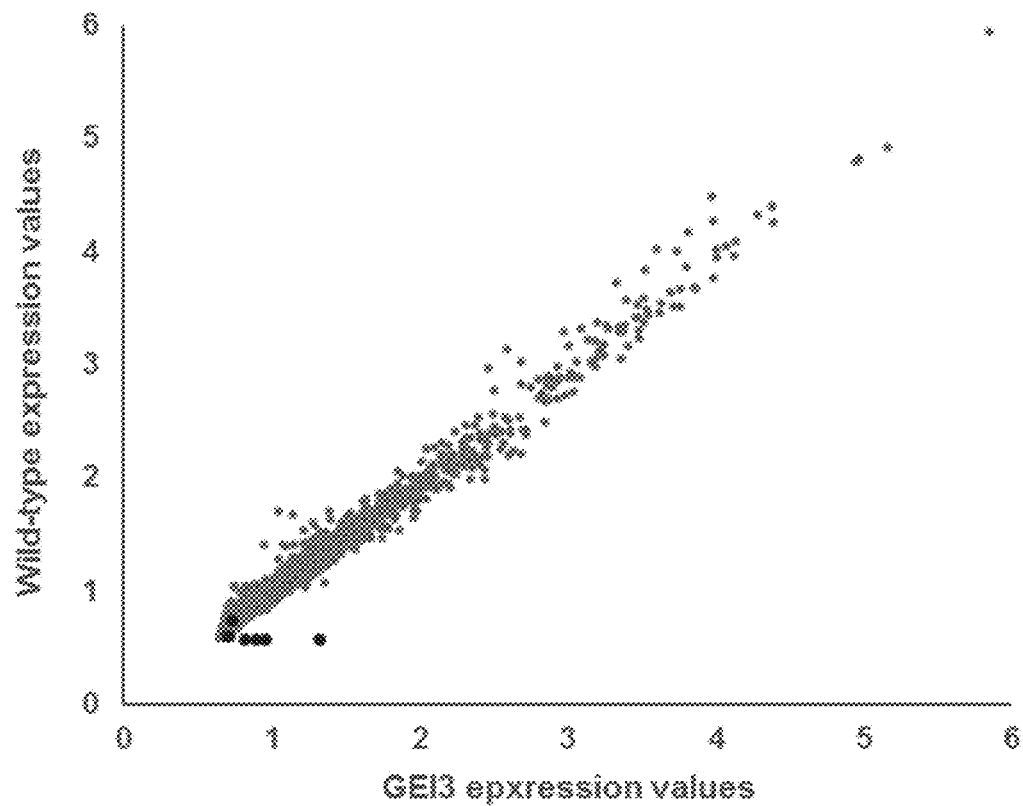
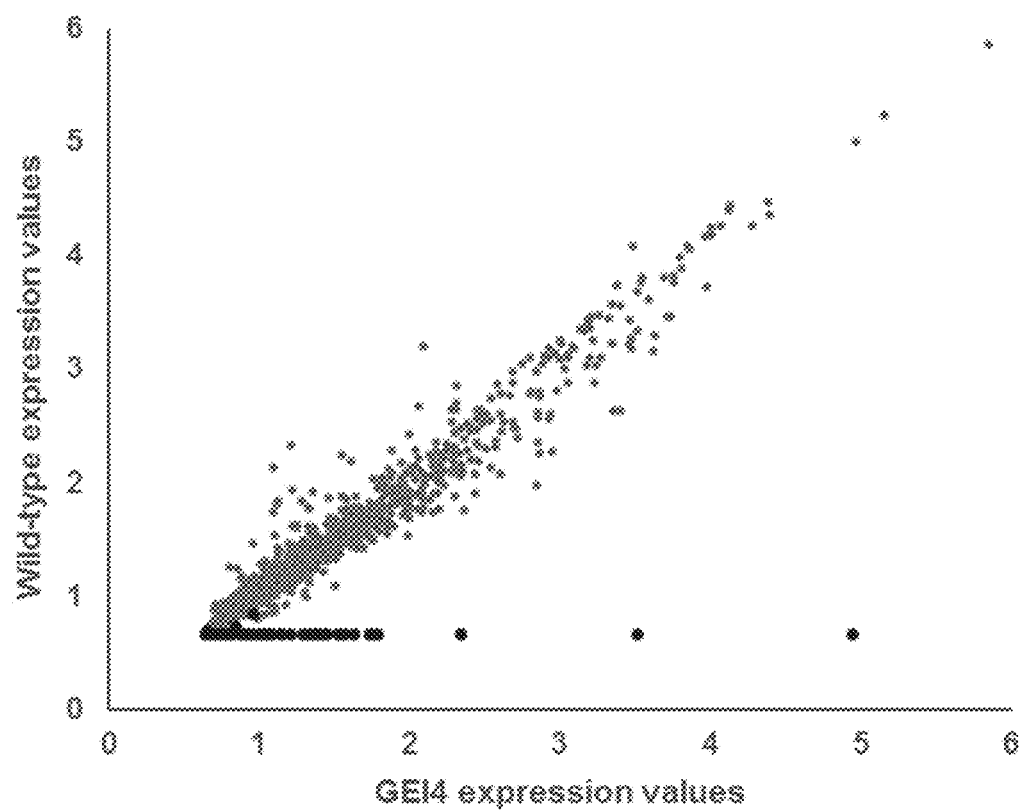

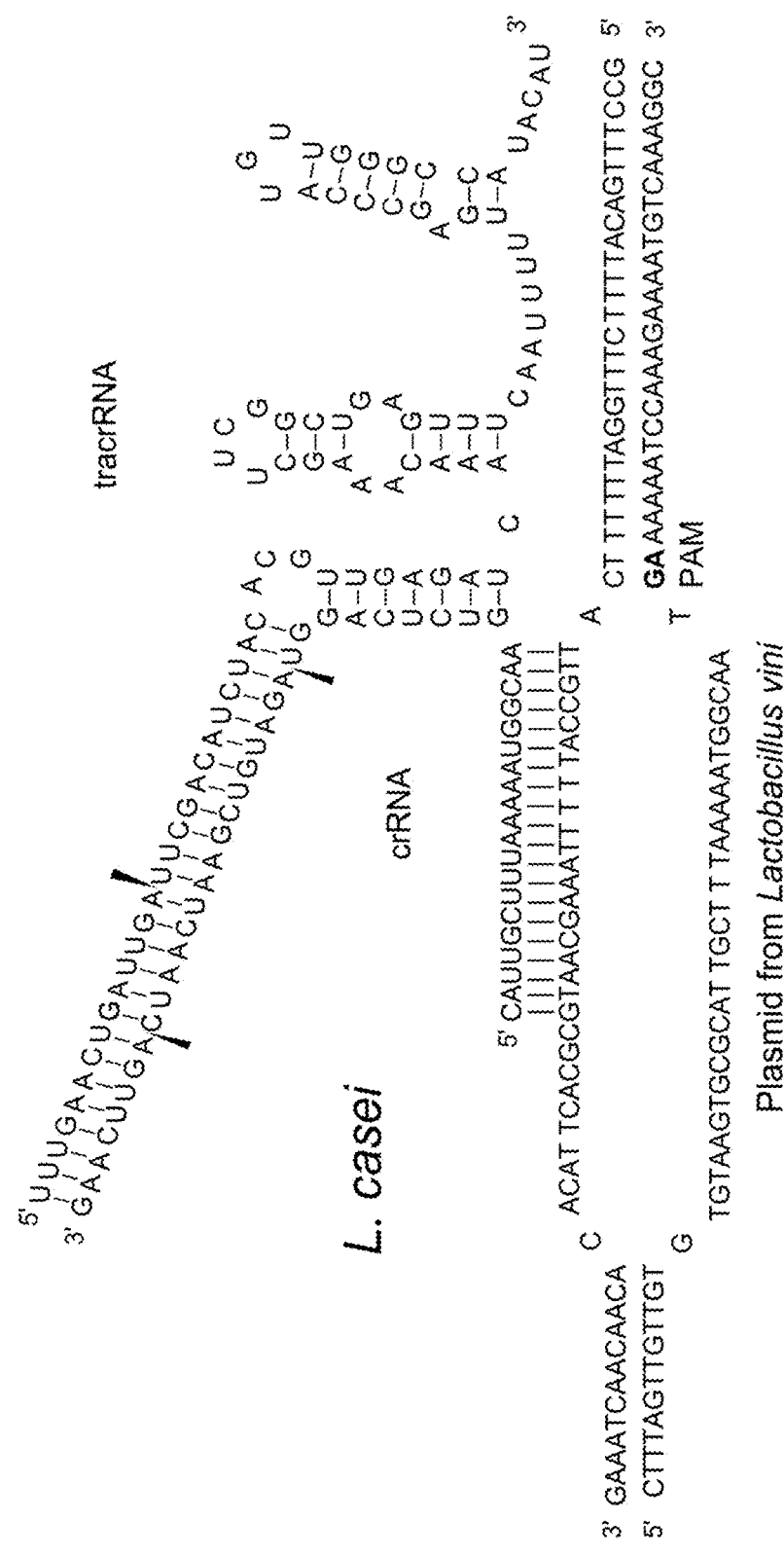
Fig. 15, cont'd.

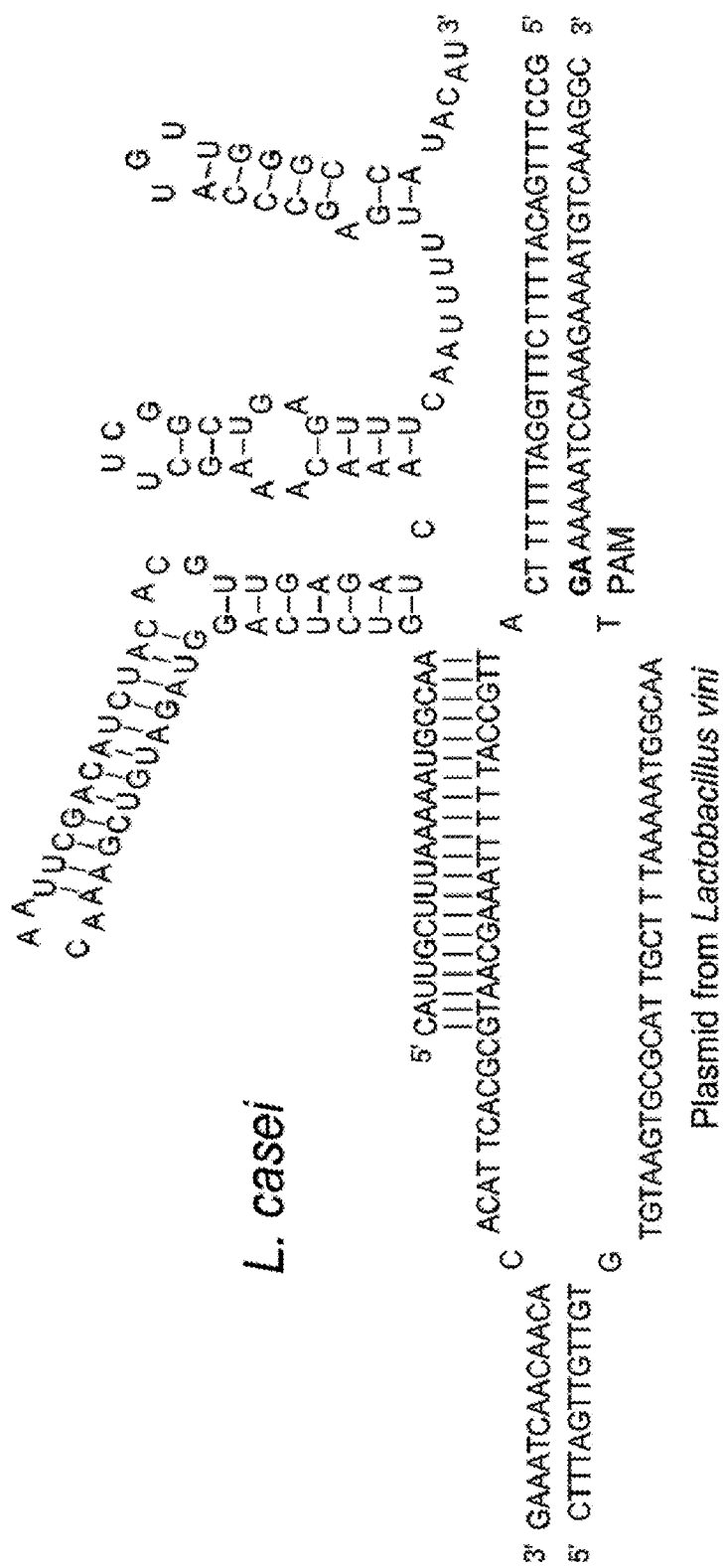
Fig. 15, cont'd.

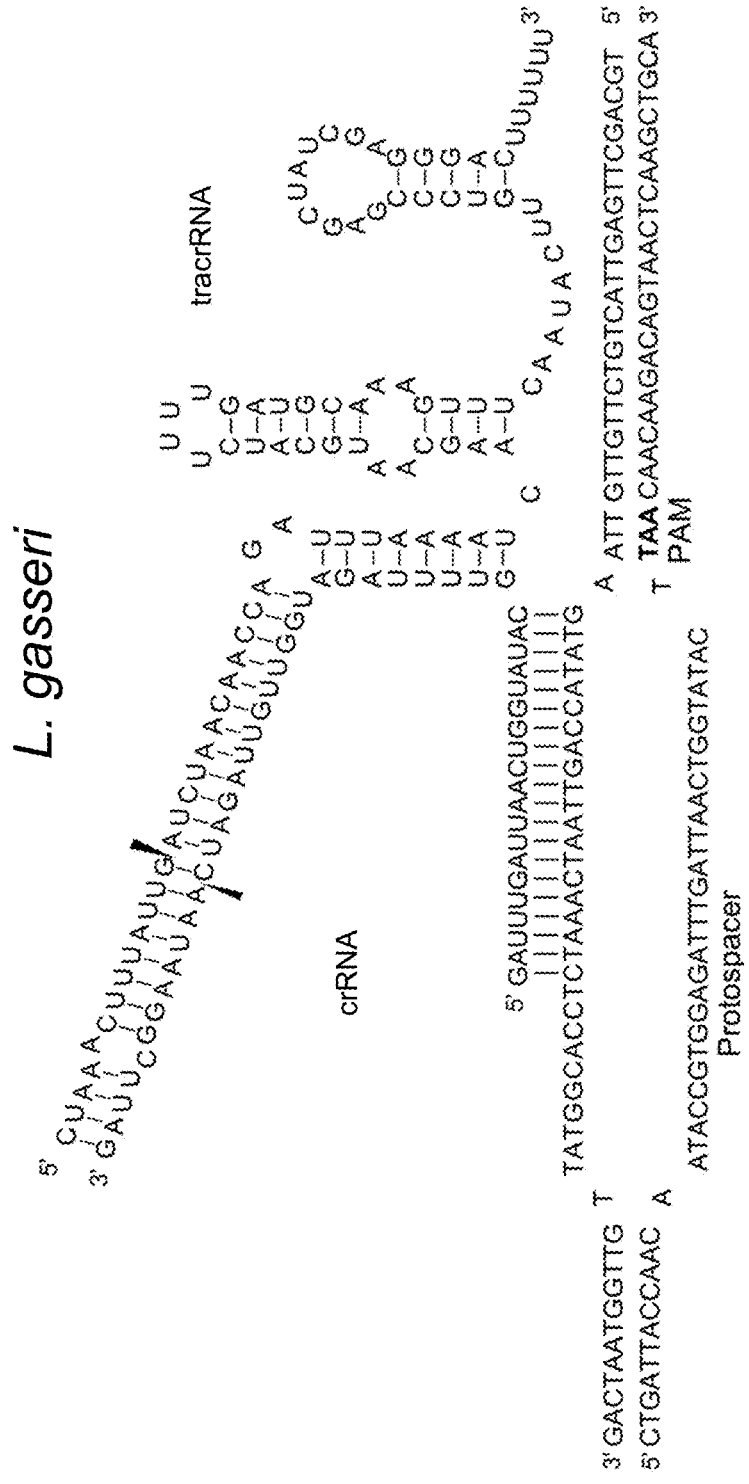
Fig. 16, cont'd.

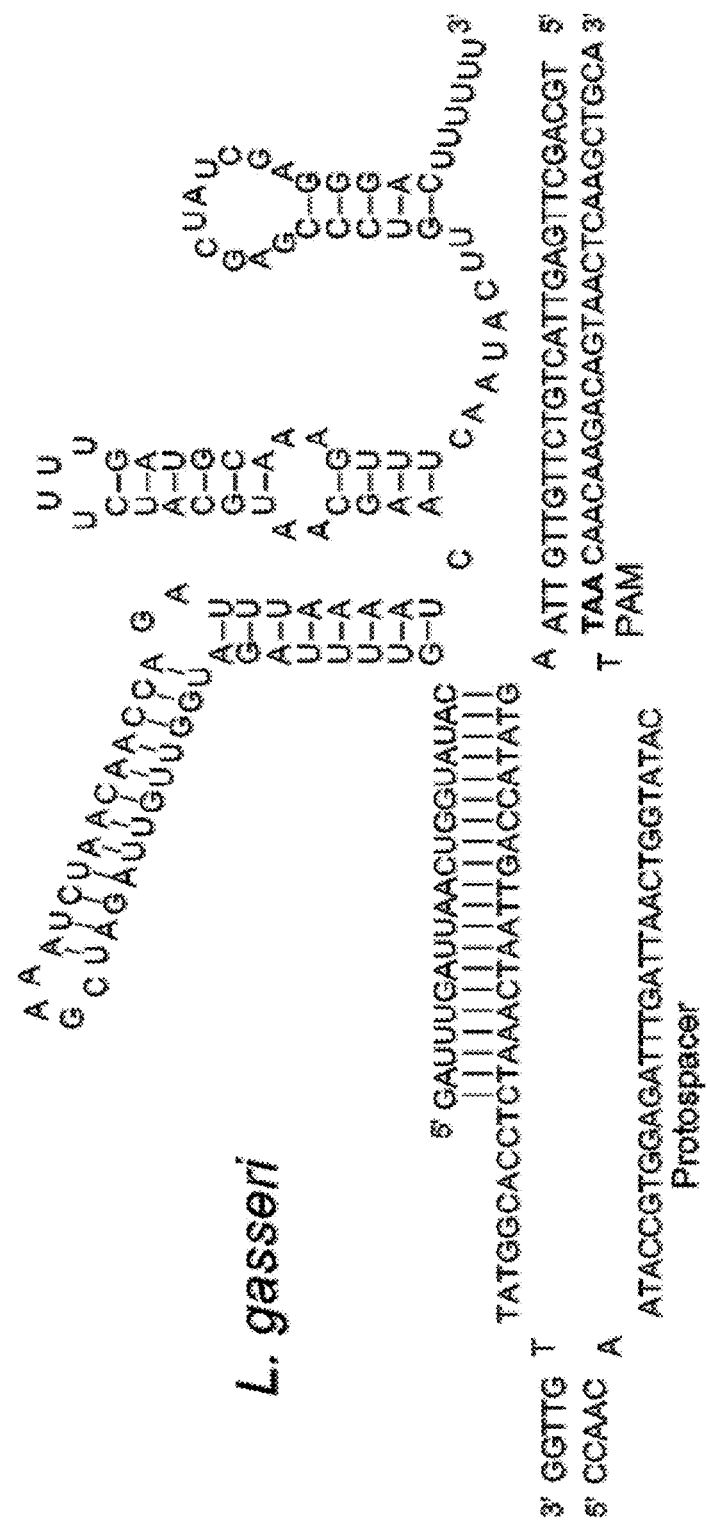
Fig. 16, cont'd.

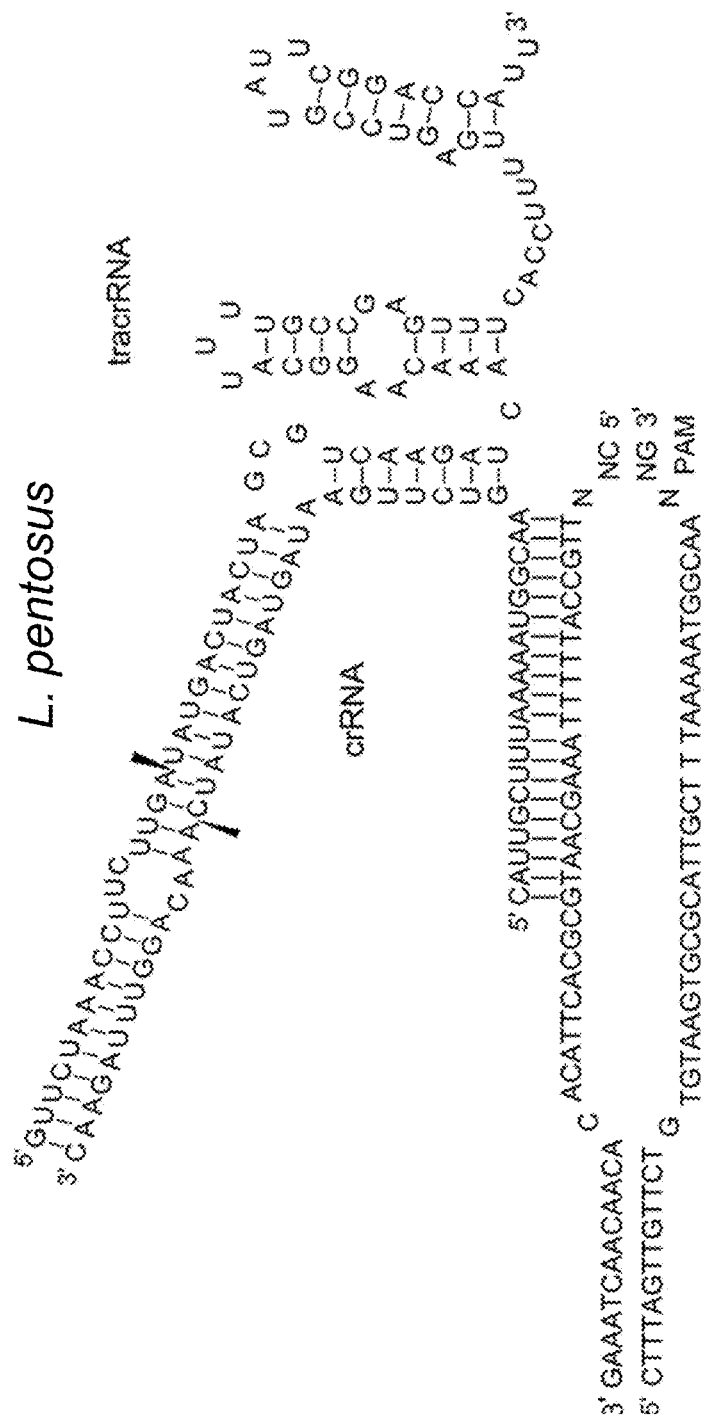
Fig. 17, cont'd.

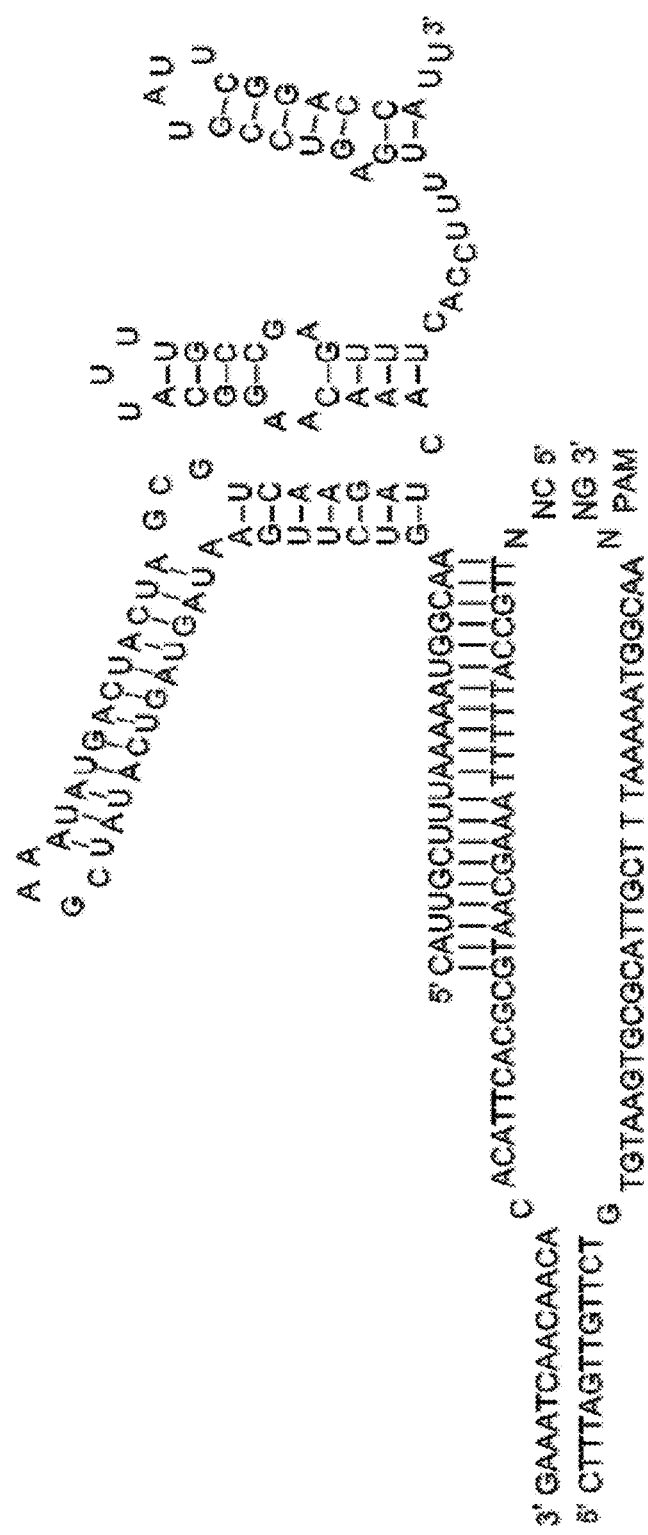
Fig. 17, cont'd.

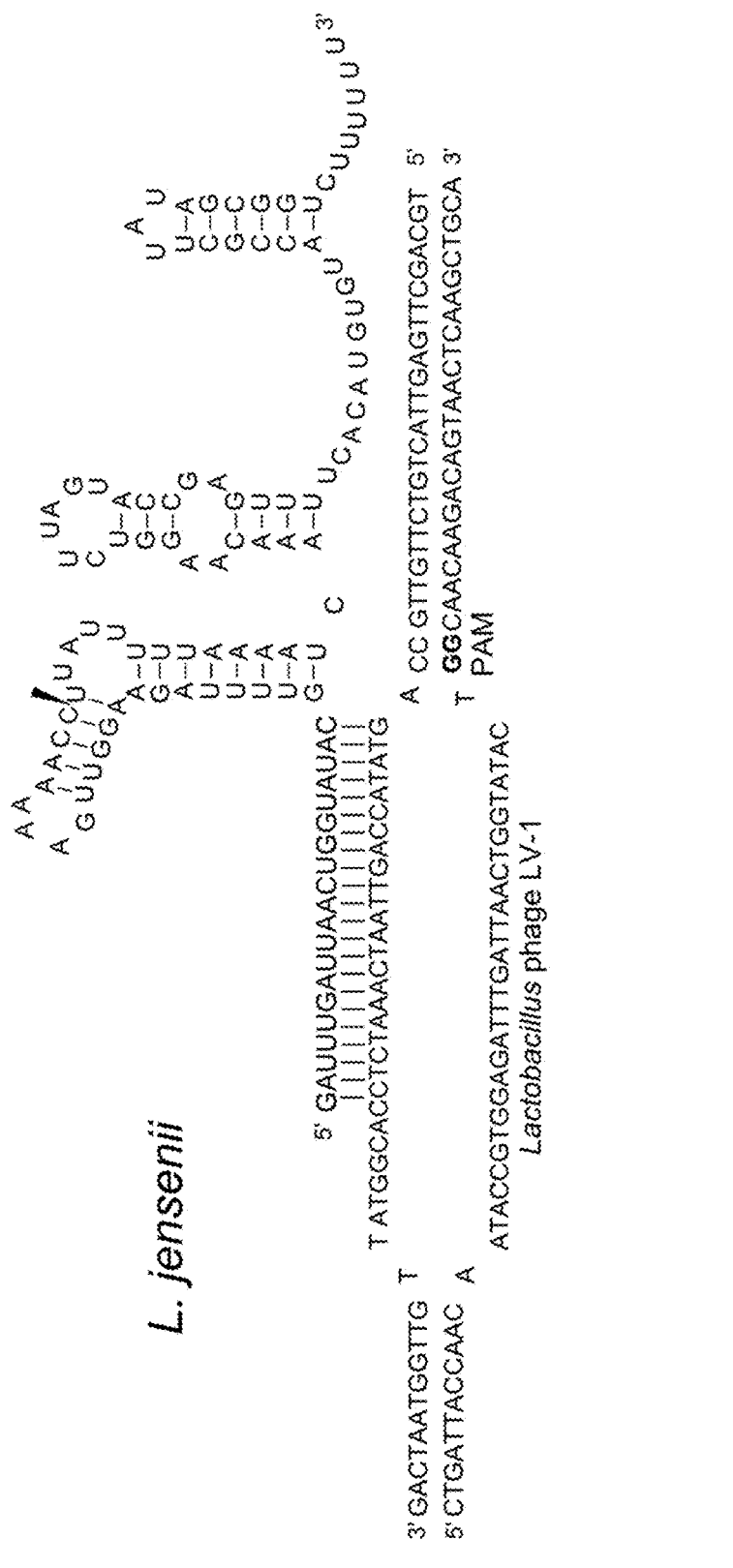
Fig. 18, cont'd.

Fig. 21

Type I LEADER

ATGGGATAGGGATTTTTTAGT

GTTTTCCCCGCACATGCGGGGGTGATCC GGCGATGATATACGTAGCCGAACTGAGAGGTTGAT GTTTTCCCCGCACATGCGGGGGTGATCC

REPEAT SPCR 1 REPEAT

METHODS FOR SCREENING BACTERIA, ARCHAEA, ALGAE, AND YEAST USING CRISPR NUCLEIC ACIDS

STATEMENT OF PRIORITY

This application is a continuation application of U.S. patent application Ser. No. 15/167,727, filed on May 27, 2016, which claims the benefit, under 35 U.S.C. § 119(e), of U.S. Provisional Application No. 62/168,355 filed on May 29, 2015, and U.S. Provisional Application No. 62/296,853, filed on Feb. 18, 2016, the entire contents of each of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 5051-881v2_ST25.txt, 16,589 bytes in size, generated on Oct. 3, 2018 and filed via EFS-Web, is provided in lieu of a paper copy. This Sequence Listing is incorporated by reference into the specification for its disclosures.

FIELD OF THE INVENTION

The invention relates to the use of CRISPR nucleic acids to screen for essential and non-essential genes and expendable genomic islands in bacteria, archaea, algae and/or yeast, to kill bacteria, archaea, algae and/or yeast, to identify the phenotype of a gene or genes, and/or to screen for reduced genome size and/or a gene deletion in bacteria, archaea, algae and/or yeast.

BACKGROUND OF THE INVENTION

Clustered Regularly Interspaced Short Palindromic Repeats (CRISPR), in combination with associated sequences (cas), constitute the CRISPR-Cas system, which confers adaptive immunity in many bacteria. CRISPR-mediated immunization occurs through the uptake of DNA from invasive genetic elements such as plasmids and phages, as novel "spacers."

CRISPR-Cas systems consist of arrays of short DNA repeats interspaced by hypervariable sequences, flanked by cas genes, that provide adaptive immunity against invasive genetic elements such as phage and plasmids, through sequence-specific targeting and interference (Barrangou et al. 2007. *Science.* 315:1709-1712; Brouns et al. 2008. *Science* 321:960-4; Horvath and Barrangou. 2010. *Science.* 327:167-70; Marraffini and Sontheimer. 2008. *Science.* 322: 1843-1845; Bhaya et al. 2011. *Annu. Rev. Genet.* 45:273-297; Terns and Terns. 2011. *Curr. Opin. Microbiol.* 14:321-327; Westra et al. 2012. *Annu. Rev. Genet.* 46:311-339; Barrangou R. 2013. *RNA.* 4:267-278). Typically, invasive DNA sequences are acquired as novel "spacers" (Barrangou et al. 2007. *Science.* 315:1709-1712), each paired with a CRISPR repeat and inserted as a novel repeat-spacer unit in the CRISPR locus. Subsequently, the repeat-spacer array is transcribed as a long pre-CRISPR RNA (pre-crRNA) (Brouns et al. 2008. *Science* 321:960-4), which is processed into small interfering CRISPR RNAs (crRNAs) that drive sequence-specific recognition. Specifically, crRNAs guide nucleases towards complementary targets for sequence-specific nucleic acid cleavage mediated by Cas endonucleases (Garneau et al. 2010. *Nature.* 468:67-71; Haurwitz et al. 2010. *Science.* 329:1355-1358; Sapranauskas et al. 2011. *Nucleic Acid Res.* 39:9275-9282; Jinek et al. 2012. *Science.* 337:816-821; Gasiunas et al. 2012. *Proc. Natl. Acad. Sci.* 109:E2579-E2586; Magadan et al. 2012. *PLoS One.* 7:e40913; Karvelis et al. 2013. *RNA Biol.* 10:841-851). These widespread systems occur in nearly half of bacteria (~46%) and the large majority of archaea (~90%).

In general terms, there are two main classes (Makarova et al. *Nat Rev Microbiol.* 13:722-736 (2015)) of CRISPR-Cas systems, which encompass five major types and 16 different subtypes based on cas gene content, cas operon architecture, Cas protein sequences, and process steps (Makarova et al. *Biol Direct.* 6:38 (2011); Makarova and Koonin *Methods Mol Biol.* 1311:47-75 (2015); Barrangou, R. *Genome Biology* 16:247 (2015)). In types I and III, the specialized Cas endonucleases process the pre-crRNAs, which then assemble into a large multi-Cas protein complex capable of recognizing and cleaving nucleic acids complementary to the crRNA. Type I systems are the most frequent and widespread systems, which target DNA in a Cascade-driven and PAM-dependent manner, destroying target nucleic acids by using the signature protein Cas3. A different process is involved in Type II CRISPR-Cas systems. Here, the pre-CRNAs are processed by a mechanism in which a trans-activating crRNA (tracrRNA) hybridizes to repeat regions of the crRNA. The hybridized crRNA-tracrRNA are cleaved by RNase III and following a second event that removes the 5' end of each spacer, mature crRNAs are produced that remain associated with the both the tracrRNA and Cas9. The mature complex then locates a target dsDNA sequence ('protospacer' sequence) that is complementary to the spacer sequence in the complex and cuts both strands. Target recognition and cleavage by the complex in the type II system not only requires a sequence that is complementary between the spacer sequence on the crRNA-tracrRNA complex and the target 'protospacer' sequence but also requires a protospacer adjacent motif (PAM) sequence located at the 3' end of the protospacer sequence.

SUMMARY OF THE INVENTION

One aspect of the invention provides a method of screening a population of bacterial cells for essential genes, non-essential genes, and/or expendable genomic islands, comprising: introducing into said population of bacterial cells a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of the bacterial cells of said population, thereby producing a population of transformed bacterial cells; determining the presence or absence of a deletion in the population of transformed bacterial, archaeal, algal or yeast cells, wherein the presence of a deletion in the population of transformed bacterial, archaeal or yeast cells means that the target region is comprised within a non-essential gene and/or an expendable genomic island, and the absence of a deletion in the population of transformed bacterial, archaeal, algal or yeast cells means that the target region is comprised within an essential gene. A CRISPR array useful with this invention may be Type I, Type II, Type III, Type IV or Type V CRISPR array.

A second aspect of the invention provides a method of screening a population of bacterial, archaeal, algal or yeast cells for essential genes, non-essential genes, and/or expendable genomic islands, comprising: introducing into the population of bacterial, archaeal, algal or yeast cells (a) a heterologous nucleic acid construct comprising a trans-encoded CRISPR (tracr) nucleic acid, (b) a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome (chromosomal and/or plasmid) of the bacterial, archaeal, algal or yeast cells of said population, and (c) a Cas9 polypeptide or a heterologous nucleic acid construct comprising a polynucleotide encoding a Cas9 polypeptide, thereby producing a population of transformed bacterial, archaeal, algal or yeast cells; and determining the presence or absence of a deletion in the population of transformed bacterial, archaeal, algal or yeast cells, wherein the presence of a deletion in the population of transformed bacterial, archaeal or yeast cells means that the target region is comprised within a non-essential gene and/or an expendable genomic island, and the absence of a deletion in the population of transformed bacterial, archaeal, algal or yeast cells means that the target region is comprised within an essential gene.

A third aspect of the invention provides a method of killing one or more bacterial cells within a population of bacterial cells, comprising: introducing into the population of bacterial cells a heterologous nucleic acid construct comprising a CRISPR array (crRNA, crDNA) comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of the bacterial cells of said population, thereby killing one or more bacterial cells that comprise the target region within the population of bacterial cells. A CRISPR array useful with this invention may be Type I, Type II, Type III, Type IV or Type V CRISPR array.

A fourth aspect of the invention provides a method of killing one or more cells within a population of bacterial, archaeal, algal or yeast cells, comprising: introducing into the population of bacterial, archaeal, algal or yeast cells (a) a heterologous nucleic acid construct comprising a trans-encoded CRISPR (tracr) nucleic acid, (b) a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome (chromosomal and/or plasmid) of the bacterial, archaeal, algal or yeast cells of said population, and (c) a Cas9 polypeptide and/or a heterologous nucleic acid construct comprising a polynucleotide encoding a Cas9 polypeptide, thereby killing one or more cells within a population of bacterial, archaeal, algal or yeast cells that comprise the target region in their genome.

A fifth aspect of the invention provides a method of identifying a phenotype associated with a bacterial gene, comprising: introducing into a population of bacterial cells a heterologous nucleic acid construct comprising a CRISPR array comprising (5' to 3') a repeat-spacer-repeat sequence or at least one repeat-spacer sequence, wherein the spacer of the at least one repeat-spacer sequence and repeat-spacer-repeat sequence comprises a nucleotide sequence that is substantially complementary to a target region in the genome of the bacterial cells of said population, wherein the target region comprises at least a portion of an open reading frame encoding a polypeptide or functional nucleic acid, thereby killing the cells comprising the target region and producing a population of transformed bacterial cells without the target region; and analyzing the phenotype of the population. A CRISPR array useful with this invention may be Type I, Type II, Type III, Type IV or Type V CRISPR array.

A sixth aspect of the invention provides a method of identifying a phenotype of a bacterial, archaeal, algal or yeast gene, comprising: introducing into a population of bacterial, archaeal, algal or yeast cells (a) a heterologous nucleic acid construct comprising a trans-encoded CRISPR (tracr) nucleic acid, (b) a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome (chromosomal and/or plasmid) of the bacterial, archaeal, algal or yeast cells of said population, and (c) a Cas9 polypeptide and/or a heterologous nucleic acid construct comprising a polynucleotide encoding a Cas9 polypeptide, thereby killing the bacterial, archaeal or yeast cells comprising the target region and producing a population of transformed bacterial, archaeal, algal or yeast cells without the target region; and analyzing the phenotype of the population of transformed bacterial, archaeal, algal or yeast cells, and/or (i) growing individual bacterial, archaeal, algal or yeast colonies from the population of transformed bacterial, archaeal, algal or yeast cells and (ii) analyzing the phenotype of the individual colonies.

A seventh aspect of the invention provides a method of selecting one or more bacterial cells having a reduced genome size from a population of bacterial cells, comprising: introducing into a population of bacterial cells a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of one or more bacterial cells of said population, wherein the cells comprising the target region are killed, thereby selecting one or more bacterial cells without the target region and having a reduced genome size from the population of bacterial cells. A CRISPR array useful with this invention may be Type I, Type II, Type III, Type IV or Type V CRISPR array.

An eighth aspect of the invention provides a method of selecting one or more bacterial cells having a reduced genome size from a population of bacterial cells, comprising: introducing into a population of bacterial cells (a)(i) one or more heterologous nucleic acid constructs comprising a nucleotide sequence having at least 80 percent identity to at least 300 consecutive nucleotides present in the genome of said bacterial cells or (ii) two or more heterologous nucleic acid constructs comprising at least one transposon, thereby producing a population of transgenic bacterial cells comprising a non-natural site for homologous recombination between the one or more heterologous nucleic acid constructs integrated into the genome and the at least 300 consecutive nucleotides present in the genome, or between a first and a second transposon integrated into the genome; and (b) a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of one or more bacterial cells of said population, wherein the target region is located between the one or more heterologous nucleic acid constructs introduced into the genome and the at least 300 consecutive nucleotides present in the genome and/or between the first transposon and second transposon, and cells comprising the target region are killed, thereby selecting one or more bacterial cells without the target region and having a reduced genome size from the population of transgenic bacterial cells. A CRISPR array useful with this invention may be Type I, Type II, Type III, Type IV or Type V CRISPR array.

A ninth aspect of the invention provides a method of selecting one or more bacterial, archaeal, algal or yeast cells having a reduced the genome size from a population of bacterial, archaeal, algal or yeast cells, comprising: introducing into a population of bacterial, archaeal, algal or yeast cells (a) a heterologous nucleic acid construct comprising a trans-encoded CRISPR (tracr) nucleic acid, (b) a heterologous nucleic acid construct comprising a CRISPR array comprising a repeat-spacer-repeat sequence or at least one repeat-spacer sequence, wherein the spacer of the at least one repeat-spacer sequence and the at least one repeat-spacer-repeat sequence comprises a nucleotide sequence that is substantially complementary to a target region in the genome (chromosomal and/or plasmid) of the bacterial, archaeal, algal or yeast cells of said population, and (c) a Cas9 polypeptide and/or a heterologous nucleic acid construct comprising a polynucleotide encoding a Cas9 polypeptide, wherein cells comprising the target region are killed, thereby selecting one or more bacterial, archaeal, algal or yeast cells without the target region and having a reduced genome size from the population of bacterial, archaeal, algal or yeast cells.

A tenth aspect of the invention provides a method of selecting one or more bacterial, archaeal, algal or yeast cells having a reduced the genome size from a population of bacterial, archaeal or yeast cells, comprising: introducing into a population of bacterial, archaeal, algal or yeast cells: (a)(i) one or more heterologous nucleic acid constructs comprising a nucleotide sequence having at least 80 percent identity to at least 300 consecutive nucleotides present in the genome of said bacterial, archaeal, algal or yeast cells, or (ii) two or more heterologous nucleic acid constructs comprising at least one transposon, thereby producing a population of transgenic bacterial, archaeal, algal or yeast cells comprising a non-natural site for homologous recombination between the one or more heterologous nucleic acid constructs integrated into the genome and the at least 300 consecutive nucleotides present in the genome, or between a first and a second transposon integrated into the genome; and (b)(i) a heterologous nucleic acid construct comprising a trans-encoded CRISPR (tracr) nucleic acid, (ii) a heterologous nucleic acid construct comprising a CRISPR array comprising a repeat-spacer-repeat sequence or at least one repeat-spacer sequence, wherein the spacer of the at least one repeat-spacer sequence and the at least one repeat-spacer-repeat sequence comprises a nucleotide sequence that is substantially complementary to a target region in the genome (chromosomal and/or plasmid) of one or more bacterial, archaeal, algal or yeast cells of said population, and (iii) a Cas9 polypeptide and/or a heterologous nucleic acid construct comprising a polynucleotide encoding a Cas9 polypeptide, wherein the target region is located between the one or more heterologous nucleic acid constructs incorporated into the genome and the at least 300 consecutive nucleotides present in the genome and/or between the first transposon and second transposon, and cells comprising the target region are killed, thereby selecting one or more bacterial, archaeal, algal or yeast cells without the target region and having a reduced genome size from the population of transgenic bacterial, archaeal, algal or yeast cells.

An eleventh aspect of the invention provides a method of identifying in a population of bacteria at least one isolate having a deletion in its genome, comprising: introducing into a population of bacterial cells a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of one or more bacterial cells of said population, wherein cells comprising the target region are killed, thereby producing a population of transformed bacterial cells without the target region; and growing individual bacterial colonies from the population of transformed bacterial cells, thereby identifying at least one isolate from the population of transformed bacteria having a deletion in its genome. A CRISPR array useful with this invention may be Type I, Type II, Type III, Type IV or Type V CRISPR array.

A twelfth aspect of the invention provides a method of identifying in a population of bacteria at least one isolate having a deletion in its genome, comprising: introducing into the population of bacterial cells (a)(i) one or more heterologous nucleic acid constructs comprising a nucleotide sequence having at least 80 percent identity to at least 300 consecutive nucleotides present in the genome of said bacterial cells or (ii) two or more heterologous nucleic acid constructs comprising at least one transposon, thereby producing a population of transgenic bacterial cells comprising a non-natural site for homologous recombination between the one or more heterologous nucleic acid constructs integrated into the genome and the at least 300 consecutive nucleotides present in the genome, or between a first and a second transposon integrated into the genome; and b) a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of one or more bacterial cells of said population, wherein the target region is located between the one or more heterologous nucleic acid constructs introduced into the genome and the at least 300 consecutive nucleotides present in the genome and/or between the first transposon and second transposon, and cells comprising the target region are killed, thereby producing a population of transformed bacterial cells without the target region; and growing individual bacterial colonies from the population of transformed bacterial cells, thereby identifying at least one isolate from the population of bacteria having a deletion in its genome. A CRISPR array useful with this invention may be Type I, Type II, Type III, Type IV or Type V CRISPR array.

A thirteenth aspect of the invention provides a method of identifying in a population of bacterial, archaeal, algal or yeast cells at least one isolate having a deletion in its genome, comprising: introducing into a population of bacterial, archaeal, algal or yeast cells: (a) a heterologous nucleic acid construct comprising a trans-encoded CRISPR (tracr) nucleic acid, (b) a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome (chromosomal and/or plasmid) of the bacterial, archaeal, algal or yeast cells of said population, and (c) a Cas9 polypeptide or a heterologous nucleic acid construct comprising a polynucleotide encoding a Cas9 polypeptide, wherein cells comprising the target region are killed, thereby producing a population of transformed bacterial, archaeal, algal or yeast cells without the target region; and growing individual bacterial, archaeal or yeast colonies from the population of transformed bacterial, archaeal, algal or yeast cells, thereby identifying at least one isolate from the population of transformed bacterial, archaeal, algal or yeast cells having a deletion in its genome.

A fourteenth aspect of the invention provides a method of identifying in a population of bacterial, archaeal, algal or yeast cells at least one isolate having a deletion in its genome, comprising: introducing into the population of bacterial, archaeal, algal or yeast cells (a)(i) one or more heterologous nucleic acid constructs comprising a nucleotide sequence having at least 80 percent identity to at least 300 consecutive nucleotides present in the genome of said bacterial, archaeal, algal or yeast cells, or (ii) two or more heterologous nucleic acid constructs comprising at least one transposon, thereby producing a population of transgenic bacterial, archaeal, algal or yeast cells comprising a non-natural site for homologous recombination between the one or more heterologous nucleic acid constructs integrated into the genome and the at least 300 consecutive nucleotides present in the genome, or between a first and a second transposon integrated into the genome; and (b)(i) a heterologous nucleic acid construct comprising a trans-encoded CRISPR (tracr) nucleic acid, (ii) a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome (chromosomal and/or plasmid) of one or more bacterial, archaeal, algal or yeast cells of said population, and (iii) a Cas9 polypeptide and/or a heterologous nucleic acid construct comprising a polynucleotide encoding a Cas9 polypeptide, wherein the target region is located between the one or more heterologous nucleic acid constructs incorporated into the genome and the at least 300 consecutive nucleotides present in the genome and/or between the first transposon and second transposon, and cells comprising the target region are killed, thereby producing a population of transformed bacterial, archaeal, algal or yeast cells without the target region; and growing individual bacterial, archaeal or yeast colonies from the population of transformed bacterial, archaeal, algal or yeast cells, thereby identifying at least one isolate from the population having a deletion in its genome.

Further provided herein are expression cassettes, cells and kits comprising the nucleic acid constructs, nucleic acid arrays, nucleic acid molecules and/or nucleotide sequences of the invention.

These and other aspects of the invention are set forth in more detail in the description of the invention below.

BRIEF DESCRIPTION OF THE DRAWINGS

FIG. 1 shows the sequence of SthCRISPR1 (SEQ ID NO:1) and SthCRISPR 3 arrays for targeting each composite transposon (LacZ (SEQ ID NO:2), ABC (SEQ ID NO:3), prtS (SEQ ID NO:4), cu (SEQ ID NO:5).

FIG. 5A-5D show the alignments of transposon coding sequences (using Geneious® software) for each major IS family found in the S. thermophilus LMD-9 genome. Different families exhibited varying levels of conservation of length and nucleotide identity. (A) Sth6 transposons were highly polymorphic and apparently degenerate due to internal deletions in some of the copies. In contrast, IS1167 (B) and IS1191 (C) had fewer copies but maintained high fidelity in length and identity. IS1193 (D) had high fidelity copies but exhibited the greatest intra-family diversity in length.

FIGS. 7A-7B shows genome sequencing and phenotypic analysis of Lac⁻ clones. Sequence data revealed an absence of the chromosomal segment encoding lacZ in two mutants independently created by targeting the (A) 5' end (upper panel) and cation-binding residue coding sequences of lacZ using the CRISPR3 system (lower panel). The size of the deletions ranged from 101,865-102,146 bp in length, constituting approximately 5.5% of the genome of *S. thermophilus*. (B) shows growth of large deletion strains compared to wild-type in semi-synthetic Elliker medium represented as mean±SD OD 600 nm of three independent biological replicates (upper panel) and acidification capacity of *S. thermophilus* strains in skim milk (lower panel).

FIG. 13 shows XY plots of genomic island deletion strain expression values (X-axes) verses wild-type expression values (Y-axes). For each of the genomic island deletion strains (GEI1-GEI4), the expression of genes encoded on each of the target islands (black) was minimal. Genes encoded in GEI1 are shown in the top panel, genes encoded in GEI2 are shown in the second panel from the top, genes encoded in GEI3 are shown in the third panel from the top, and genes encoded in GEI4 are shown in the bottom panel.

FIG. 21 provides an exemplary Type I CRISPR-Cas guide of *Lactobacillus casei*. The sequence provided is the native Type I leader (SEQ ID NO:49) and repeat that is found in *Lactobacillus casei* NCK 125. This artificial array contains a spacer that targets the 16s rDNA gene in the host genome. Repeat-spacer-repeat: SEQ ID NO:50.

DETAILED DESCRIPTION

Figure 2:
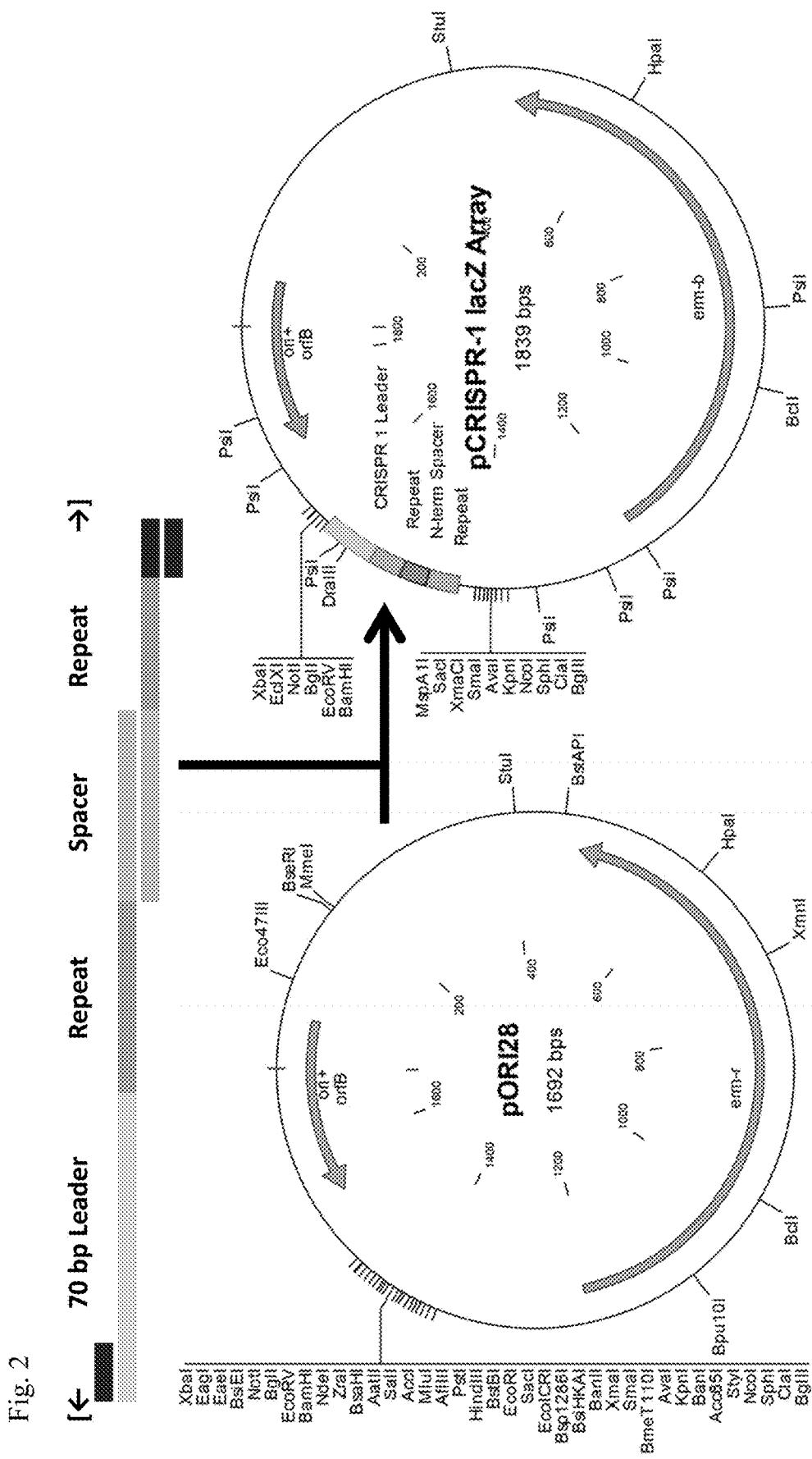
FIG. 2 shows a schematic of the splicing overlap extension (SOE) method for construction of targeting plasmids.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

"Cas9 nuclease" refers to a large group of endonucleases that catalyze the double stranded DNA cleavage in the CRISPR Cas system. These polypeptides are well known in the art and many of their structures (sequences) are characterized (See, e.g., WO2013/176772; WO/2013/188638). The domains for catalyzing the cleavage of the double stranded DNA are the RuvC domain and the HNH domain. The RuvC domain is responsible for nicking the (−) strand and the HNH domain is responsible for nicking the (+) strand (See, e.g., Gasiunas et al. *PNAS* 109(36):E2579-E2586 (Sep. 4, 2012)).

As used herein, "chimeric" refers to a nucleic acid molecule or a polypeptide in which at least two components are derived from different sources (e.g., different organisms, different coding regions).

"Complement" as used herein can mean 100% complementarity or identity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, "contact," contacting," "contacted," and grammatical variations thereof, refers to placing the components of a desired reaction together under conditions suitable for carrying out the desired reaction (e.g., integration, transformation, screening, selecting, killing, identifying, amplifying, and the like). The methods and conditions for carrying out such reactions are well known in the art (See, e.g., Gasiunas et al. (2012) Proc. Natl. Acad. Sci. 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

A "deletion" as used herein can comprise the loss or deletion of genetic material including but not limited to a deletion of a portion of a chromosome or a plasmid, a deletion of a gene or a portion of a gene from a chromosome or a plasmid. In some embodiments, a deletion can comprise one gene or more than one gene. In some embodiments, a deletion may also comprise the loss of non-protein-coding regions that may encode small non-coding RNAs. In some embodiments, a deletion can comprise the loss of an entire plasmid or of an entire mobile genetic element. In some embodiments, the loss of a mobile genetic element may be defined as, for example, an inability to replicate or persist.

In some embodiments, a a phasmid of the invention may comprise a CRISPR array from a Type I CRISPR-Cas system, a Type II CRISPR-Cas system, a Type III CRISPR-Cas system, a Type IV CRISPR-Cas system, and/or a Type V CRISPR-Cas system (see, Makarova et al. *Nature Reviews Biotechnology* 13:722736 (2015)).

Thus, in some embodiments, in addition to a Type I crRNA, a phasmid of the invention may comprise Type I polypeptides and/or Type I Cascade polypeptides (i.e., a Type I CRISPR-Cas system).

As used herein, "Type I polypeptide" refers to any of a Cas3 polypeptide, Cas3' polypeptide, a Cas3" polypeptide, fusion variants thereof, and any one or more of the Type I Clustered Regularly Interspaced Short Palindromic Repeats (CRISPR)-associated complex for antiviral defense ("Cascade") polypeptides. Thus, the term "Type I polypeptide" refers to the polypeptides that make up a Type I-A CRISPR-Cas system, a Type I-B CRISPR-Cas system, a Type I-C CRISPR-Cas system, a Type I-D CRISPR-Cas system, a Type I-E CRISPR-Cas system, a Type I-F CRISPR-Cas system, and/or a Type I-U CRISPR-Cas system. Each Type-I CRISPR-Cas system comprises at least one Cas3 polypeptide. Cas3 polypeptides generally comprise both a helicase domain and an HD domain. However, in some Type I CRISPR-Cas systems, the helicase and HD domain are found in separate polypeptides, Cas3' and Cas3". In particular, Cas3' encodes the helicase domain whereas Cas3" encodes the HD domain. Consequently, because both domains are required for Cas3 function, Type I subtypes either encode Cas3 (I-C, I-D, I-E, I-F, I-U) or Cas3' and Cas3" (I-A, I-B).

As used herein, "Type I Cascade polypeptides" refers to a complex of polypeptides involved in processing of pre-crRNAs and subsequent binding to the target DNA in Type I CRISPR-Cas systems. These polypeptides include, but are not limited to, the Cascade polypeptides of Type I subtypes I-A, I-B, I-C, I-D, I-E and I-F. Non-limiting examples of Type I-A Cascade polypeptides include Cas7 (Csa2), Cas8a1 (Csx13), Cas8a2 (Csx9), Cas5, Csa5, Cas6a, Cas3' and/or a Cas3". Non-limiting examples of Type I-B Cascade polypeptides include Cas6b, Cas8b (Csh1), Cas7 (Csh2) and/or Cas5. Non-limiting examples of Type I-C Cascade polypeptides include Cas5d, Cas8c (Csd1), and/or Cas7 (Csd2). Non-limiting examples of Type I-D Cascade polypeptides include Cas10d (Csc3), Csc2, Csc1, and/or Cas6d. Non-limiting examples of Type I-E Cascade polypeptides include Cse1 (CasA), Cse2 (CasB), Cas7 (CasC), Cas5 (CasD) and/or Cas6e (CasE). Non-limiting examples of Type I-F Cascade polypeptides include Cys1, Cys2, Cas7 (Cys3) and/or Cas6f (Csy4). Non-limiting examples of Type I-U Cascade polypeptides include Cas8c, Cas7, Cas5, Cas6 and/or Cas4.

In some embodiments, a phasmid of the invention may comprise may comprise a Type II CRISPR-Cas system in addition to a Type II crRNA. Type II CRISPR-Cas systems comprise three subtypes: Type II-A, Type II-B and Type II-C, each of which comprise the multidomain protein, Cas9, in addition to the adaptation polypeptides, Cas1, Cas2 and optionally, Csn2 and/or Cas4. Most Type II loci also encode a tracrRNA. Organisms comprising exemplary Type II CRISPR-Cas systems include *Legionella pneumophila* str. Paris, *Streptococcus thermophilus* CNRZ1066 and *Neisseria lactamica* 020-06.

In additional embodiments, a phasmid of the invention may comprise may comprise a Type III CRISPR-Cas system in addition to a Type III crRNA. Similar to Type I CRISPR-Cas systems, in Type III systems processing and interference is mediated by multiprotein CRISPR RNA (crRNA)-effector complexes (Makarova et al. *Nature Reviews Biotechnology* 13:722736 (2015))—"CASCADE" in Type I and "Csm" or "Cmr" in Type III. Thus, in some embodiments, a Type III CRISPR-Cas system can comprise a Csm complex (e.g., Type III-A Csm) and/or a Cmr complex (e.g., Type III-B Cmr), and optionally a Cas6 polypeptide. In representative embodiments, a Csm complex may comprise Cas10 (or Csm1), Csm2, Csm3, Csm4, Csm5, and Csm6 polypeptides and a Cmr complex may comprise Cmr1, Cas10 (or Cmr2), Cmr3, Cmr4, Cmr5, and Cmr6 polypeptides. In addition to the Csm complex or Cmr complex, a Type III CRISPR-Cas system may further comprise a Cas7 polypeptide. Four subtypes of a Type III CRISPR-Cas system have been characterized, III-A, III-B, III-D. In some embodiments, a Type III-A CRISPR-Cas system comprises Cas6, Cas10, Csm2, Cas7 (Csm3), Cas5 (Csm4), Cas7 (Csm5), and Csm6 polypeptides. In some embodiments, a Type III-B CRISPR-Cas system comprises Cas7 (Cmr1), Cas10, Cas5 (Cmr3), Cas7 (Cmr4), Cmr5, Cas6, and Cas7 (Cmr6) polypeptides. In some embodiments, a Type III-C CRISPR-Cas system comprises Cas7 (Cmr1), Cas7 (Cmr6), Cas10, Cas7 (Cmr4), Cmr5 and Cas5 (Cmr3), polypeptides. In some embodiments, a Type III-D CRISPR-Cas system comprises Cas10, Cas7 (Csm3), Cas5 (Csx10), Csm2, Cas7 (Csm3), and all1473 polypeptides.

In some embodiments, a phasmid of the invention may comprise a Type IV CRISPR-Cas system, in addition to a Type IV crRNA. Type IV CRISPR-Cas systems can comprise a Csf4 polypeptide (dinG) and/or a Csf1, Cas7 (Csf2) and/or Cas5 (csf3) polypeptide. (Makarova et al. *Nature Reviews Microbiology* 13:722-736 (2015)).

In some embodiments, a phasmid of the invention further comprises a Type V CRISPR-Cas system, in addition to a Type V crRNA. Type V CRISPR-Cas systems can comprise a Cpf1 polypeptide and/or a Cas1, Cas2 and/or Cas4 polypeptide. (Makarova et al. *Nature Reviews Microbiology* 13:722-736 (2015)).

A "fragment" or "portion" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or substantially identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. Thus, hybridizing to (or hybridizes to, and other grammatical variations thereof), for example, at least a portion of a target DNA (e.g., target region in the genome), refers to hybridization to a nucleotide sequence that is identical or substantially identical to a length of contiguous nucleotides of the target DNA. In some embodiments, a repeat of a repeat spacer sequence or a repeat-spacer-repeat sequence can comprise a fragment of a repeat sequence of a wild-type CRISPR locus or a repeat sequence of a synthetic CRISPR array, wherein the fragment of the repeat retains the function of a repeat in a CRISPR array of hybridizing with the tracr nucleic acid.

In some embodiments, the invention may comprise a functional fragment of a Cas9, Cas3, Cas3', Cas3", or Cpf1 nuclease. A Cas9 functional fragment retains one or more of the activities of a native Cas9 nuclease including, but not limited to, HNH nuclease activity, RuvC nuclease activity, DNA, RNA and/or PAM recognition and binding activities. A functional fragment of a Cas9 nuclease may be encoded by a fragment of a Cas9 polynucleotide. A Cas3, Cas3' or Cas3" functional fragment retains one or more of the activities of a native Cas9 nuclease including, but not limited to, nickase activity, exonuclease activity, DNA-binding, and/or RNA binding. A functional fragment of a Cas3, Cas3' or Cas3" nuclease may be encoded by a fragment of a Cas3, Cas3' or Cas3" polynucleotide, respectively.

As used herein, the term "gene" refers to a nucleic acid molecule capable of being used to produce mRNA, antisense RNA, RNAi (miRNA, siRNA, shRNA), anti-microRNA antisense oligodeoxyribonucleotide (AMO), and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "genome" as used herein includes an organism's chromosomal/nuclear genome as well as any mitochondrial, and/or plasmid genome.

A "hairpin sequence" as used herein, is a nucleotide sequence comprising hairpins (e.g., that forms one or more hairpin structures). A hairpin (e.g., stem-loop, fold-back) refers to a nucleic acid molecule having a secondary structure that includes a region of complementary nucleotides that form a double strand that are further flanked on either side by single stranded-regions. Such structures are well known in the art. As known in the art, the double stranded region can comprise some mismatches in base pairing or can be perfectly complementary. In some embodiments of the present disclosure, a hairpin sequence of a nucleic acid construct can be located at the 3'end of a tracr nucleic acid.

A "heterologous" or a "recombinant" nucleotide sequence is a nucleotide sequence not naturally associated with a host cell into which it is introduced, including non-naturally occurring multiple copies of a naturally occurring nucleotide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention. Thus, for example, a homologue of a Type I, Type II, Type III, Type IV, or Type V polynucleotide or polypeptide can be about 70% homologous or more to any one of any known or later identified Type I, Type II, Type III, Type IV, or Type V polynucleotide or polypeptide.

As used herein, hybridization, hybridize, hybridizing, and grammatical variations thereof, refer to the binding of two fully complementary nucleotide sequences or substantially complementary sequences in which some mismatched base pairs may be present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein, the terms "increase," "increasing," "increased," "enhance," "enhanced," "enhancing," and "enhancement" (and grammatical variations thereof)

describe an elevation of at least about 25%, 50%, 75%, 100%, 150%, 200%, 300%, 400%, 500% or more as compared to a control.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is a mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Except as otherwise indicated, nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences, CRISPR repeat-spacer-repeat sequences, and/or CRISPR arrays.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount of the component being measured (e.g., the population of cells or a genome size). Thus, for example, a reduced genome size can mean a reduction in the size of a genome of at least about 5%, 10%, 15%, 20%, 25%, 35%, 50%, 75%, 80%, 85%, 90%, 95%, 97%, 98%, 99%, or 100% as compared to a control.

A control as used herein may be, for example, a population of bacterial, archaeal, algal or yeast cells that has not been transformed with a heterologous nucleic acid construct of this invention. In some embodiments, a control may be a wild-type population of bacterial, archaeal, algal or yeast cells, or it may be a population of bacterial, archaeal or yeast cells transformed with a heterologous construct comprising a CRISPR array comprising a repeat-spacer-repeat sequence or at least one repeat-spacer sequence, wherein the spacer comprises a nucleotide sequence that is not complementary to a target region in the genome of the bacterial, archaeal or yeast cells of said population (i.e., non-self targeting/ "scrambled spacer"). In additional aspects, a control may be, for example, a wild-type population of bacterial, archaeal, algal or yeast cells, or a population of bacterial, archaeal, algal or yeast cells transformed with a heterologous construct comprising a CRISPR array comprising a repeat-spacer-repeat sequence or at least one repeat-spacer sequence, wherein the spacer comprises a nucleotide sequence that is substantially complementary to a target region in the genome of the bacterial, archaeal, algal or yeast cells of said population that is not located adjacent to a protospacer adjacent motif (PAM).

A "repeat sequence" as used herein refers, for example, to any repeat sequence of a wild-type CRISPR locus or a repeat sequence of a synthetic CRISPR array that are separated by "spacer sequences" (e.g., a repeat-spacer sequence or a repeat-spacer-repeat sequence of the invention). A repeat sequence useful with this invention can be any known or later identified repeat sequence of a CRISPR locus. Accordingly, in some embodiments, a repeat-spacer sequence or a repeat-spacer-repeat comprises a repeat that is substantially identical (e.g. at least about 70% identical (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a repeat from a wild-type Type II CRISPR array. In some embodiments, a repeat sequence is 100% identical to a repeat from a wild type Type I CRISPR array, a wild type Type II CRISPR array, wild type Type III CRISPR array, wild type Type IV CRISPR array, or wild type Type V CRISPR array. In additional embodiments, a repeat sequence useful with this invention can comprise a nucleotide sequence comprising a partial repeat that is a fragment or portion of a consecutive nucleotides of a repeat sequence of a CRISPR locus or synthetic CRISPR array of any of a Type I crRNA, Type II crRNA, Type III crRNA, Type IV crRNA, or Type V crRNA.

As used herein, "CRISPR array" of a Type I, Type II, Type III, Type IV, or Type V CRISPR-Cas system refers to a nucleic acid construct that comprises from 5' to 3' a repeat-spacer-repeat sequence or comprises from 5' to 3' at least one repeat-spacer sequence (e.g., about 1, 2, 3, 4, 5, 6, 7, 8, 9, 10, 11, 12, 13, 14, 15, 16, 17, 18, 19, 20, 21, 22, 23, 24, or 25 repeat-spacer sequences, and any range or value therein). When more than one repeat-spacer is comprised in a CRISPR array, the spacer of the prior (5' to 3') repeat-spacer sequence can be linked to the repeat of the following repeat-spacer (e.g., the spacer of a first repeat-spacer sequence is linked to the repeat of a second repeat-spacer sequence). In some embodiments, a CRISPR array can comprise two repeats (or two partial repeats) separated by a spacer (e.g., a repeat-spacer-repeat sequence).

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

A "spacer sequence" as used herein is a nucleotide sequence that is complementary to a target DNA (i.e., target region in the genome or the "protospacer sequence", which is adjacent to a protospacer adjacent motif (PAM) sequence). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target DNA. In representative embodiments, the spacer sequence has 100% complementarity to the target DNA. In additional embodiments, the complementarity of the 3' region of the spacer sequence to the target DNA is 100% but is less than 100% in the 5' region of the spacer and therefore the overall complementarity of the spacer sequence to the target DNA is less than 100%. Thus, for example, the first 7, 8, 9, 10, 11, 12, 13, 14, 15, 16, and the like, nucleotides in the 3' region of a 20 nucleotide spacer sequence (seed sequence) can be 100% complementary to the target DNA, while the remaining nucleotides in the 5' region of the spacer sequence are substantially complementary (e.g., at least about 70% complementary) to the target DNA. In some embodiments, the first 7 to 12 nucleotides of the spacer sequence can be 100% complementary to the target DNA, while the remaining nucleotides in the 5' region of the spacer sequence are substantially complementary (e.g., at least about 70% complementary) to the target DNA. In other embodiments, the first 7 to 10 nucleotides of the spacer sequence can be 100% complementary to the target DNA, while the remaining nucleotides in the 5' region of the spacer sequence are substantially complementary (e.g., at least about 70% complementary) to the target DNA. In representative embodiments, the first 7 nucleotides (within the seed) of the spacer sequence can be 100% complementary to the target DNA, while the remaining nucleotides in the 5' region of the spacer sequence are substantially complementary (e.g., at least about 70% complementary) to the target DNA.

As used herein, a "target DNA," "target region" or a "target region in the genome" refers to a region of an organism's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a repeat-spacer sequence or repeat-spacer-repeat sequence. In some embodiments, a target region may be about 10 to about 40 consecutive nucleotides in length located immediately adjacent to a PAM sequence (PAM sequence located immediately 3' of the target region) in the genome of the organism (e.g., Type I CRISPR-Cas systems and Type II CRISPR-Cas systems). In the some embodiments, e.g., Type I systems, the PAM is on the alternate side of the protospacer (the 5' end). There is no known PAM for Type III systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

In some embodiments, a target region useful with this invention is located within an essential gene or a non-essential gene.

In representative embodiments, a target region can be randomly selected or can be specifically selected. In some embodiments, a randomly selected target region may be selected from any at least 10 consecutive nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, and the like, and any range or value therein) located immediately adjacent to a PAM sequence in a bacterial, archaeal, algal or yeast genome. In some embodiments, the target region can be about 10 to about 20 consecutive nucleotides, about 10 to about 30 consecutive nucleotides, and/or about 10 to about 40 consecutive nucleotides and the like, or any range or value therein, located immediately adjacent to a protospacer adjacent motif (PAM) sequence in a bacterial, archaeal, algal or yeast genome. In some embodiments, specifically selecting a target region can comprise selecting two or more target regions that are located about every 100 nucleotides to about every 1000 nucleotides, about every 100 nucleotides to about every 2000, about every 100 nucleotides to about every 3000, about every 100 nucleotides to about every 4000, and/or about every 100 nucleotides to about every 5000 nucleotides, and the like, from one another in the genome of the one or more bacteria, archaea, algal or yeast cells. In particular embodiments, specifically selecting a target region comprises specifically selecting a target region from a gene, open reading frame, a putative open reading frame or an intergenic region comprising at least about 10 to about 40 consecutive nucleotides immediately adjacent to a PAM sequence in a bacterial, archaeal, algal or yeast genome.

A "trans-activating CRISPR (tracr) nucleic acid" or "tracr nucleic acid" as used herein refers to any tracr RNA (or its encoding DNA). A tracr nucleic acid comprises from 5' to 3' a lower stem, an upper stem, a bulge, a nexus hairpin and terminal hairpins (See, Briner et al. (2014) *Molecular Cell.* 56(2):333-339). A trans-activating CRISPR (tracr) nucleic acid functions in hybridizing to the repeat portion of mature or immature crRNAs, recruits Cas9 protein to the target site, and may facilitate the catalytic activity of Cas9 by inducting structural rearrangement. The functional composition of tracrRNA molecules is listed above. Sequences for tracrRNAs are specific to the CRISPR-Cas system and can be variable. Any tracr nucleic acid, known or later identified, can be used with this invention.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of the invention, the substantial identity exists over a region of the sequences that is at least about 3 to about 15 (e.g., 3, 4, 5, 6, 7, 8, 9, 10, 11, 12, 13, 14, 15 residues in length and the like or any value or any range therein), at least about 5 to about 30, at least about 10 to about 30, at least about 16 to about 30, at least about 18 to at least about 25, at least about 18, at least about 22, at least about 25, at least about 30, at least about 40, at least about 50, about 60, about 70, about 80, about 90, about 100, about 110, about 120, about 130, about 140, about 150, or more residues in length, and any range therein. In representative embodiments, the sequences can be substantially identical over at least about 22 nucleotides. In some particular embodiments, the sequences are substantially identical over at least about 150 residues. In some embodiments, sequences of the invention can be about 70% to about 100% identical over at least about 16 nucleotides to about 25 nucleotides. In some embodiments, sequences of the invention can be about 75% to about 100% identical over at least about 16 nucleotides to about 25 nucleotides. In further embodiments, sequences of the invention can be about 80% to about 100% identical over at least about 16 nucleotides to about 25 nucleotides. In further embodiments, sequences of the invention can be about 80% to about 100% identical over at least about 7 nucleotides to about 25 nucleotides. In some embodiments, sequences of the invention can be about 70% identical over at least about 18 nucleotides. In other embodiments, the sequences can be about 85% identical over about 22 nucleotides. In still other embodiments, the sequences can be 100% identical over about 16 nucleotides. In a further embodiment, the sequences are substantially identical over the entire length of a coding region. Furthermore, in exemplary embodiments, substantially identical nucleotide or polypeptide sequences perform substantially the same function (e.g., the function or activity of a crRNA, tracr nucleic acid, repeat sequence, Cas9 nuclease (nickase, DNA, RNA and/or PAM recognition and binding), Cas3, Cas3', Cas3" or any other CRISPR-Cas polynucleotide or polypeptide).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

Any nucleotide sequence and/or heterologous nucleic acid construct of this invention can be codon optimized for expression in any species of interest. Codon optimization is well known in the art and involves modification of a nucleotide sequence for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original, native nucleotide sequence. Thus, in representative embodiments of the invention, the nucleotide sequence and/or heterologous nucleic acid construct of this invention can be codon optimized for expression in the particular species of interest.

In some embodiments, the heterologous or recombinant nucleic acids molecules, nucleotide sequences and/or polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the heterologous nucleic acid constructs, nucleotide sequences and their encoded polypeptides are "isolated" in that, by the hand of man, they exist apart from their native environment and therefore are not products of nature, however, in some embodiments, they can be introduced into and exist in a recombinant host cell.

In some embodiments, the heterologous or recombinant nucleic acid constructs of the invention are "synthetic." A "synthetic" nucleic acid molecule, a "synthetic" nucleotide sequence or a "synthetic" polypeptide is a nucleic acid molecule, nucleotide sequence or polypeptide that is not found in nature but is created by the hand of man and is therefore not a product of nature.

In any of the embodiments described herein, the nucleotide sequences and/or heterologous nucleic acid constructs of the invention can be operatively associated with a variety of promoters and other regulatory elements for expression in various organisms cells. Thus, in representative embodiments, a nucleic acid construct of this invention can further comprise one or more promoters operably linked to one or more nucleotide sequences.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "prothoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of heterologous nucleic acid constructs, i.e., "chimeric genes" or "chimeric polynucleotides." These various types of promoters are known in the art.

The choice of promoter will vary depending on the temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a nucleic acid construct of the invention can be an "expression cassette" or can be comprised within an expression cassette. As used herein, "expression cassette" means a heterologous nucleic acid construct comprising a nucleotide sequence of interest (e.g., the nucleic acid constructs of the invention (e.g., a synthetic tracr nucleic acid construct, a synthetic CRISPR nucleic acid construct, a synthetic CRISPR array, a chimeric nucleic acid construct; a nucleotide sequence encoding a polypeptide of interest, a Type I polypeptide, Type II polypeptide, Type III polypeptide, Type IV polypeptide, and/or Type V polypeptide)), wherein said nucleotide sequence is operably associated with at least a control sequence (e.g., a promoter). Thus, some aspects of the invention provide expression cassettes designed to express the nucleotides sequences of the invention.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof).

An expression cassette also can include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Of course, many examples of suitable selectable markers are known in the art and can be used in the expression cassettes described herein.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an Agrobacterium binary vector in double or single stranded linear or circular form which may or may not be self transmissible or mobilizable. A vector as defined herein can transform prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the nucleic acid molecules of this invention and/or expression cassettes can be comprised in vectors as described herein and as known in the art.

"Introducing," "introduce," "introduced" (and grammatical variations thereof) in the context of a polynucleotide of interest means presenting the polynucleotide of interest to the host organism or cell of said organism (e.g., host cell) in such a manner that the polynucleotide gains access to the interior of a cell. Where more than one polynucleotide is to be introduced these polynucleotides can be assembled as part of a single polynucleotide or nucleic acid construct, or as separate polynucleotide or nucleic acid constructs, and can be located on the same or different expression constructs or transformation vectors. Accordingly, these polynucleotides can be introduced into cells in a single transformation event, in separate transformation/transfection events, or, for example, they can be incorporated into an organism by conventional breeding protocols. Thus, in some aspects, one or more nucleic acid constructs of this invention can be introduced singly or in combination into a host organism or a cell of said host organism. In the context of a population of cells, "introducing" means contacting the population with the heterologous nucleic acid constructs of the invention under conditions where the heterologous nucleic acid constructs of the invention gain access to the interior of one or more cells of the population, thereby transforming the one or more cells of the population.

The term "transformation" or "transfection" as used herein refers to the introduction of a heterologous nucleic acid into a cell. Transformation of a cell may be stable or transient. Thus, in some embodiments, a host cell or host organism is stably transformed with a nucleic acid construct of the invention. In other embodiments, a host cell or host organism is transiently transformed with a nucleic acid construct of the invention. Thus, in representative embodiments, a heterologous nucleic acid construct of the invention can be stably and/or transiently introduced into a cell.

"Transient transformation" in the context of a polynucleotide means that a polynucleotide is introduced into the cell and does not integrate into the genome of the cell.

By "stably introducing" or "stably introduced," in the context of a polynucleotide, means that the introduced polynucleotide is stably incorporated into the genome of the cell, and thus the cell is stably transformed with the polynucleotide.

"Stable transformation" or "stably transformed" as used herein means that a nucleic acid construct is introduced into a cell and integrates into the genome of the cell. As such, the integrated nucleic acid construct is capable of being inherited by the progeny thereof, more particularly, by the progeny of multiple successive generations. "Genome" as used herein includes the nuclear, mitochondrial and plasmid genome, and therefore may include integration of a nucleic acid construct into, for example, the plasmid or mitochondrial genome. Stable transformation as used herein may also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a bacterium, an archaea, a yeast, an algae, and the like). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Accordingly, in some embodiments, the nucleotide sequences, constructs, expression cassettes can be expressed transiently and/or they can be stably incorporated into the genome of the host organism.

A heterologous nucleic acid construct of the invention can be introduced into a cell by any method known to those of skill in the art. In some embodiments of the invention, transformation of a cell comprises nuclear transformation. In still further embodiments, the heterologous nucleic acid construct (s) of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events, or, alternatively, where relevant, a nucleotide sequence can be incorporated into an organism as part of a breeding protocol.

Mobile genetic elements (MGEs) present bacteria with continuous challenges to genomic stability, promoting evolution through horizontal gene transfer. The term MGE encompasses plasmids, bacteriophages, transposable elements, genomic islands, and many other specialized genetic elements (1). MGEs encompass genes conferring high rates of dissemination, adaptive advantages to the host, and genomic stability, leading to their near universal presence in bacterial genomes. To cope with the permanent threat of predatory bacteriophages and selfish genetic elements, bacteria have evolved both innate and adaptive immune systems targeting exogenous genetic elements. Innate immunity includes cell-wall modification, restriction/modification systems, and abortive phage infection (2). Clustered regularly interspaced short palindromic repeats (CRISPR) and CRISPR-associated genes (Cas) are an adaptive immune system targeted against invasive genetic elements in bacteria (3). CRISPR-Cas mediated immunity relies on distinct molecular processes, categorized as acquisition, expression, and interference (3). Acquisition occurs via molecular 'sampling' of foreign genetic elements, from which short sequences, termed spacers, are integrated in a polarized fashion into the CRISPR array (4). Expression of CRISPR arrays is constitutive and inducible by promoter elements within the preceding leader sequence (5-6). Interference results from a corresponding transcript that is processed selectively at each repeat sequence, forming CRISPR RNAs (crRNAs) that guide Cas proteins for sequence-specific recognition and cleavage of target DNA complementary to the spacer (7). CRISPR-Cas technology has applications in strain typing and detection (8-10), exploitation of natural/engineered immunity against mobile genetic elements (11), programmable genome editing in diverse backgrounds (12), transcriptional control (13-14), and manipulation of microbial populations in defined consortia (15).

The various CRISPR systems are known in the art. For example, see Makarova et al., which describes the nomenclature for all the classes, types and subtypes of CRISPR systems (*Nature Reviews Microbiology* 13:722-736 (2015)); see also, R. Barrangou (*Genome Biol.* 16:247 (2015)).

Although sequence features corresponding to CRISPR arrays were described previously in multiple organisms (16-17), Streptococcus thermophilus was the first microbe where the roles of specific cas genes and CRISPR-array components were elucidated (4). *S. thermophilus* is a non-pathogenic thermophilic Gram-positive bacterium used as a starter culture that catabolizes lactose to lactic acid in the syntrophic production of yogurt and various cheeses (18). *S. thermophilus* encodes up to four CRISPR-Cas systems, two of them (SthCRISPR1 and SthCRISPR3) are classified as Type II-A systems that are innately active in both acquisition and interference (4, 19). Accordingly, genomic analysis of *S. thermophilus* and its bacteriophages established a likely mechanism of CRISPR-Cas systems for phage/DNA protection. Investigation of CRISPR-Cas systems in *S. thermophilus* led to bioinformatic analysis of spacer origin (4, 20), discovery of the proto-spacer adjacent motif (PAM) sequences (19; 21), understanding of phage-host dynamics (22-23), demonstration of Cas9 endonuclease activity (7, 24-25), and recently, determination of the tracrRNA structural motifs governing function and orthogonality of Type II systems (26). Genomic analysis of *S. thermophilus* revealed evolutionary adaptation to milk through loss of carbohydrate catabolism and virulence genes found in pathogenic streptococci (18). *S. thermophilus* also underwent significant acquisition of niche-related genes, such as those encoding including cold-shock proteins, copper resistance proteins, proteinases, bacteriocins, and lactose catabolism proteins (18). Insertion sequences (ISs) are highly prevalent in *S. thermophilus* genomes and contribute to genetic heterogeneity between strains by facilitating dissemination of islands associated with dairy adaptation genes (18). The concomitant presence of MGEs and functional CRISPR-Cas systems in *S. thermophilus* suggests that genome homeostasis is governed at least in part by the interplay of these dynamic forces. Thus, *S. thermophilus* constitutes an ideal host for investigating the genetic outcomes of CRISPR-Cas targeting of genomic islands.

CRISPR-Cas systems have recently been the subject of intense research in genome editing applications (12), but the evolutionary roles of most endogenous microbial systems remain unknown (27). Even less is known concerning evolutionary outcomes of housing active CRISPR-Cas systems beyond the prevention of foreign DNA uptake (7), spacer acquisition events (4), and mutation caused by chromosomal self-targeting (28-32). Thus, the present inventors sought to determine the outcomes of targeting integrated MGEs with endogenous Type II CRISPR-Cas systems. Four islands were identified in *S. thermophilus* LMD-9, with lengths ranging from 8 to 102 kbp and totaling approximately 132 kbp, or 7% of the genome. In order to target genomic islands, plasmid-based expression of engineered CRISPR arrays with self-targeting spacers were transformed into *S. thermophilus* LMD-9. Collectively, our results elucidate fundamental genetic outcomes of self-targeting events and show that CRISPR-Cas systems can direct genome evolution at the bacterial population level.

Utilizing these discoveries, the present inventors have developed novel methods for screening populations of bacterial, archaeal, algal or yeast cells for essential genes, non-essential genes, and/or expendable genomic islands; for killing one or more cells within a population of bacterial, archaeal, algal or yeast cells; for identifying a phenotype of a bacterial, archaeal, algal or yeast gene; for selecting one or more bacterial, archaeal, algal or yeast cells having a reducing the genome size from a population of bacterial, archaeal or yeast cells; and/or for identifying in a population of bacterial, archaeal, algal or yeast cells at least one isolate having a mutation (e.g., deletion) in its genome.

Thus in one aspect, the present inventors, have developed methods for identifying genetic variants in a population that have altered genetic content that provides them the ability to escape targeting. Here, the target sequence has been modified, and one looks for survivors that have that modification. In some aspects, the modification (i.e., mutation) is a deletion. Further, if the target sequence has been modified, then the wild type genotype is not essential.

Accordingly, in one aspect of the invention a method of screening a population of bacterial cells for essential genes, non-essential genes, and/or expendable genomic islands is provided, comprising: introducing into said population of bacterial cells a heterologous nucleic acid construct comprising a CRISPR array comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of the bacterial cells of said population, thereby producing a population of transformed bacterial cells; and determining the presence or absence of a deletion in the population of transformed bacterial cells, wherein the presence of a deletion in the population of transformed bacterial cells indicates that the target region is comprised within a non-essential gene and/or an expendable genomic island, and the absence of a deletion in the population means that the target region is comprised within an essential gene. A CRISPR array useful with this invention may be Type I, Type II, Type III, Type IV or Type V CRISPR array.

In additional aspects, the invention provides a method of screening a population of bacterial, archaeal, algal or yeast cells for essential genes, non-essential genes, and/or expendable genomic islands, comprising: introducing into the population of bacterial, archaeal, algal or yeast cells: (a) a heterologous nucleic acid construct comprising a trans-activating CRISPR (tracr) nucleic acid, (b) a heterologous nucleic acid construct comprising a CRISPR array (crRNA, crDNA) comprising (5' to 3') a repeat-spacer-repeat sequence or at least one repeat-spacer sequence, wherein the spacer comprises a nucleotide sequence that is substantially complementary to a target region in the genome of the bacterial, archaeal, algal or yeast cells of said population, and (c) a Cas9 polypeptide or a heterologous nucleic acid construct comprising a polynucleotide encoding a Cas9 polypeptide, thereby producing a population of transformed bacterial, archaeal, algal or yeast cells; and determining the presence or absence of a deletion in the population of transformed bacterial, archaeal, algal or yeast cells, wherein the presence of a deletion in the population of transformed bacterial, archaeal or yeast cells means that the target region is comprised within a non-essential gene and/or an expendable genomic island, and the absence of a deletion in the population of transformed bacterial, archaeal, algal or yeast cells means that the target region is comprised within an essential gene.

In other aspects, a method of killing one or more bacterial cells within a population of bacterial cells is provided, comprising: introducing into the population of bacterial cells a heterologous nucleic acid construct comprising a CRISPR array (crRNA, crDNA) comprising a repeat-spacer-repeat sequence or at least one repeat-spacer sequence, wherein the spacer of said repeat-spacer-repeat sequence or at least one repeat-spacer sequence comprises a nucleotide sequence that is substantially complementary to a target region in the genome of the bacterial cells of said population, thereby killing one or more bacterial cells that comprise the target region within the population. A CRISPR array useful with this invention may be Type I, Type II, Type III, Type IV or Type V CRISPR array.

In an additional aspect, a method of killing one or more cells within a population of bacterial, archaeal, algal or yeast cells is provided, the method comprising: introducing into the population of bacterial, archaeal or yeast cells (a) a heterologous nucleic acid construct comprising a trans-activating CRISPR (tracr) nucleic acid, (b) a heterologous nucleic acid construct comprising a CRISPR array (crRNA, crDNA) comprising a repeat-spacer-repeat sequence or at least one repeat-spacer sequence, wherein the spacer of the at least one repeat-spacer sequence and repeat-spacer-repeat sequence comprises a nucleotide sequence that is substantially complementary to a target region in the genome of the bacterial, archaeal, algal or yeast cells of said population, and (c) a Cas9 polypeptide and/or a heterologous nucleic acid construct comprising a polynucleotide encoding a Cas9 polypeptide, thereby killing one or more cells that comprise the target region in their genome within the population of bacterial, archaeal, algal or yeast cells.

Transformation of bacterial genome-targeting CRISPR RNAs can be used to selectively kill bacterial cells on a sequence-specific basis to subtract genetically distinct sub-populations, thereby enriching bacterial populations lacking the target sequence. This distinction can occur on the basis of the heterogeneous distribution of orthogonal CRISPR-Cas systems within genetically similar populations. Thus, in some embodiments, an CRISPR array that is introduced into a population of cells can be compatible (i.e., functional) with a CRISPR-Cas system in the one or more bacterial cells to be killed but is not compatible (i.e., not functional) with the CRISPR Cas system of at least one or more bacterial cells in the population. For instance, *Escherichia coli* and *Klebsiella pneumoniae* can exhibit either Type I-E or Type I-F CRISPR-Cas systems; *Clostridium difficile* encodes Type I-B systems, and different strains of *S. thermophilus* exhibit both Type II-A and Type I-E systems or just Type II-A systems. Depending on the specific CRISPR RNA transformed into a mixture of bacteria, it can specifically target that subset of the population based on its functional compatibility with its cognate system. This can be applied to diverse species containing endogenous CRISPR-Cas systems such as, but not limited to: *Pseudomonas* spp. (such as: *P. aeruginosa*), *Escherichia* spp. (such as: *E. coli*), *Enterobacter* spp. (such as: *E. cloacae*), *Staphylococcus* spp. (such as: *S. aureus*), *Enterococcus* spp. (such as: *E. faecalis, E. faecium*), *Streptomyces* spp. (such as: *S. somaliensis*), *Streptococcus* spp. (such as: *S. pyogenes*), *Vibrio* spp. (such as: *V. cholerae*), *Yersinia* spp. (such as: *Y. pestis*), *Francisella* spp. (such as: *F. tularensis, F. novicida*), *Bacillus* spp. (such as: *B. anthracia, B. cereus*), *Lactobacillus* spp. (such as: *L. casei, L. reuteri, L. acidophilus, L. rhamnosis*), *Burkholderia* spp. (such as: *B. mallei, B. pseudomallei*), *Klebsiella* spp. (such as: *K. pneumoniae*), *Shigella* spp. (such as: *S. dysenteriae, S. sonnei*), *Salmonella* spp. (such as: *S. enterica*), *Borrelia* spp. (such as: *B. burgdorfieri*), *Neisseria* spp. (such as: *N. meningitidis*), *Fusobacterium* spp. (such as: *F. nucleatum*), *Helicobacter* spp. (such as: *H. pylori*), *Chlamydia* spp. (such as: *C. trachomatis*), *Bacteroides* spp. (such as: *B. fragilis*), *Bartonella* spp. (such as: *B. quintana*), *Bordetella* spp. (such as: *B. pertussis*), *Brucella* spp. (such as: *B. abortus*), *Campylobacter* spp. (such as: *C. jejuni*), *Clostridium* spp. (such as: *C. difficile*), *Bifidobacterium* spp. (such as: *B. infantis*), *Haemophilus* spp. (such as: *H influenzae*), *Listeria* spp. (such as: *L. monocytogenes*), *Legionella* spp. (such as: *L. pneumophila*), *Mycobacterium* spp. (such as: *M. tuberculosis*), *Mycoplasma* spp. (such as: *M. pneumoniae*), *Rickettsia* spp. (such as: *R. rickettsii*), *Acinetobacter* spp. (such as: *A. calcoaceticus, A. baumanii*), *Rumincoccus* spp. (such as: *R. albus*), *Propionibacterium* spp. (such as: *P. freudenreichii*), *Corynebacterium* spp. (such as: *C. diphtheriae*), *Propionibacterium* spp. (such as: *P. acnes*), *Brevibacterium* spp. (such as: *B. iodinum*), *Micrococcus* spp. (such as: *M. luteus*), and/or *Prevotella* spp. (such as: *P. histicola*).

CRISPR targeting can remove specific bacterial subsets on the basis of the distinct genetic content in mixed populations. Support for this claim is presented in examples 4, 5 where Lac⁻ bacteria are selected for while Lac$^k$ are removed from the population. The genetic distinction between the Lac$^k$ and Lac⁻ strains is presented in examples 8 and 10, where sequencing of the surviving clones revealed up to 5.5% difference in genetic content compared to the reference wild-type *S. thermophilus* strain. CRISPR-targeting spacers can thus be tuned to various levels of bacterial relatedness by targeting conserved or divergent genetic sequences. Thus, in some embodiments, the bacterial cells in the population can comprise the same CRISPR Cas system and the introduced CRISPR array thus may be functional in the bacterial population as a whole but the genetic content of the different strains or species that make up the bacterial population is sufficiently distinct such that the target region for the introduced CRISPR array is found only in the one or more bacterial species of the population that is to be killed. This can be applied to diverse species containing endogenous CRISPR-Cas systems such as, but not limited to: *Pseudomonas* spp. (such as: *P. aeruginosa*), *Escherichia* spp. (such as: *E. coli*), *Enterobacter* spp. (such as: *E. cloacae*), *Staphylococcus* spp. (such as: *S. aureus*), *Enterococcus* spp. (such as: *E. faecalis, E. faecium*), *Streptomyces* spp. (such as: *S. somaliensis*), *Streptococcus* spp. (such as: *S. pyogenes*), *Vibrio* spp. (such as: *V. cholerae*), *Yersinia* spp. (such as: *Y. pestis*), *Francisella* spp. (such as: *F. tularensis, F. novicida*), *Bacillus* spp. (such as: *B. anthracis, B. cereus*), *Lactobacillus* spp. (such as: *L. casei, L. reuteri, L. acidophilus, L. rhamnosis*), *Burkholderia* spp. (such as: *B. mallei, B. pseudomallei*), *Klebsiella* spp. (such as: *K. pneumoniae*), *Shigella* spp. (such as: *S. dysenteriae, S. sonnei*), *Salmonella* spp. (such as: *S. enterica*), *Borrelia* spp. (such as: *B. burgdorfieri*), *Neisseria* spp. (such as: *N. meningitidis*), *Fusobacterium* spp. (such as: *F. nucleatum*), *Helicobacter* spp. (such as: *H. pylori*), *Chlamydia* spp. (such as: *C. trachomatis*), *Bacteroides* spp. (such as: *B. fragilis*), *Bartonella* spp. (such as: *B. quintana*), *Bordetella* spp. (such as: *B. pertussis*), *Brucella* spp. (such as: *B. abortus*), *Campylobacter* spp. (such as: *C. jejuni*), *Clostridium* spp. (such as: *C. difficile*), *Bifidobacterium* spp. (such as: *B. infantis*), *Haemophilus* spp. (such as: *H. influenzae*), *Listeria* spp. (such as: *L. monocytogenes*), *Legionella* spp. (such as: *L. pneumophila*), *Mycobacterium* spp. (such as: *M. tuberculosis*), *Mycoplasma* spp. (such as: *M. pneumoniae*), *Rickettsia* spp. (such as: *R. rickettsii*), *Acinetobacter* spp. (such as: *A. calcoaceticus, A. baumanii*), *Ruminococcus* spp. (such as: *R. albus*), *Propionibacterium* spp. (such as: *P. freudenreichii*), *Corynebacterium* spp. (such as: *C. diphtheriae*), *Propionibacterium* spp. (such as: *P. acnes*), *Brevibacterium* spp. (such as: *B. iodinum*), *Micrococcus* spp. (such as: *M. luteus*), and/or *Prevotella* spp. (such as: *P. histicola*).

The extent of killing within a population using the methods of this invention may be affected by the amenability of the particular population to transformation in addition to whether the target region is comprised in a non-essential gene, an essential gene or an expendable island. The extent of killing in a population of bacterial, archaeal or yeast cells can vary, for example, by organism, by genus and species. Accordingly, as used herein "killing" means eliminating 2 logs or more of the cells in a population (1% survival or less). Less than 1 log of killing would be a small reduction in the population; whereas 2-3 logs of killing results in a significant reduction of the population; and more than 3 logs of killing indicates that the population has been substantially eradicated.

In another aspect, a method of identifying a phenotype associated with a bacterial gene is provided, comprising: introducing into a population of bacterial cells a heterologous nucleic acid construct comprising a CRISPR array (crRNA, crDNA) comprising a repeat-spacer-repeat sequence or at least one repeat-spacer sequence, wherein the spacer of the at least one repeat-spacer sequence and repeat-spacer-repeat sequence comprises a nucleotide sequence that is substantially complementary to a target region in the genome of the bacterial cells of said population, wherein the target region comprises at least a portion of an open reading frame encoding a polypeptide or functional nucleic acid, thereby killing the cells comprising the target region and producing a population of transformed bacterial cells without the target region (i.e., surviving cells do not comprise the target region); and (i) analyzing the phenotype of the population of cells, or (ii) growing individual bacterial colonies from the population of transformed bacterial cells and analyzing the phenotype of the individual colonies. A CRISPR array useful with this invention may be Type I, Type II, Type III, Type IV or Type V CRISPR array.

In another aspect, a method of identifying the phenotype of a bacterial, archaeal, algal, or yeast gene is provided, comprising: introducing into a population of bacterial, archaeal, algal or yeast cells (a) a heterologous nucleic acid construct comprising a trans-activating CRISPR (tracr) nucleic acid, (b) a heterologous nucleic acid construct comprising a CRISPR array (crRNA, crDNA) comprising (5' to 3') a repeat-spacer-repeat sequence or at least one repeat-spacer sequence, wherein the spacer comprises a nucleotide sequence that is substantially complementary to a target region in the genome of the bacterial, archaeal, algal or yeast cells of said population, and (c) a Cas9 polypeptide and/or a heterologous nucleic acid construct comprising a polynucleotide encoding a Cas9 polypeptide, thereby killing the bacterial, archaeal, algal or yeast cells comprising the target region and producing a population of transformed bacterial, archaeal, algal or yeast cells without the target region; and (i) analyzing the phenotype of the population of cells, and/or (ii) growing individual bacterial, archaeal, or yeast colonies from the population of transformed bacterial, archaeal, algal or yeast cells; and analyzing the phenotype of the individual colonies.

In some embodiments, the analysis comprises PCR, optical genome mapping, genome sequencing, restriction mapping and/or restriction analysis to identify and characterize the mutation, and complementation analysis and/or phenotypic assays to analyze the phenotype.

In some embodiments of the invention determining the extent of killing or a reduction in a population can comprise any method for determining population number, including, but not limited to, (1) plating the cells and counting the colonies, (2) optical density, (3) microscope counting, (4) most probable number, and/or (5) methylene blue reduction. In some embodiments, 16S rDNA sequencing can be used to profile a composition of mixed populations. This can be done, for example, by purifying DNA from the sample as a whole, and performing either whole-genome shotgun sequencing using high-throughput technologies or, for example, by PCR amplifying the 16S gene and sequencing the products in the same manner. The sequences can then be computationally assigned to certain bacterial taxa. In other embodiments, quantitative PCR methods may also be used to quantify bacterial levels. Such techniques are well known in the art. For example, primers for qPCR can be designed to amplify specifically from a strain species, genus, or group of organisms that share the sequence. Thus, a threshold number (ct) may be used to quantify said organism or group of organisms. In additional embodiments, any bacterial activity (phenotype) specific to the target population may also be used as a metric to determine depletion of a population.

In further embodiments, a method of selecting one or more bacterial cells having a reduced genome size from a population of bacterial cells is provided, comprising: introducing into a population of bacterial cells a heterologous nucleic acid construct comprising a CRISPR array (crRNA, crDNA) comprising (5' to 3') a repeat-spacer-repeat sequence or at least one repeat-spacer sequence, wherein the spacer comprises a nucleotide sequence that is substantially complementary to a target region in the genome of one or more bacterial cells of said population, wherein the cells comprising the target region are killed, thereby selecting one or more bacterial cells without the target region and having a reduced genome size from the population of bacterial cells.

A CRISPR array useful with this invention may be Type I, Type II, Type III, Type IV or Type V CRISPR array.

In some embodiments, a method of selecting one or more bacterial cells having a reduced genome size from a population of bacterial cells, comprising: introducing into a population of bacterial cells: (a)(i) one or more heterologous nucleic acid constructs comprising a nucleotide sequence having at least 80 percent identity to at least 300 consecutive nucleotides present in the genome of said bacterial cells, or (ii) two or more heterologous nucleic acid constructs comprising at least one transposon, thereby producing a population of transgenic bacterial cells comprising a non-natural site for homologous recombination between the one or more heterologous nucleic acid constructs integrated into the genome and the at least 300 consecutive nucleotides present in the genome, or between a first and a second transposon integrated into the genome; and (b) a heterologous nucleic acid construct comprising a CRISPR array (crRNA, crDNA) comprising (5' to 3') a repeat-spacer-repeat sequence or at least one repeat-spacer sequence, wherein the spacer of said repeat-spacer-repeat sequence or at least one repeat-spacer sequence comprises a nucleotide sequence that is substantially complementary to a target region in the genome of one or more bacterial cells of said population, the target region is located between the one or more heterologous nucleic acid constructs introduced into the genome, and the at least 300 consecutive nucleotides present in the genome and/or between the first transposon and second transposon, wherein cells comprising the target region are killed and cells not comprising the target region survive, thereby selecting one or more bacterial cells without the target region and having a reduced genome size from the population of transgenic bacterial cells. A CRISPR array useful with this invention may be Type I, Type II, Type III, Type IV or Type V CRISPR array.

As is well known in the art, transposons can be created via, for example, PCR amplification or through designed DNA synthesis, and may be introduced via any method of transformation.

In some embodiments, the invention provides a method of selecting one or more bacterial, archaeal, algal or yeast cells having a reduced genome size from a population of bacterial, archaeal, algal or yeast cells, comprising: introducing into a population of bacterial, archaeal or yeast cells (a) a heterologous nucleic acid construct comprising a trans-activating CRISPR (tracr) nucleic acid, (b) a heterologous nucleic acid construct comprising a CRISPR array (crRNA, crDNA) comprising a repeat-spacer-repeat sequence or at least one repeat-spacer sequence, wherein the spacer of the at least one repeat-spacer sequence and the at least one repeat-spacer-repeat sequence comprises a nucleotide sequence that is substantially complementary to a target region in the genome of the bacterial, archaeal, algal or yeast cells of said population, and (c) a Cas9 polypeptide and/or a heterologous nucleic acid construct comprising a polynucleotide encoding a Cas9 polypeptide, wherein cells comprising the target region are killed, thereby selecting one or more bacterial, archaeal, algal or yeast cells without the target region and having a reduced genome size from the population of bacterial, archaeal, algal or yeast cells.

In other embodiments, a method of selecting one or more bacterial, archaeal, algal or yeast cells having a reduced genome size from a population of bacterial, archaeal, algal or yeast cells is provided, comprising: introducing into a population of bacterial, archaeal, algal or yeast cells: (a)(i) one or more heterologous nucleic acid constructs comprising a nucleotide sequence having at least 80 percent identity to at least 300 consecutive nucleotides present in the genome of said bacterial, archaeal, algal or yeast cells, or (ii) two or more heterologous nucleic acid constructs comprising at least one transposon, thereby producing a population of transgenic bacterial, archaeal, algal or yeast cells comprising a non-natural site for homologous recombination between the one or more heterologous nucleic acid constructs integrated into the genome and the at least 300 consecutive nucleotides present in the genome, or between a first and a second transposon integrated into the genome; and (b)(i) a heterologous nucleic acid construct comprising a trans-activating CRISPR (tracr) nucleic acid, (ii) a heterologous nucleic acid construct comprising a CRISPR array (crRNA, crDNA) comprising a repeat-spacer-repeat sequence or at least one repeat-spacer sequence, wherein the spacer of the at least one repeat-spacer sequence or the at least one repeat-spacer-repeat sequence comprises a nucleotide sequence that is substantially complementary to a target region in the genome of one or more bacterial, archaeal, algal or yeast cells of said population, and (iii) a Cas9 polypeptide and/or a heterologous nucleic acid construct comprising a polynucleotide encoding a Cas9 polypeptide, wherein the target region is located between the one or more heterologous nucleic acid constructs incorporated into the genome, and the at least 300 consecutive nucleotides present in the genome and/or between the first transposon and second transposon, wherein cells comprising the target region are killed and cells not comprising the target region survive, thereby selecting one or more bacterial, archaeal, algal or yeast cells without the target region and having a reduced genome size from the population of transgenic bacterial, archaeal, algal or yeast cells.

In some aspects, the reduced genome size may be reduced as compared to a control. In some aspects, a control may be a wild-type population of bacterial, archaeal, algal or yeast cells, or a population of bacterial, archaeal, algal or yeast cells transformed with a heterologous construct comprising a CRISPR array (e.g., a Type I, Type II, Type III, Type IV or Type V CRISPR array) comprising a repeat-spacer-repeat sequence or at least one repeat-spacer sequence, wherein the spacer of said repeat-spacer-repeat sequence or said at least one repeat-spacer sequence comprises a nucleotide sequence that is not complementary to a target region in the genome of the bacterial, archaeal, algal or yeast cells of said population (i.e., non-self targeting/"scrambled spacer"). In additional aspects, a control may be a population of bacterial, archaeal, algal or yeast cells transformed with a heterologous construct comprising a CRISPR array comprising a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of the bacterial, archaeal, algal or yeast cells of said population but lacks a protospacer adjacent motif (PAM).

In some embodiments, a method of identifying in a population of bacteria at least one isolate having a deletion in its genome (e.g., a chromosomal and/or plasmid deletion) is provided, comprising: introducing into a population of bacterial cells a heterologous nucleic acid construct comprising a CRISPR array (crRNA, crDNA) comprising (5' to 3') a repeat-spacer-repeat sequence or at least one repeat-spacer sequence, wherein the spacer of said repeat-spacer-repeat sequence or said at least one repeat-spacer sequence comprises a nucleotide sequence that is substantially complementary to a target region in the genome of one or more bacterial cells of said population and cells comprising the target region are killed, thereby producing a population of transformed bacterial cells without the target region; and growing individual bacterial colonies from the population of transformed bacterial cells, thereby identifying at least one isolate from the population of transformed bacteria having a deletion in its genome. A CRISPR array useful with this invention may be Type I, Type II, Type III, Type IV or Type V CRISPR array.

In additional embodiments, the invention provides a method of identifying in a population of bacteria at least one isolate having a deletion in its genome, comprising: introducing into the population of bacterial cells: (a)(i) one or more heterologous nucleic acid constructs comprising a nucleotide sequence having at least 80 percent identity to at least 300 consecutive nucleotides present in the genome of said bacterial cells, or (ii) two or more heterologous nucleic acid constructs comprising at least one transposon, thereby producing a population of transgenic bacterial cells comprising a non-natural site for homologous recombination between the one or more heterologous nucleic acid constructs integrated into the genome and the at least 300 consecutive nucleotides present in the genome, or between a first and a second transposon integrated into the genome; and b) a heterologous nucleic acid construct comprising a CRISPR array (crRNA, crDNA) comprising a repeat-spacer-repeat sequence or at least one repeat-spacer sequence, wherein the spacer comprises a nucleotide sequence that is substantially complementary to a target region in the genome of one or more bacterial cells of said population, wherein the target region is located between the one or more heterologous nucleic acid constructs introduced into the genome and the at least 300 consecutive nucleotides present in the genome and/or between the first transposon and second transposon, and cells comprising the target region are killed [and cells not comprising the target region survive], thereby producing a population of transformed bacterial cells without the target region; and growing individual bacterial colonies from the population of transformed bacterial cells, thereby identifying at least one isolate from the population of bacteria having a deletion in its genome. A CRISPR array useful with this invention may be Type I, Type II, Type III, Type IV or Type V CRISPR array.

In further embodiments, a method of identifying in a population of bacterial, archaeal, algal or yeast cells at least one isolate having a deletion in its genome is provided, comprising: introducing into a population of bacterial, archaeal, algal or yeast cells: (a) a heterologous nucleic acid construct comprising a trans-activating CRISPR (tracr) nucleic acid; (b) a heterologous nucleic acid construct comprising a CRISPR array (crRNA, crDNA) comprising a repeat-spacer-repeat sequence or at least one repeat-spacer sequence, wherein the spacer of said repeat-spacer-repeat sequence or at least one repeat-spacer sequence comprises a nucleotide sequence that is substantially complementary to a target region in the genome (e.g., chromosomal, mitochondrial and/or plasmid genome) of the bacterial, archaeal, algal or yeast cells of said population; and (c) a Cas9 polypeptide or a heterologous nucleic acid construct comprising a polynucleotide encoding a Cas9 polypeptide, wherein cells comprising the target region are killed, thereby producing a population of transformed bacterial, archaeal, algal or yeast cells without the target region; and growing individual bacterial, archaeal or yeast colonies from the population of transformed bacterial, archaeal, algal or yeast cells, thereby identifying at least one isolate from the population of transformed bacterial, archaeal, algal or yeast cells having a deletion in its genome.

In still further embodiments, the invention provides a method of identifying in a population of bacterial, archaeal, algal or yeast cells at least one isolate having a deletion in its genome, comprising: introducing into the population of bacterial, archaeal, algal or yeast cells: (a)(i) one or more heterologous nucleic acid constructs comprising a nucleotide sequence having at least 80 percent identity to at least 300 consecutive nucleotides present in the genome of said bacterial, archaeal, algal or yeast cells, or (ii) two or more heterologous nucleic acid constructs comprising at least one transposon, thereby producing a population of transgenic bacterial, archaeal, algal or yeast cells comprising a non-natural site for homologous recombination between the one or more heterologous nucleic acid constructs integrated into the genome and the at least 300 consecutive nucleotides present in the genome, or between a first and a second transposon integrated into the genome; and (b)(i) a heterologous nucleic acid construct comprising a trans-activating CRISPR (tracr) nucleic acid, (ii) a heterologous nucleic acid construct comprising a CRISPR array (crRNA, crDNA) comprising a repeat-spacer-repeat sequence or at least one repeat-spacer sequence, wherein the spacer comprises a nucleotide sequence that is substantially complementary to a target region in the genome of one or more bacterial, archaeal, algal or yeast cells of said population; and (iii) a Cas9 polypeptide and/or a heterologous nucleic acid construct comprising a polynucleotide encoding a Cas9 polypeptide, wherein the target region is located between the one or more heterologous nucleic acid constructs incorporated into the genome and the at least 300 consecutive nucleotides present in the genome and/or between the first transposon and second transposon, and cells comprising the target region are killed and cells not comprising the target region survive, thereby producing a population of transformed bacterial, archaeal, algal or yeast cells without the target region; and growing individual bacterial, archaeal or yeast colonies from the population of transformed bacterial, archaeal, algal or yeast cells, thereby identifying at least one isolate from the population having a deletion in its genome.

In some embodiments, fitness/growth rate can be increased by reducing genome size or by deleting select genes (encoding polypeptides or functional nucleic acids (e.g., transcriptional regulators)) that require high energy input for transcription and translation. Thus, in some embodiments, a method of increasing the fitness or growth rate of a population of bacterial, archaeal, algal or yeast cells is provided, comprising: selecting for a reduced genome size (e.g., selecting for the absence of a portion of the genome) and/or deletion in the genomes of the bacterial, archaeal, algal or yeast cells of the populations as described herein. In some embodiments, the deletion may comprise one gene or more than one gene. Therefore, through reducing the genome size or deleting a particular gene or genes, the cells of the population no longer expend energy on the transcription/translation of the portion of the genome that is absent or the deleted gene or genes, thereby having reduced energy needs and increased fitness as compared to a control population still comprising said portion of the genome and/or said gene or genes.

In other embodiments, a method of increasing the amount of a product produced from a population of bacterial, archaeal, algal or yeast cells is provided, comprising increasing the fitness or growth rate of the cell by selecting for a deletion in the genomes of the bacterial, archaeal, algal or yeast cells as described herein. In some embodiments, the products can include, but are not limited to, antibiotics, secondary metabolites, vitamins, proteins, enzymes, acids, and pharmaceuticals.

In some embodiments, a CRISPR array (crRNA, crDNA) useful with this invention may be an array from any Type I CRISPR-Cas system, Type II CRISPR-Cas system, Type III CRISPR-Cas system, Type IV CRISPR-Cas system, or a Type V CRISPR-Cas system.

With regard to the preceding embodiments, a heterologous nucleic acid construct comprising a tracr nucleic acid and a heterologous nucleic acid construct comprising a CRISPR array may be comprised in and introduced in the same construct (e.g., expression cassette or vector) or in different constructs. In particular embodiments, a heterologous nucleic acid construct comprising a tracr nucleic acid and a heterologous nucleic acid construct comprising a CRISPR array may be comprised in single construct (e.g., expression cassette and/or vector) that may optionally further comprise a polynucleotide encoding Cas9 polypeptide. In some embodiments, the heterologous nucleic acid construct comprising a tracr nucleic acid and the heterologous nucleic acid construct comprising a CRISPR array may be operably linked to a single promoter and/or to separate promoters.

In some embodiments, a heterologous nucleic acid construct comprising a trans-activating CRISPR (tracr) nucleic acid and a heterologous nucleic acid construct comprising a CRISPR array (crRNA, crDNA) may be comprised in a CRISPR guide (gRNA, gDNA). In some embodiments, a CRISPR guide may be operably linked to a promoter.

In some embodiments, a Cas9 polypeptide useful with this invention comprises at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence of a Cas9 nuclease. Exemplary Cas9 nucleases useful with this invention can be any Cas9 nuclease known to catalyze DNA cleavage in a CRISPR-Cas system. As known in the art, such Cas9 nucleases comprise a HNH motif and a RuvC motif (See, e.g., WO2013/176772; WO/2013/188638). In some embodiments, a functional fragment of a Cas9 nuclease can be used with this invention.

CRISPR-Cas systems and groupings of Cas9 nucleases are well known in the art and include, for example, a *Streptococcus thermophilus* CRISPR 1 (Sth CR1) group of Cas9 nucleases, a *Streptococcus thermophilus* CRISPR 3 (Sth CR3) group of Cas9 nucleases, a *Lactobacillus buchneri* CD034 (Lb) group of Cas9 nucleases, and a *Lactobacillus rhamnosus* GG (Lrh) group of Cas9 nucleases. Additional Cas9 nucleases include, but are not limited to, those of *Lactobacillus curvatus* CRL 705. Still further Cas9 nucleases useful with this invention include, but are not limited to, a Cas9 from *Lactobacillus animalis* KCTC 3501, and *Lactobacillus farciminis* WP 010018949.1.

Furthermore, in particular embodiments, the Cas9 nuclease can be encoded by a nucleotide sequence that is codon optimized for the organism comprising the target DNA. In still other embodiments, the Cas9 nuclease can comprise at least one nuclear localization sequence.

In some embodiments, a Type I polypeptide useful with this invention comprises at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence of a Cas3, Cas3' nuclease, a Cas3" nuclease, fusion variants thereof. In some embodiments, a Type I Cascade polypeptide useful with this invention comprises at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence of a Cas7 (Csa2), Cas8a1 (Csx13), Cas8a2 (Csx9), Cas5, Csa5, Cas6a, Cas6b, Cas8b (Csh1), Cas7 (Csh2), Cas5, Cas5d, Cas8c (Csd1), Cas7 (Csd2), Cas10d (Csc3), Csc2, Csc1, Cas6d, Cse1 (CasA), Cse2 (CasB), Cas7 (CasC), Cas5 (CasD), Cas6e (CasE), Cys1, Cys2, Cas7 (Cys3), Cas6f (Csy4), Cas6 and/or Cas4

Type I CRISPR-Cas systems are well known in the art and include, for example, *Archaeoglobus fulgidus* comprises an exemplary Type I-A CRISPR-Cas system, *Clostridium kluyveri* DSM 555 comprises an exemplary Type I-B CRISPR-Cas system, *Bacillus halodurans* C-125 comprises an exemplary Type I-C CRISPR-Cas system, *Cyanothece* sp. PCC 802 comprises an exemplary Type I-D CRISPR-Cas system, *Escherichia coli* K-12 comprises an exemplary Type I-E CRISPR-Cas system, *Geobacter sulfurreducens* comprises an exemplary Type I-U CRISPR-Cas system and *Yersinia pseudotuberculosis* YPIII comprises an exemplary Type I-F CRISPR-Cas system.

In some embodiments, a Type II polypeptide useful with this invention comprises at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence of a Cas9. Type II CRISPR-Cas systems well known in the art and include, for example, *Legionella pneumophila* str. Paris, *Streptococcus thermophilus* CNRZ1066 and *Neisseria lactamica* 020-06.

In some embodiments, a Type III polypeptide useful with this invention comprises at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence of a Cas6, Cas10 (or Csm1), Csm2, Csm3, Csm4, Csm5, and Csm6, Cmr1, Cas10 (or Cmr2), Cmr3, Cmr4, Cmr5, and Cmr6, Cas7, Cas10, Cas7 (Csm3), Cas5 (Csm4), Cas7 (Csm5), Csm6, Cas7 (Cmr1), Cas5 (Cmr3), Cas7 (Cmr4), Cas7 (Cmr6), Cas7 (Cmr6), Cmr5, Cas5 (Cmr3), Cas5 (Csx10), Csm2, Cas7 (Csm3), and a111473. Type III CRISPR-Cas systems are well known in the art and include, for example, Staphylococcus epidermidis RP62A, which comprises an exemplary Type III-A CRISPR-Cas system, Pyrococcus furiosus DSM 3638, which comprises an exemplary Type III-B CRISPR-Cas system, *Methanothermobacter thermautotrophicus* str. Delta H, which comprises an exemplary Type III-C CRISPR-Cas system, and *Roseiflexis* sp. Rs-1, which comprises an exemplary Type III-D CRISPR-Cas system.

In some embodiments, a Type IV polypeptide useful with this invention comprises at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence of a Csf4 (dinG), Csf1, Cas7 (Csf2) and/or Cas5 (csf3). Type IV CRISPR-Cas systems are well known in the art, for example, *Acidithiobacillus ferrooxidans* ATCC 23270 comprises an exemplary Type IV CRISPR-Cas system.

In some embodiments, a Type V polypeptide useful with this invention comprises at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence of a Cpf1, Cas1, Cas2, or Cas4. Type V CRISPR-Cas systems are well known in the art and include, for example, *Francisella* cf *novicida* Fx1 comprises an exemplary Type V CRISPR-Cas system.

Additionally provided herein are expression cassettes and vectors comprising the nucleic acid constructs, the nucleic acid arrays, nucleic acid molecules and/or the nucleotide sequences of this invention, which can be used with the methods of this disclosure.

In further aspects, the nucleic acid constructs, nucleic acid arrays, nucleic acid molecules, and/or nucleotide sequences of this invention can be introduced into a cell of a host organism. Any cell/host organism for which this invention is useful with can be used. Exemplary host organisms include bacteria, archaea, algae and fungi (e.g., yeast).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Bacterial Strains

All bacterial strains are listed in Table 1. Bacterial cultures were cryopreserved in an appropriate growth medium with 25% glycerol (vol/vol) and stored at −80° C. *S. thermophilus* was propagated in Elliker media (Difco) supplemented with 1% beef extract (wt/vol) and 1.9% (wt/vol) β-glycerolphosphate (Sigma) broth under static aerobic conditions at 37° C., or on solid medium with 1.5% (wt/vol) agar (Difco), incubated anaerobically at 37° C. for 48 hours. Concentrations of 2 μg/mL of erythromycin (Em) and 5 μg/mL of chloramphenicol (Cm) (Sigma) were used for plasmid selection in *S. thermophilus*, when appropriate. *E. coli* EC1000 was propagated aerobically in Luria-Bertani (Difco) broth at 37° C., or on brain-heart infusion (BHI) (Difco) solid medium supplemented with 1.5% agar. Antibiotic selection of *E. coli* was maintained with 40 μl g/mL kanamycin (Kn) and 150 μg/mL of Em for recombinant *E. coli*, when appropriate. Screening of *S. thermophilus* derivatives for β-galactosidase activity was assessed qualitatively by supplementing a synthetic Elliker medium with 1% lactose, 1.5% agar, and 0.04% bromo-cresol purple as a pH indicator.

Example 2. DNA Isolation and Cloning

All kits, enzymes, and reagents were used according to the manufacturers' instructions. DNA purification and cloning were performed as described previously (41). Briefly, purification of genomic DNA from *S. thermophilus* employed a ZR Fungal/Bacterial MiniPrep kit (Zymo). Plasmid DNA was isolated from *E. coli* using Qiagen Spin miniprep kit (Qiagen). High fidelity PCR amplification of DNA was performed with PFU HS II DNA polymerase (Stratagene). Routine PCRs were conducted with Choice-Taq Blue polymerase (Denville). Primers for PCR amplification were purchased from Integrated DNA Technologies (Coralville, Iowa). DNA extraction from agarose gels was performed with a Zymoclean DNA gel recovery kit (Zymo). Restriction endonucleases were acquired from Roche Molecular Biochemicals. Ligations were performed with New England Biolabs quick T4 ligase. Sequencing was performed by Davis Sequencing Inc. (Davis, Calif.). Cryopreserved rubidium chloride competent *E. coli* cells were prepared as previously described (41). Plasmids with lacZ targeting arrays were constructed with each consisting sequentially of the (1) native leader sequence specific to SthCRISPR1 or SthCRISPR3 (2) native repeats specific to CRISPR 1 or CRISPR 3 (3) spacer sequence specific to the 5' end of lacZ (4) another native repeat (FIG. 1). In order to engineer each plasmid, the sequence features listed above were ordered as extended oligomers (Table 2), combined using splicing by overlap extension PCR (42) and cloned into pORI28 (FIG. 2).

Example 3. Selection and Design of CRISPR Spacers

The programmable specificity of chromosomal cleavage hinges upon selection of a desired spacer sequence unique to the target allele. Specificity is further compounded by the requisite PAM, a short conserved sequence that must be proximate to the proto-spacer in the target sequence (21, 43). Thus, strict criteria for selection and design of spacers were the location of consensus PAM sequences and incidental sequence identity to extraneous genomic loci. Putative protospacers were constrained by first defining the location of all putative PAM sequences in the sense and antisense strands of lacZ. Within the 3,081 nt gene, there were 22 CRISPR1 (AGAAW) and 39 CRISPR3 (GGNG) PAM sites that were identical to their bioinformatically derived consensus sequences (21). After potential spacers were identified, the complete proto-spacer, seed, and PAM sequence were subjected to BLAST analysis against the genome of *S. thermophilus* LMD-9 to prevent additional targeting of non-specific loci. The spacers for CRISPR1 and CRISPR3 were disparate in sequence and corresponding PAM sites, but were designed to target the 5' end of lacZ, resulting in predicted cleavage sites residing 6 nt apart. Therefore, the leader sequences, repeats, and spacers on each plasmid represented orthogonal features unique to CRISPR1 or CRISPR3, respectively. To assess target locus-dependent mutations, an additional CRISPR3 plasmid was created with a spacer to the metal cation-binding residue essential for β-galactosidase activity. A CRISPR1 array plasmid containing a non-self-spacer was used as a control to quantify lethality of self-targeting.

Example 4. Transformation

Plasmids were electroporated into competent *S. thermophilus* containing the temperature-sensitive helper plasmid, pTRK669, according to methods described previously (44). Briefly, an overnight culture of *S. thermophilus* was inoculated at 1% (vol/vol) into 50 mL of Elliker medium supplemented with 1% beef extract, 1.9% β-glycerophosphate and Cm selection. When the culture achieved an $OD_{600}$ nm of 0.3, penicillin G was added to achieve a final concentration of 10 μg/mL, in order to promote electroporation efficiency (45). Cells were harvested by centrifugation and washed 3× in 10 mL cold electroporation buffer (1 M sucrose and 3.5 mM $MgCl_2$). The cells were concentrated 100-fold in electroporation buffer and 40 μL of the suspension was aliquoted into 0.1 mm electroporation cuvettes. Each suspension was combined with 700 ng of plasmid. Electroporation conditions were set at 2,500 V, 25 μFd capacitance, and 200 Ohms resistance. Time constants were recorded and ranged from 4.4 to 4.6 ms. The suspensions were immediately combined with 950 μL of recovery medium and incubated for 8 hours at 37° C. Cell suspensions were plated on selective medium and electroporation cuvettes were washed with medium to ensure recovery of cells.

Example 5. β-Galactosidase Phenotype Confirmation

Transformants generated from both CRISPR1 and CRISPR3 were initially screened for the β-galactosidase deficient phenotype by restreaking colonies on semi-synthetic Elliker medium supplemented with 1% lactose as the sold carbohydrate source. Loss of β-galactosidase activity was confirmed by performing Miller assays (o-nitrophenyl-β-D-galactoside (ONPG) (46). Briefly, cultures were propagated to late-log phase ($OD_{600}$ nm of 1.2) in 5 mL of medium and harvested by centrifugation (4,000×g for 10 min). Cells were washed and resuspended in 0.5 mL phosphate-buffered saline (Gibco-Invitrogen). Each suspension was combined with 100 uL of 0.1 mm glass beads (Biospec) and then subjected to five 60 s cycles of homogenization in a Mini-Beadbeater (Biospec). Samples were then centrifuged (15,000×g for 5 min) to remove debris and intact cells. Cell lysates (10 µL aliquots) were combined with 600 µL of substrate solution (60 mM $Na_2HPO_4$; 40 mM $NaH_2PO_4$; 1 mg/mL ONPG; 2.7 µL/mL β-mercaptoethanol) and incubated for 5 min at room temperature, at which point 700 µL stop solution was added (1 M $NaCO_3$). The absorbance at 420 nm was recorded and activity of β-galactosidase was reported as Miller units, calculated as previously described (46).

Example 6. Growth and Activity Assessment

Cultures were preconditioned for growth assays by subculturing for 12 generations in a semi-synthetic Elliker medium deficient in lactose. Fresh medium was inoculated with an overnight culture at 1% (vol/vol) and incubated at 37° C. statically. $OD_{600}$ monitored hourly until the cultures achieved stationary phase. Acidification of milk was assessed by inoculating skim milk with an overnight culture to a level of $10^8$ cfu/mL and incubating at 42° C. The pH was subsequently monitored using a Mettler Toledo Seven Easy pH meter and Accumet probe. Skim milk was acquired from the NCSU Dairy plant and Pasteurized for 30 min at 80° C.

Example 7. Identification of Expendable Genomic Regions

Figure 3A:
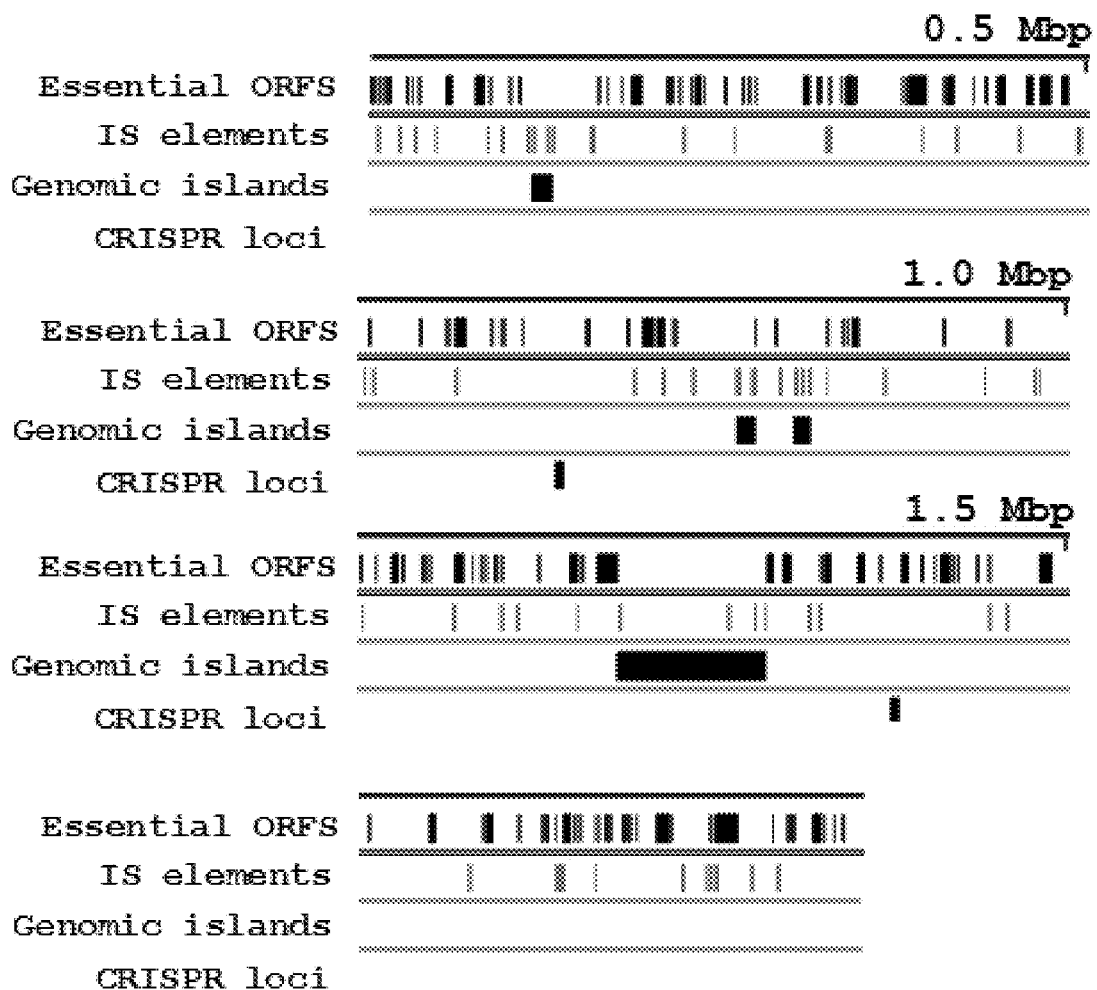
FIGS. 3A-3B show a map of essential genes, insertion sequences and genomic islands. (A) The location and distribution of putative essential ORFs (top row), insertion sequences ($2^{nd}$ row) and putative genomic islands ($3^{rd}$ row). Potential targets for CRISPR-Cas ($4^{th}$ row) mediated deletion were identified by mapping transposable elements of various families within the genome of Streptococcus thermophilus LMD-9. Genetic organization of putative genomic islands and the protospacer/PAM combinations corresponding to each. (B) provides four panels. The upper panel provides Genomic island 1, encoding an oligopeptide transport system (SEQ ID NO:6). The second panel from the top provides Genomic island 2, containing the cell-envelope proteinase PrtS (SEQ ID NO:7). The third panel from the top provides Genomic island 3, encoding an ATPase copper-efflux protein (SEQ ID NO:8) and the bottom panel provides the. (E) The genomic island encoding selected ORFs including the Lac operon (from left to right, SEQ ID NO:9, SEQ ID NO:10, SEQ ID NO:11.

In silico prediction of mobile and expendable loci for CRISPR-Cas targeting was performed on the basis of i) location, orientation, and nucleotide identity of IS elements, and ii) location of essential ORFs. In Bacillus subtilis, 271 essential ORFs were identified by determining the lethality of genome-wide gene knockouts (33). The S. thermophilus genome was queried for homologues to each essential gene from B. subtilis using the BLASTp search tool under the default scoring matrix for amino acid sequences. Homologues to about 239 essential ORFs were identified in S. thermophilus, all of which were chromosomally encoded (Table 4). Proteins involved in conserved cellular processes including DNA replication/homeostasis, translation machinery, and core metabolic pathways were readily identified. No homologues corresponding to cytochrome biosynthesis/respiration were observed, in accordance with the metabolic profile of fermentative bacteria. Each putative essential ORF was mapped to the reference genome using SnapGene software, facilitating visualization of their location and distribution in S. thermophilus LMD-9 (FIG. 3A).

Figure 4:
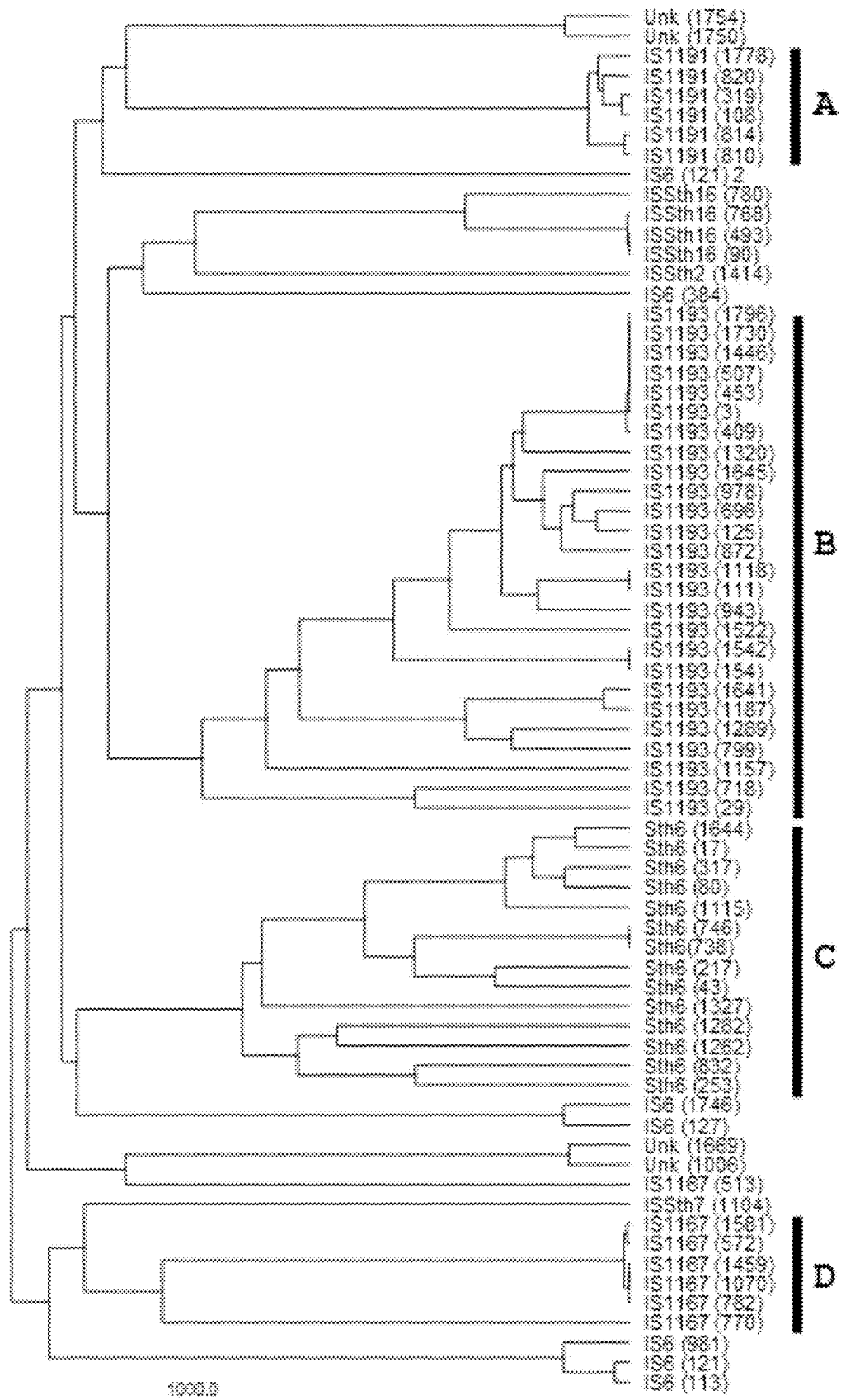
FIG. 4 provides a dendrogram of transposon coding sequences distributed throughout the genome of S. thermophilus LMD-9. The alignment was created using the Geneious® Software. The letters A, B, C, and D correspond to alignments in FIG. 5 for each family.

IS elements within the S. thermophilus genome were grouped by aligning transposon coding sequences using Geneious® software (FIG. 4). Family designations were determined according to BLAST analysis within the IS element database. To predict the potential for recombination-mediated excision of chromosomal segments, the relative location of related IS elements were mapped to the S. thermophilus genome (FIG. 3A). The IS1193 and Sth6 families of IS elements appeared most frequently in the genome and are commonly found in Streptococcus pneumoniae and Streptococcus mutans (34). Despite the prevalence of IS1193 elements, many of these loci were shown to be small fragments that exhibited some polymorphism and degeneracy, but there were also several copies present with a high level of sequence identity (FIG. 5A). In contrast, the Sth6 family exhibited considerable polymorphism and high degeneracy, with some copies harboring significant internal deletions (FIG. 5B). IS1167 and IS1191 elements were less frequent but exhibited near perfect fidelity between the copies identified in the genome (FIGS. 5C and 5D). Based on the conservation of length and sequence of the IS1167 and IS1191 elements of S. thermophilus, and their relative proximity to milk adaptation genes, we postulate that these conserved/high fidelity transposons were recently acquired in the genome.

Figure 3B:
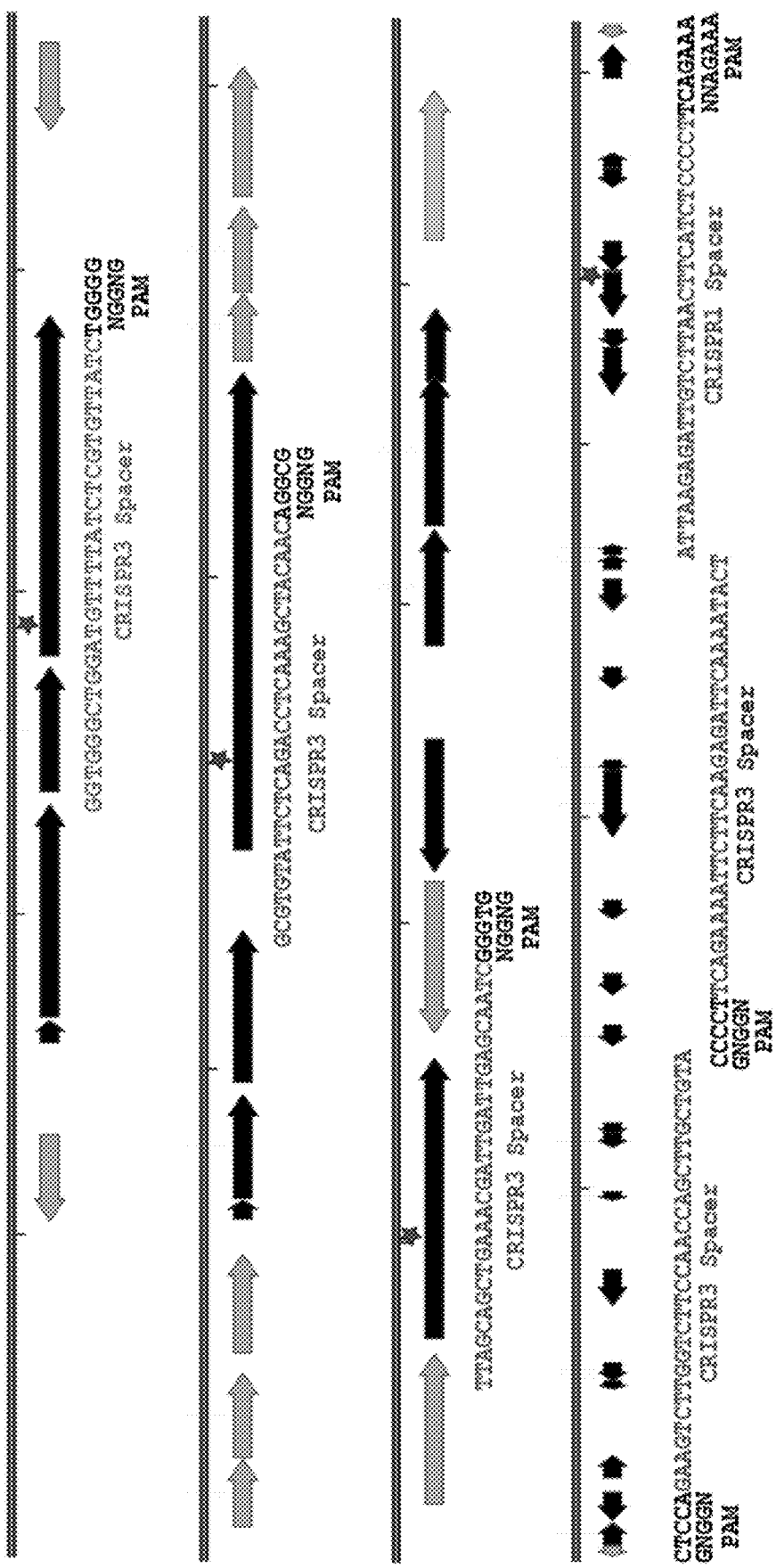

By combining the location of predicted essential ORFs and IS elements, expendable islands flanked by IS elements of high fidelity were identified (FIG. 3A) (Table 3). The first island contained an operon unique to S. thermophilus LMD-9, encoding a putative ATP-dependent oligonucleotide transport system with unknown specificity (FIG. 3B) (35). The second harbors the cell-envelope proteinase PrtS which contributes to the fast-acidification phenotype of S. thermophilus (FIG. 3B)(36). Notably, while prtS is not ubiquitous in S. thermophilus genomes, it has been demonstrated that the genomic island encoding prtS is transferable between strains using natural competence (36). The third island contains a putative ATP-dependent copper efflux protein and is present in every sequenced S. thermophilus strain (FIG. 3B). The fourth island is the largest by far in terms of length at 102 kbp, and gene content, with 102 predicted ORFs including the lac operon (FIG. 3B). This island is found in all strains of S. thermophilus, but the specific gene content and length varies among strains. In order to determine the outcome of targeting a large genomic island with both endogenous Type II systems, repeat-spacer arrays were generated for the lacZ coding sequence (FIG. 3B) and cloned into pORI28 (FIG. 2). The fourth island was selected for CRISPR-Cas targeting due to its size, ubiquity in S. thermophilus strains, and the ability to screen for lacZ mutations on the basis of a β-galactosidase negative phenotype.

Example 8. CRISPR-Cas Targeting of lacZ Selects for Large Deletion Events

Figure 6A:
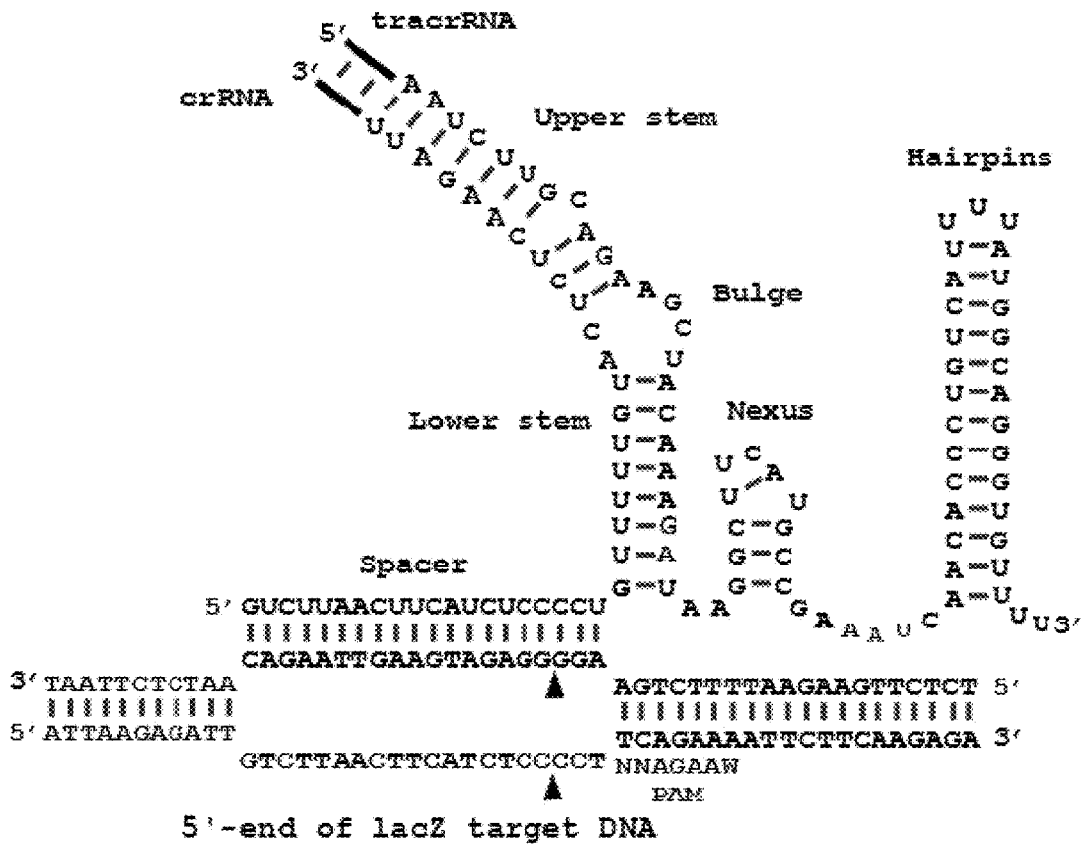
FIG. 6A-6C show the structural basis for and apparent cytotoxicity of DNA targeting by CRISPR-Cas9. Spacer sequences for SthCRISPR1 (crRNA:SEQ ID NO:12; tracrRNA:SEQ ID NO:13; 5' end of LacZ target DNA, upper strand: SEQ ID NO:15; lower strand: SEQ ID NO:14)(A) and SthCRISPR3 (crRNA:SEQ ID NO:16; tracrRNA:SEQ ID NO:17; 5' end of LacZ target DNA, upper strand: SEQ ID NO:19; lower strand: SEQ ID NO:18) (B) for targeting lacZ. Cas9 interrogates DNA and binds reversibly to PAM sequences with stabilization of Cas9 at the target occurring via formation of the tracrRNA::crRNA duplex. Activation of the Cas9 causes simultaneous cleavage of each strand by the RuvC and HNH domains, as denoted by black wedges. Transformants recovered following electroporation of control and self-targeting plasmids (C). Average clones±SD screened across independent transformation experiments (n=4) for each of the plasmids tested.
Figure 6B:
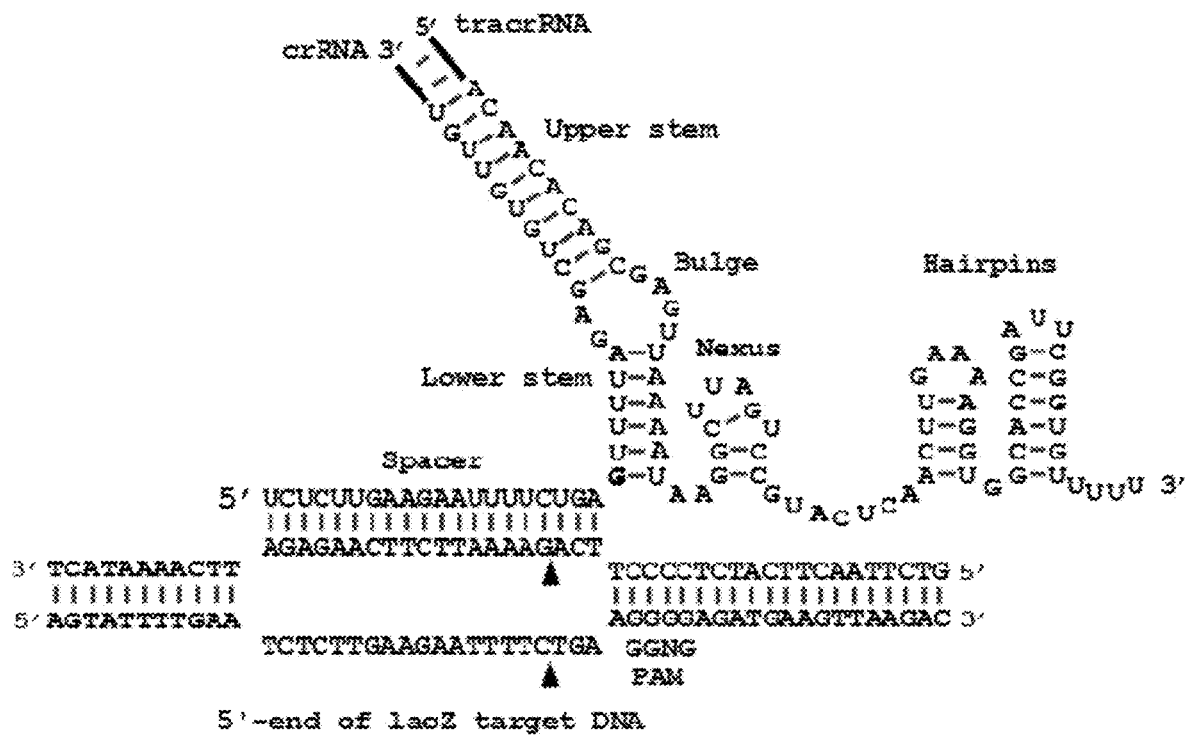
Figure 14A:
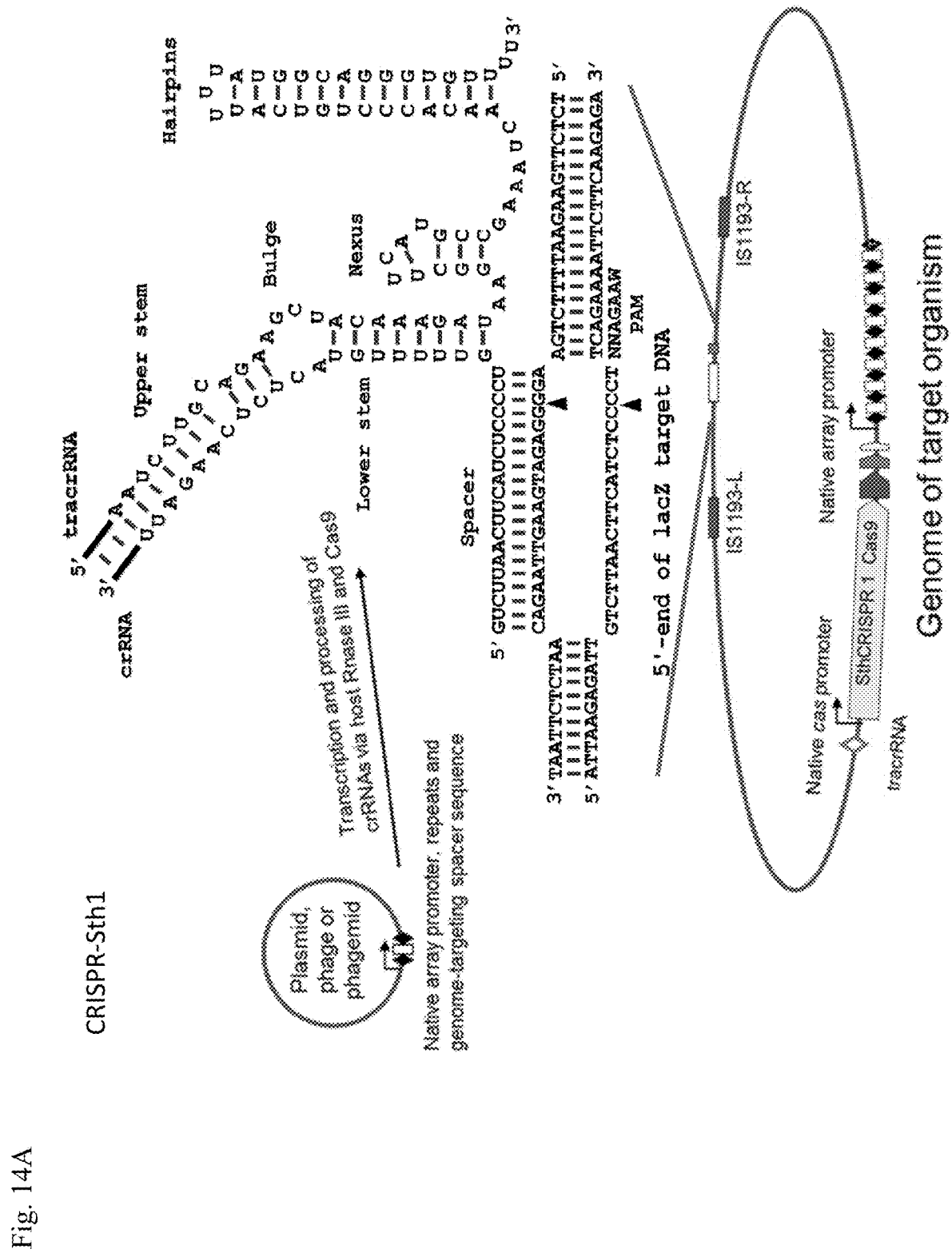
FIG. 14A-14B shows introduction of an exogenous phage, plasmid or phagemid encoding CRISPR arrays (Type II system) to co-opt endogenous systems for programmed cell death in *Streptococcus thermophiles*. (A) CRISPR-Sth1 (crRNA:EQ ID NO:12; tracrRNA:SEQ ID NO:13; 5' end of LacZ target DNA, upper strand: SEQ ID NO:15; lower strand: SEQ ID NO:14) and (B) SthCRISPR3 (crRNA:SEQ ID NO:16; tracrRNA:SEQ ID NO:17; 5' end of LacZ target DNA, upper strand: SEQ ID NO:19; lower strand: SEQ ID NO:18).
Figure 14B:
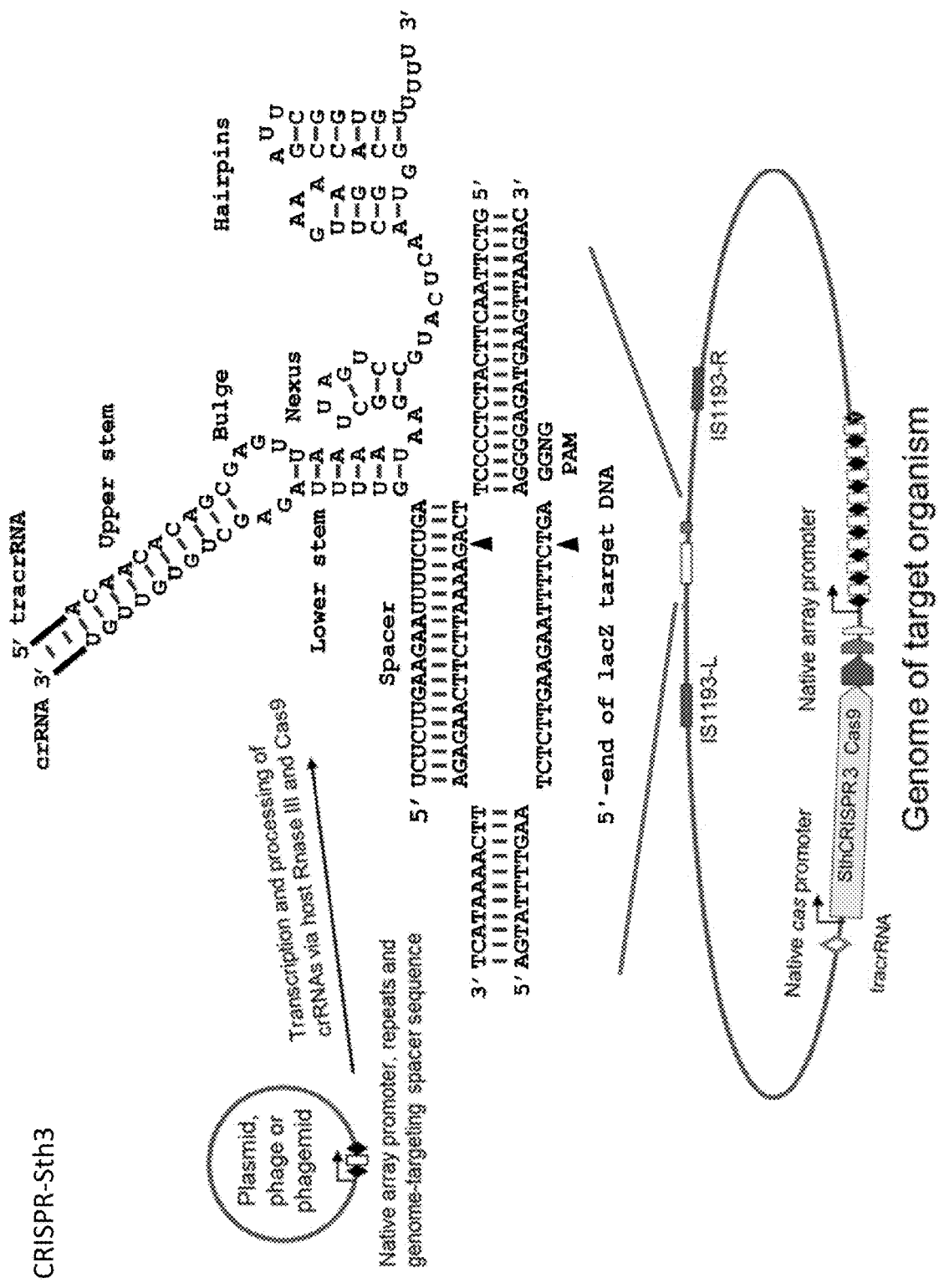

In Type II systems, Cas9 interrogates DNA and binds reversibly to PAM sequences with activation of Cas9 at the target occurring via formation of the tracrRNA::crRNA duplex (37), ultimately resulting in dsDNA cleavage (FIGS. 6A and 6B)(25). FIGS. 14A and 14B are schematics showing the general approach for co-opting endogenous CRISPR systems for targeted killing. In particular, these FIGS. 14A and 14B show the approach for co-opting endogenous type II systems in Streptococcus thermophilus for targeted killing. Thus, in *S. thermophilus*, programmed cell death was achieved using the CRISPR-Sth1 (A) or CRISPR-Sth3 (B) Type II system, by designing a genome targeting spacer sequence flanked by native repeats, whose expression was driven by a native or synthetic promoter. The transcribed repeat-spacer array is processed via host encoded RNAase III and Cas9 to yield mature crRNAs, which recruit Cas9 to the genome to elicit double-stranded DNA cleavage resulting in cell death.

Figure 6C:
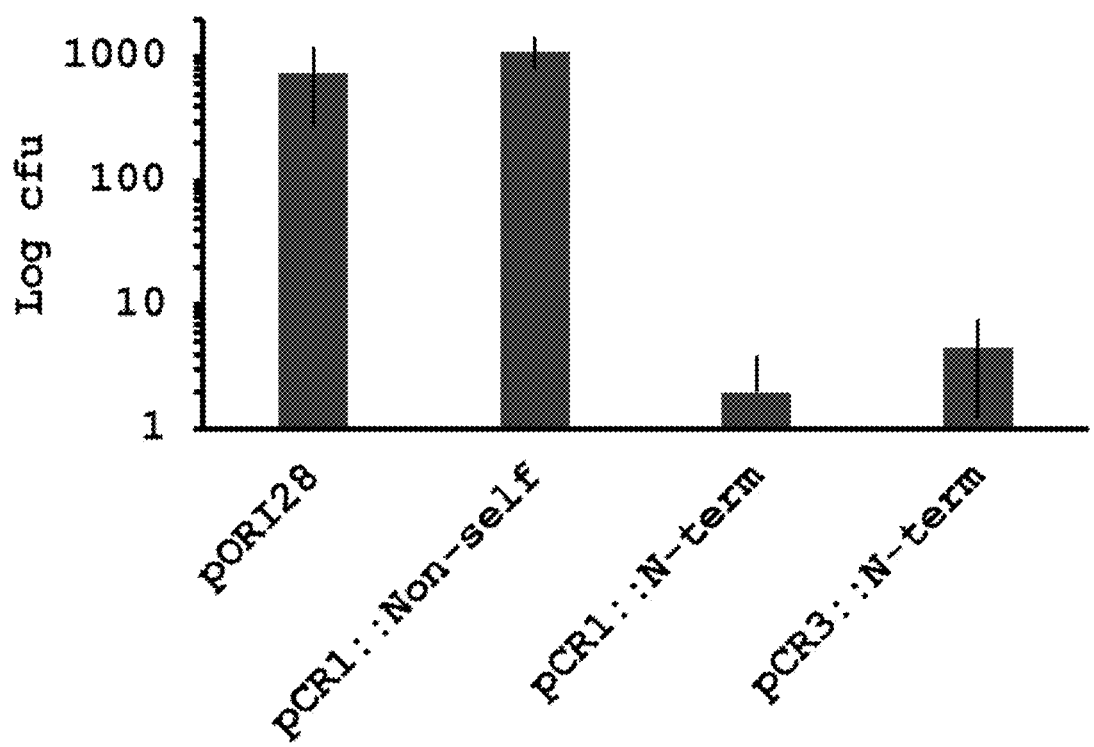

Transformation with plasmids eliciting chromosomal self-targeting by CRISPR-Cas systems appeared cytotoxic as measured by the relative reduction in surviving transformants compared to non-self-targeting plasmids (15, 29). Targeting the lacZ gene in *S. thermophilus* resulted in about a 2.5-log reduction in recovered transformants (FIG. 6C), approaching the limits of transformation efficiency. Double-stranded DNA breaks (DSBs) constitute a significant threat to the survival of organisms. The corresponding repair pathways often require end resection to repair blunt-ended DNA. Cas9-effected endonucleolysis further exacerbates the pressure for mutations caused by DSBs to occur, as restoration of the target locus to the wild-type does not circumvent subsequent CRISPR targeting. Identification of spacer origins within lactic acid bacteria revealed that 22% of spacers exhibit complementarity to self and that the corresponding genomic loci were altered, likely facilitating survival of naturally occurring self-targeting events (28).

Figure 7A:
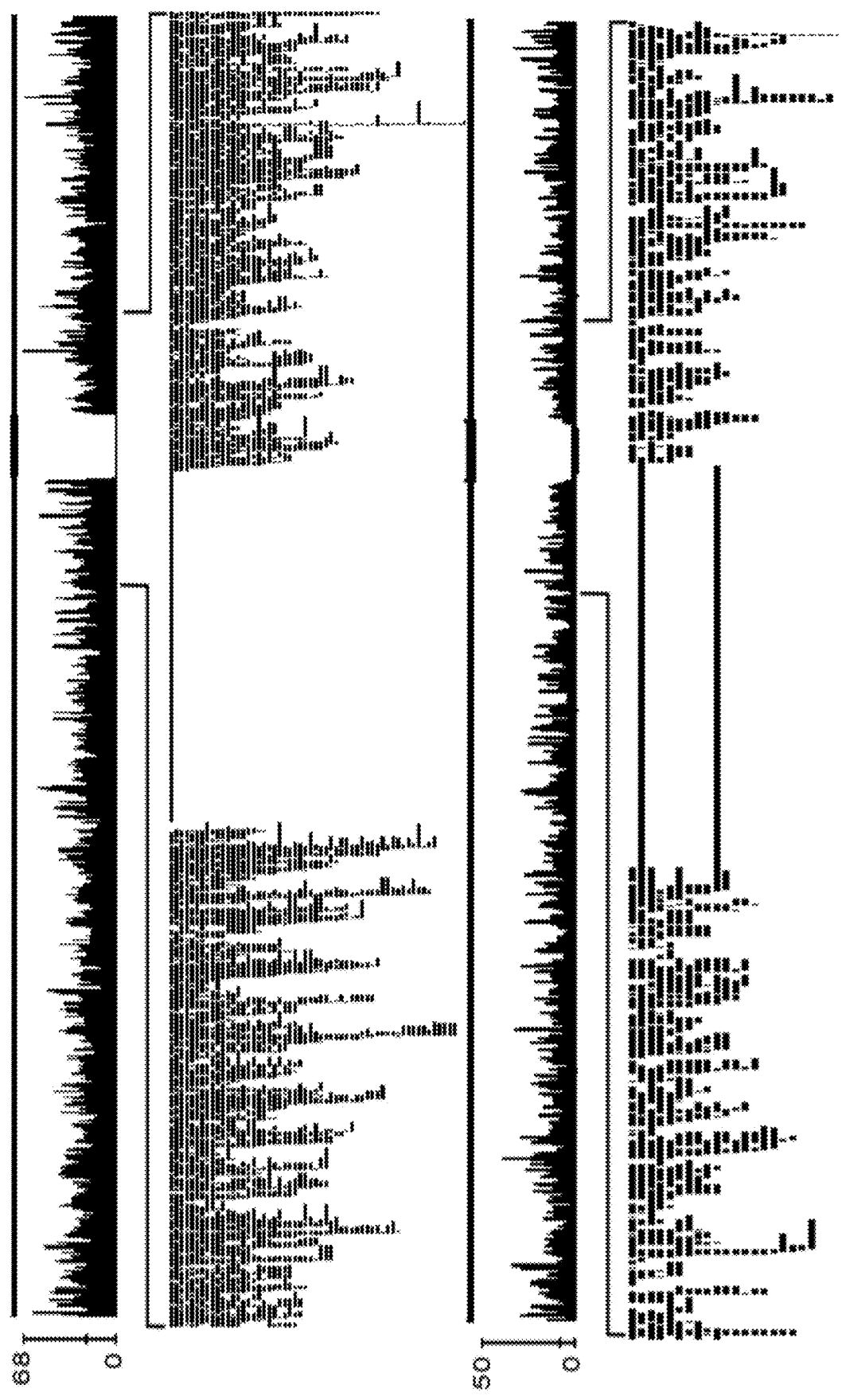

To determine if the target locus was mutated in response to Cas9-induced cleavage, transformants were first screened for loss of β-galactosidase activity. Clones deficient in activity were genotyped at the lacZ locus. No mutations due to classical or alternative end joining, nor any spontaneous single nucleotide polymorphisms were observed in any of the clones sequenced. The absence of single nucleotide polymorphisms may be attributed to a low transformation efficiency compounded by low incidence of point mutations, and the absence of Ku and LigaseIV homologs correlated with an absence of non-homologous end joining (38). PCR screening indicated that the wild-type lacZ was not present, but the PCR amplicons did not correspond to the native lacZ locus; rather, an IS element-flanked sequence at another genomic locus was amplified. To investigate the genotype responsible for the loss of β-galactosidase activity, Single Molecule Real Time sequencing was performed on two clones; one generated from CRISPR3 targeting the 5' end of lacZ, and one generated from CRISPR3 targeting the sequence encoding the ion-binding pocket necessary for β-galactosidase catalysis (FIG. 7A). This sequencing strategy was employed for its long read length to circumvent difficulty in reliably mapping reads to the proper locus, due to the high number of IS elements in the genome (35). Reads were mapped to the reference genome sequence using Geneious software, and revealed the absence of a large segment (about 102 kbp) encoding the lacZ open reading frame (FIG. 7A). Both sequenced strains confirmed the reproducibility of the large deletion boundaries, and showed that the deletion occurred independently of the lacZ spacer sequence or CRISPR-Cas system used for targeting. However, the sequencing data did not reliably display the precise junctions of the deletion.

The 102 kbp segments deleted constitute approximately 5.5% of the 1.86 Mbp genome of *S. thermophilus*. The region contained 102 putative ORFs (STER_1278-1379), encoding ABC transporters, two-component regulatory systems, bacteriocin synthesis genes, phage related proteins, lactose catabolism genes, and several cryptic genes with no annotated function (35). The effect of the deletion on growth phenotype was assessed in broth culture by measuring OD 600 nm over time (FIG. 7B). The deletion clones appeared to have a longer lag phase, lower final OD (p<0.01) and exhibited a significantly longer generation time during log phase with an average of 103 min, compared to 62 min for the wild-type (p<0.001). Although the deletion derivatives have 5.5% less of the genome to replicate per generation, and expend no resources in transcription or translation of the eliminated ORFs, no apparent increase in fitness was observed relative to the wild-type. β-galactosidase activity is a hallmark feature for industrial application of lactic acid bacteria and is essential for preservation of food systems through acidification. The capacity of lacZ deficient *S. thermophilus* strains to acidify milk was therefore assessed by monitoring pH (FIG. 7B). Predictably, the deletion strain failed to acidify milk over the course of the experiment, in sharp contrast to the rapid acidification phenotype observed in the wild-type.

Figure 8:
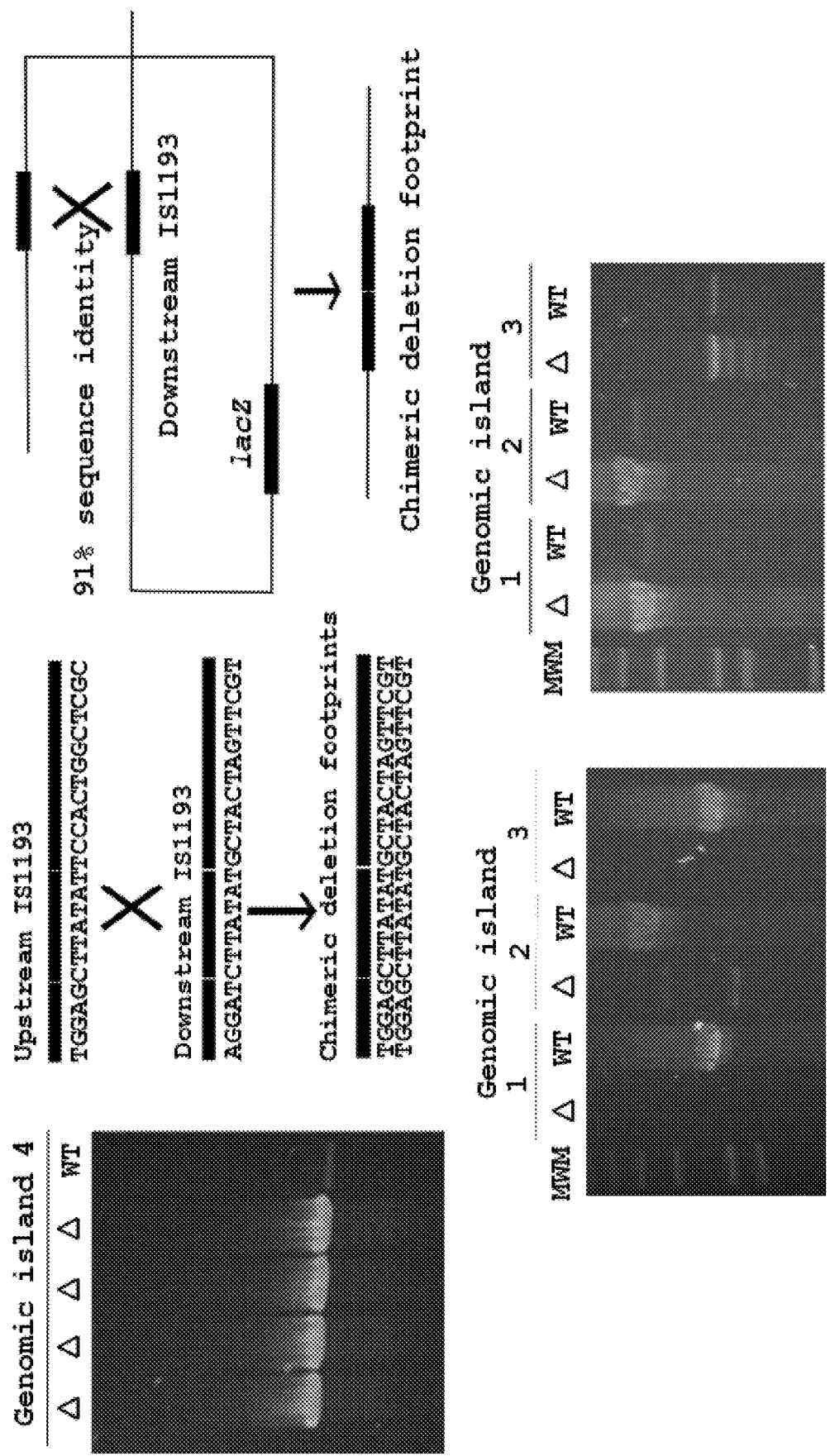
FIG. 8 provides a depiction of recombination events between insertion sequences (IS). In the top left panel, a gel electrophoresis image of large deletion amplicons yielded by PCR analysis of gDNA recovered from transformants Screening was performed using primers flanking the IS1193 elements upstream and downstream of the putative deletion site. Lanes denoted with Δ were amplified from gDNA of Lac⁻ clones recovered following CRISPR-Cas mediated targeting of lacZ, whereas WT is from wild-type. In the top middle panel, sequences of predicted recombination sites were determined by mapping single nucleotide polymorphisms corresponding to either upstream (SEQ ID NO:20) or downstream (SEQ ID NO:21) IS elements. The three sites are predicted based on sequences conserved in both IS elements. The sites depicted represent genotypes from independent clones and are representative of the Lac phenomenon observed at nine different recombination sites. Chimeric IS element footprints (SEQ ID NO:22) were similarly found in each genomic island locus at the deletion junction. The top right panel provides a schematic of IS's predicted to recombine during chromosomal deletion of the island encoding lacZ. The bottom left panel shows amplicons generated from primers flanking genomic islands 1, 2, and 3 to confirm deletions and the bottom right panel shows amplicons generated from internal primers to confirm the absence of wild-type sequences in each CRISPR-induced deletion culture. Lanes denoted with A were amplified from gDNA of clones recovered following CRISPR-Cas mediated targeting, and WT is wild-type.

Example 9. Genomic Deletions Occur Through Recombination Between Homologous IS Elements In order to investigate the mechanism of deletion, the nucleotide sequences flanking the segment were determined. The only homologous sequences observed at the junctions were two truncated IS1193 insertion sequences exhibiting 91% nucleotide sequence identity globally over 727 bp. Accordingly, a primer pair flanking the two IS elements was designed to amplify genomic DNA of surviving clones exhibiting the deletion. Each of the deletion strains exhibited a strong band of the predicted size (about 1.2 kb), and confirmed the large genomic deletion event (FIG. 8, top left panel). Interestingly, a faint amplicon corresponding to the chromosomal deletion was observed in the wild-type, indicating that this region may naturally excise from the genome at a low rate within wild-type populations. Sequencing of the junction amplicon was performed for 20 clones generated by chromosomal self-targeting by CRISPR3. Genotyping of the locus revealed the presence of one chimeric IS element in each clone and, furthermore, revealed the transition from the upstream element to the downstream sequence within the chimera for each clone (FIG. 8, top middle panel). The size of deletions observed ranged from 101,865-102,146 bp. The exact locus of transition was variable, but non-random within the clones, implying the potential bias of the deletion mechanism. *S. thermophilus* harbors typical recombination machinery encoded as RecA (STER_0077), AddAB homologs functioning as dual ATP-dependent DNA exonucleases (STER_1681 and STER_1682), and a helicase (STER_1742) of the RecD family. The high nucleotide identity between the flanking IS elements and the capacity for *S. thermophilus* to carry out site-specific recombination (4) confirms the potential for RecA-mediated recombination to mediate excision of the genomic segment (FIG. 8, top right panel).

Next, CRISPR-Cas targeting was evaluated for the ability to facilitate isolation of deletions for each locus with the same genetic architecture. For this purpose, three CRISPR3 repeat-spacer arrays, one targeting the oligonucleotide transporter in the first locus, prtS from the second locus, and the ATPase copper efflux gene from the third locus were generated and cloned into pORI28 (FIG. 5). In order to screen for deletions, primers flanking the IS elements at each locus were designed to amplify each deletion junction (FIG. 8, bottom left panel). The absence of wild-type loci was also confirmed in each case by designing internal primers for each genomic island (FIG. 8, bottom right panel) Following transformations with the targeting plasmids, deletions at each locus were isolated and the absence of wild-type confirmed. Sequencing of the deletion junction amplicons confirmed that a single chimeric IS element footprint remained, indicating a common mechanism for deletion at each locus. Interestingly, primers flanking the IS elements also amplified from wild-type gDNA, further suggesting that population heterogeneity naturally occurred at each locus was due to spontaneous genomic deletions. These results imply that sequence-specific Cas9 cleavage selects for the variants lacking protospacer and PAM combinations necessary for targeting. Thus, spontaneous genomic deletions can be isolated using CRISPR-Cas targeting as a strong selection for microbial variants that have already lost those genomic islands.

Example 10. Population Screening

In this study, native Type IIA systems harbored in *S. thermophilus* were repurposed for defining spontaneous deletions of large genomic islands. By independently targeting four islands in *S. thermophilus*, stable mutants collectively lacking a total of 7% of the genome were generated. Characterization of the deletion junctions suggested that an IS-dependent recombination mechanism contributes to population heterogeneity and revealed deletion events ranging from 8 to 102 kbp. Precise mapping of the chimeric IS elements indicated that natural recombination events are likely responsible for the large chromosomal deletions in *S. thermophilus* and could potentially be exploited for targeted genome editing.

Our results demonstrate that wild-type clones were removed from the population while mutants without CRISPR-Cas targeted features survived. Thus, adaptive islands were identified and validated, showing that precise targeting by an endogenous Cas9 can be exploited for isolating large deletion variants in mixed populations.

Genome evolution of bacteria occurs through horizontal gene transfer, intrinsic mutation, and genome restructuring. Genome sequencing and comparative analysis of *S. thermophilus* strains has revealed significant genome decay, but also indicates that adaptation to nutrient-rich food environments occurred through niche-specific gene acquisition (18; 35). The presence of MGEs including integrative and conjugative elements, prophages, and IS elements in *S. thermophilus* genomes is indicative of rapid evolution to a dairy environment (38-39). Mobile genetic features facilitate gene acquisition and conversely, inactivation or loss of non-essential sequences. Consequently, MGEs confer genomic plasticity as a means of increasing fitness or changing ecological lifestyles. Our results strongly indicate that CRISPR-Cas targeting of these elements may influence chromosomal rearrangements and homeostasis. This is in contrast to experiments targeting essential features, which resulted in selection of variants with inactivated CRISPR-Cas machinery (Jiang 2013). Mutation of essential ORFs is not a viable avenue for circumvention of CRISPR-Cas targeting, and thus only those clones with inactivated CRISPR-Cas systems remain. By design, targeting genetic elements predicted to be hypervariable and expendable demonstrated that variants with altered loci were viable, maintaining active CRISPR-Cas systems during self-targeting events.

Despite the near ubiquitous distribution of IS elements in bacterial genomes they remain an enigmatic genetic entity, largely due to their diversity and plasticity in function (34). Our results suggest it is possible to predict recombination between related IS elements by analyzing their location, orientation, and sequence conservation (FIG. 4 and FIGS. 5A-5D). CRISPR-Cas targeting can then be employed to empirically validate population heterogeneity at each predicted locus, and simultaneously increase the recovery of low incidence mutants. The high prevalence of MGEs in lactic acid bacteria, and especially *S. thermophilus*, is in accordance with their role in speciation of these hyper-adapted bacteria through genome evolution (39-40). Moreover, recovery of genomic deletion mutants using CRISPR-Cas targeting could facilitate phenotypic characterization of genes with unknown function. Mutants exhibiting the deletion of the 102 kb island encoding the lac operon had significantly increased generation times relative to the wild-type and achieved a lower final OD. With 102 predicted ORFs therein, it is likely that additional phenotypes are affected and many of the genes do not have annotated functions. Considering the industrial relevance of niche-specific genes such as prtS, this method allows for direct assessment of how island-encoded genes contribute to adaption to grow in milk. Moreover, it is in the natural genomic and ecological context of these horizontally acquired traits, since they were likely acquired as discrete islands. These results establish new avenues for the application of self-targeting CRISPR-Cas9 systems in bacteria for investigation of transposition, DNA repair mechanisms, and genome plasticity.

CRISPR-Cas systems generally limit genetic diversity through interference with genetic elements, but acquired MGEs can also provide adaptive advantages to host bacteria. Thus, the benefit of maintaining genomically integrated MGEs despite CRISPR-Cas targeting is an important driver of genome homeostasis. Collectively, our results establish that in silico prediction of GEIs can be coupled with CRISPR-Cas targeting to isolate clones exhibiting large genomic deletions. Chimeric insertion sequence footprints at each deletion junction indicated a common mechanism of deletion for all four islands. The high prevalence of self-targeting spacers exhibiting identity to genomic loci, combined with experimental demonstrations of genomic alterations, suggest that CRISPR-Cas self-targeting may contribute significantly to genome evolution of bacteria (28;30). Collectively, studies on CRISPR-Cas induced large deletions substantiate this approach as a rapid and effective means to assess the essentiality and functionality of gene clusters devoid of annotation, and define minimal bacterial genomes based on chromosomal deletions occurring through transposable elements.

Figure 9:
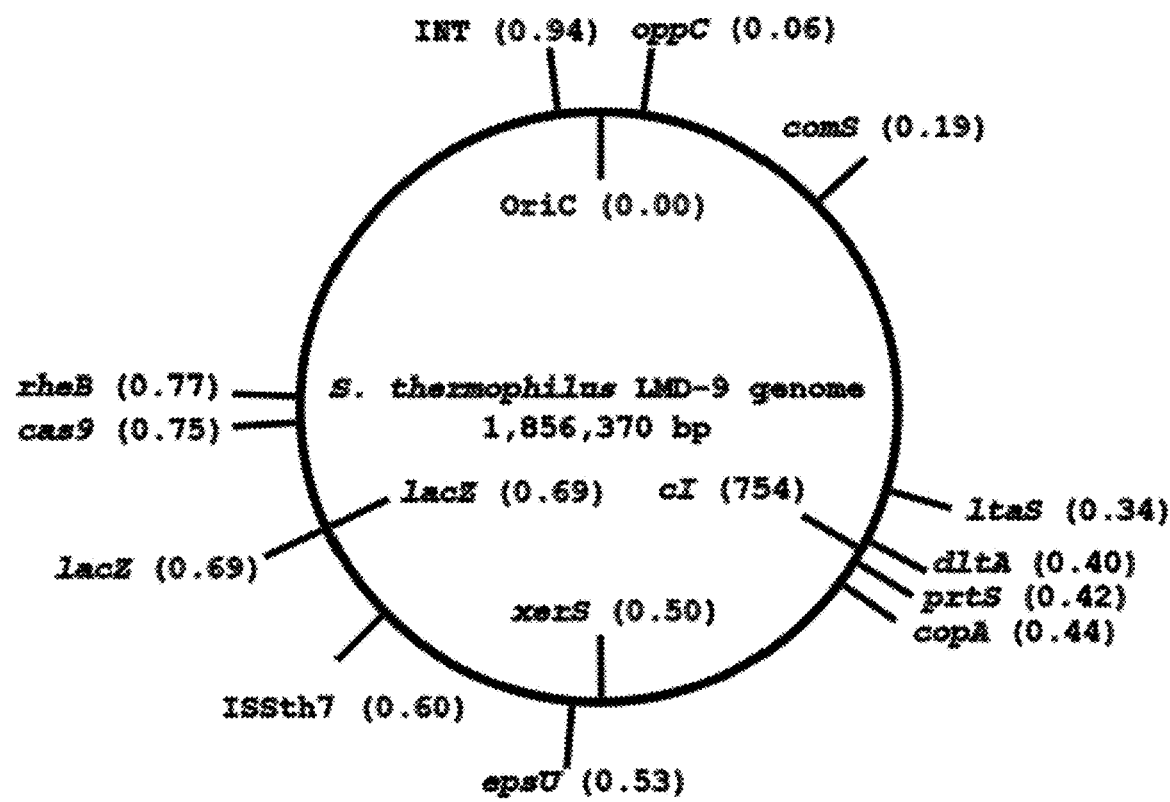
FIG. 9 provides targets of lethality and shows use of defined genetic loci for assessing type II CRISPR-Cas system-based lethality via targeting the genome of *Streptococcus thermophilus* LMD-9. Both orthogonal type II systems (CRISPR1 and CRISPR3) were tested. Specific genetic features were selected to test (i) intergenic regions (INT), (ii) mobile genetic elements (ISSth7, oppC-GEI1, prtS-GEI2, copA-GEI3, cI, lacZ-GEI4, epsU), (iii) essential genes (dltA, ltaS), (iv) poles of the replichore (OriC, xerS), and forward vs. reverse strands of DNA (outer targets vs. inner targets).

FIG. 9 shows defined genetic loci for assessing type II CRISPR-Cas system-based lethality via targeting the genome of *Streptococcus thermophilus* LMD-9. The methods to carry out this analysis are known in the art. See, Selle and Barrangou *PNAS*. 112(26):8076-8081 (2015).

Both orthogonal type II systems (CRISPR1 and CRISPR3) were tested; CRISPR1 targets in dark grey, CRISPR3 targets in light grey. Specific genetic features were selected to test (i) intergenic regions (INT), (ii) mobile genetic elements (IS, GEI1-GEI3, PRO, lacZ, EPS), (iii) essential genes (dltA, LTA), (iv) poles of the replichore (ORI, TER), and forward versus reverse strands of DNA (outer targets versus inner targets).

Figure 10:
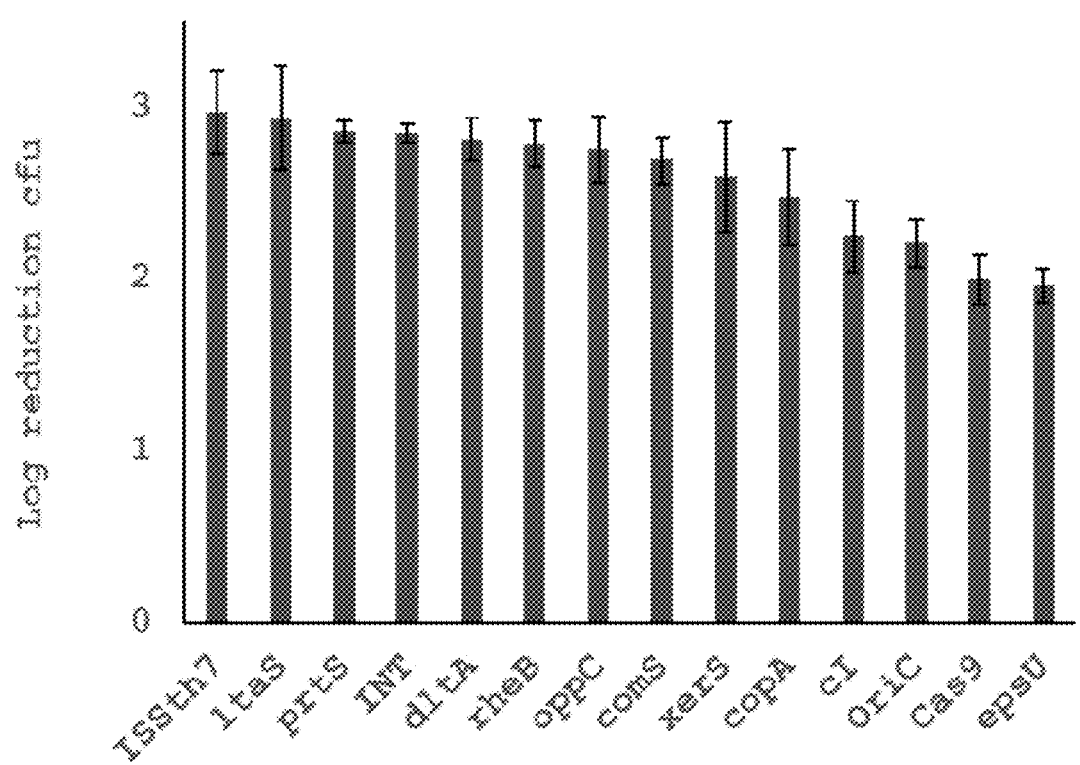
FIG. 10 shows CRISPR-based lethality achieved by targeting the regions defined in FIG. 9. Log reduction in CFU (cell forming units) was calculated with regard to transformation of a non-targeting plasmid control; pORI28. Lethality ranged from 2-3 log reduction for all targets tested, regardless of chromosomal location, coding sequence, or essentiality. ISSth7-insertion sequence element, ltaS-lipoteichoic acid synthase; prtS-genomic island 2; INT-intergenic region; dltA-D-alanine ligase; rheB-chi site deficient locus; oppC-genomic island 1; comS-chi site dense locus; xerS-terminus of replication; copA-genomic island 3; cI-prophage remnant; OriC-origin of replication; Cas9-CRISPR3 Cas9 coding sequence; epsU-exopolysaccharide cassette.

FIG. 10 shows CRISPR-based lethality achieved by targeting the regions defined in FIG. 9. Log reduction in CFU was calculated with regard to transformation of a non-targeting plasmid control; pORI28. Lethality ranged from 2-3 log reduction for all targets tested, regardless of chromosomal location, coding sequence, or essentiality.

Figure 11:
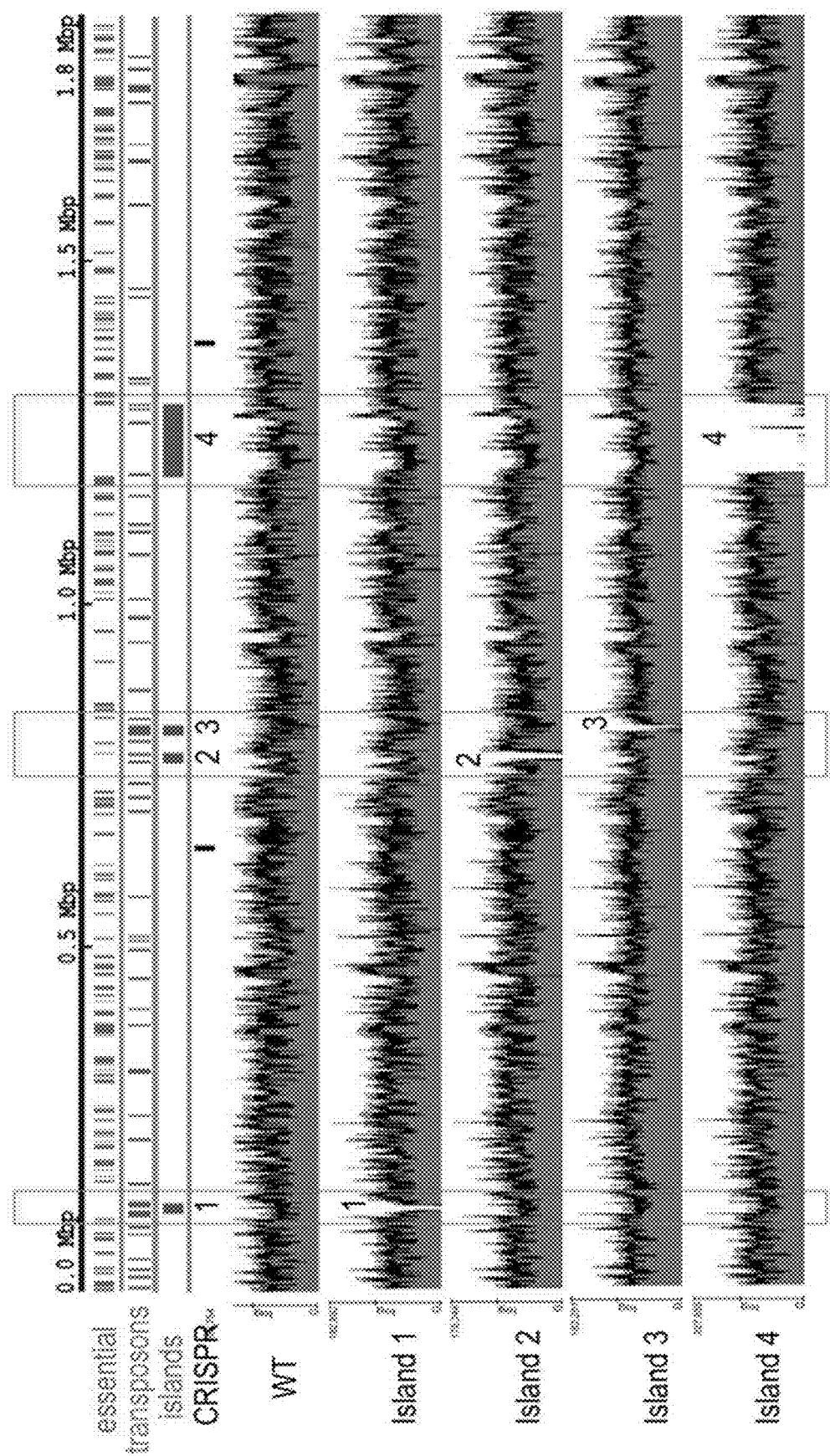
FIG. 11 shows transcriptional profiles of CRISPR-mediated genomic island deletion strains.

FIG. 11 shows transcriptional profiles of CRISPR-mediated genomic island deletion strains. Recovery and genotyping of cells surviving CRISPR targeting of the genomic islands 1-4 resulted in identification of stable independent mutants lacking the genomic island targeted in each experiment. Subsequently, the cells were propagated and their total RNA was isolated and sequenced. Using this approach, transcriptional profiles were generated by mapping sequencing reads to the reference genome. In each case, the absence of sequencing reads to the predicted genomic island loci further suggested the loss of the target genetic entity, while having minimal impact on the expression of core genes throughout the rest of the genome.

Figure 12:
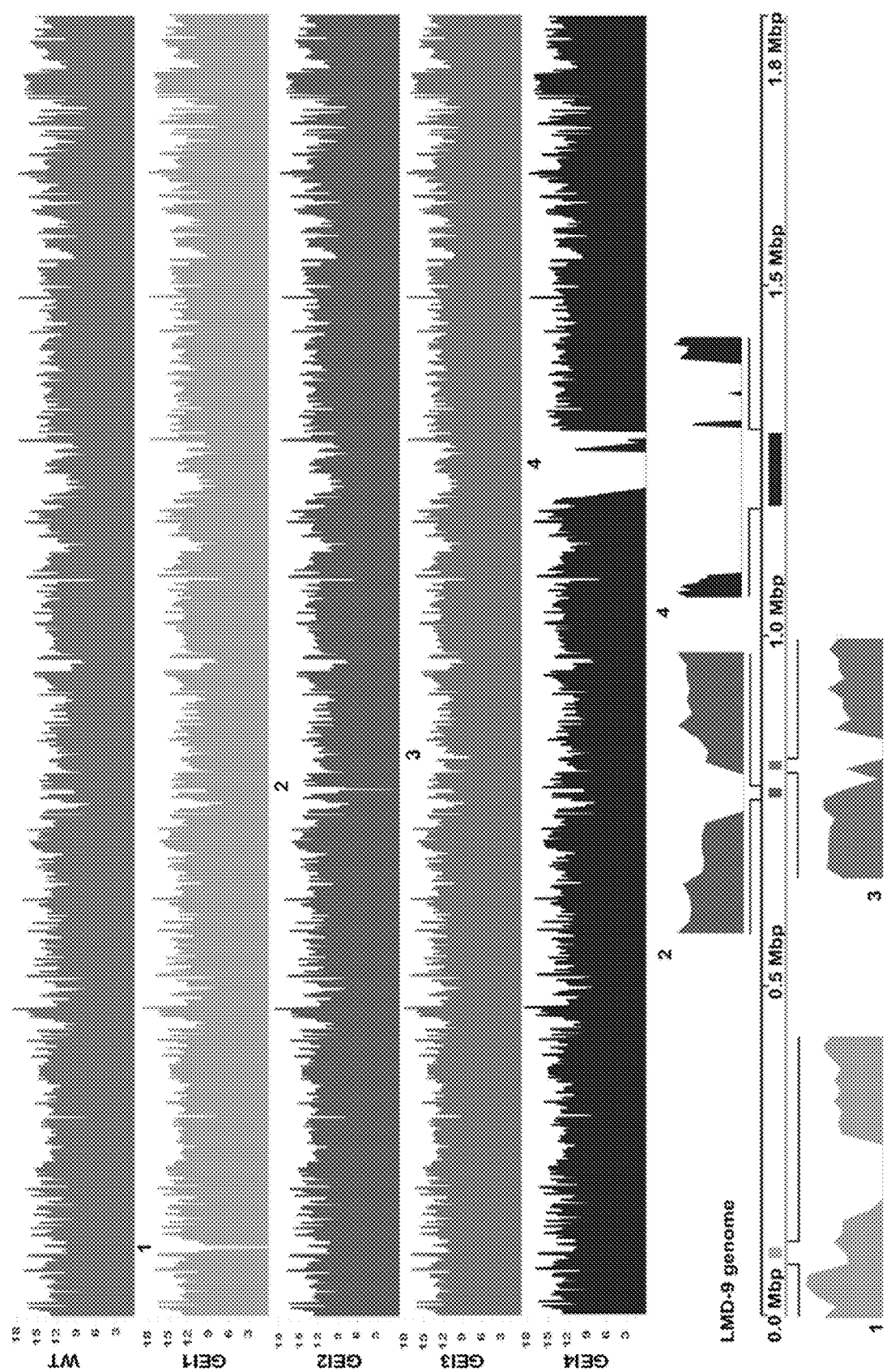
FIG. 12 shows $\log_e$ transformed RNA-sequencing read coverage of genomic island deletion strains, GEI1, GEI2, GEI3, and GEI4.

Furthermore, RNA sequencing data supports the boundaries of the deletions by using read coverage mapping and transcriptional value comparisons and additionally supports the discernment of phenotype using comparative transcriptomics generated using the same data set. Specifically, the lack of transcriptional activity present at the expected deletion regions using high-throughput RNA-sequencing is confirmed as shown in FIG. 12. FIG. 12 shows $\log_2$ transformed RNA-sequencing read coverage of genomic island deletion strains and for each genomic island strain (GEI1-GEI4), the absence of sequencing reads to the predicted genomic island loci further suggested the loss of the target genetic entity, while having minimal impact on the expression of core genes throughout the rest of the genome.

FIG. 13 further confirms lack of transcriptional activity for the deleted genes. For each of the genomic island deletion strains (GEI1-GEI4), the expression of genes encoded on each of the target islands (black) was minimal. Genes encoded in GEI1 are shown in the upper left panel, genes encoded in GEI2 are shown in the upper right panel, genes encoded in GEI3 are shown in the lower left panel, and genes encoded in GEI4 are shown in the lower right panel. In general, genomic island deletions 1 and 2 had minimal impact on the transcription of other genes (gray), whereas genomic island 3 and 4 appeared to affect the transcription of other genes not encoded on the islands.

In addition, RNA-sequencing data was used to compare the transcriptional levels of genes not encoded on the deleted island (GEI4), i.e., other genes still present in the chromosome, and identifying phenotypes associated with genomic deletions. Genes that are differentially transcribed in the deletion strain suggest that cellular processes were impacted by the genes that were lost or that there is compensation for the loss of the activity of these genes. Thus, inferences can be made about the pathways to which these genes or genomic regions are relevant. Table 5 provides a list of differentially expressed genes identified in deletion strain GEI4. Many of the genes observed to be differentially expressed relate to the biosynthetic capacity of Streptococcus thermophilus, including aromatic amino acid and purine biosynthesis.

Figure 15:
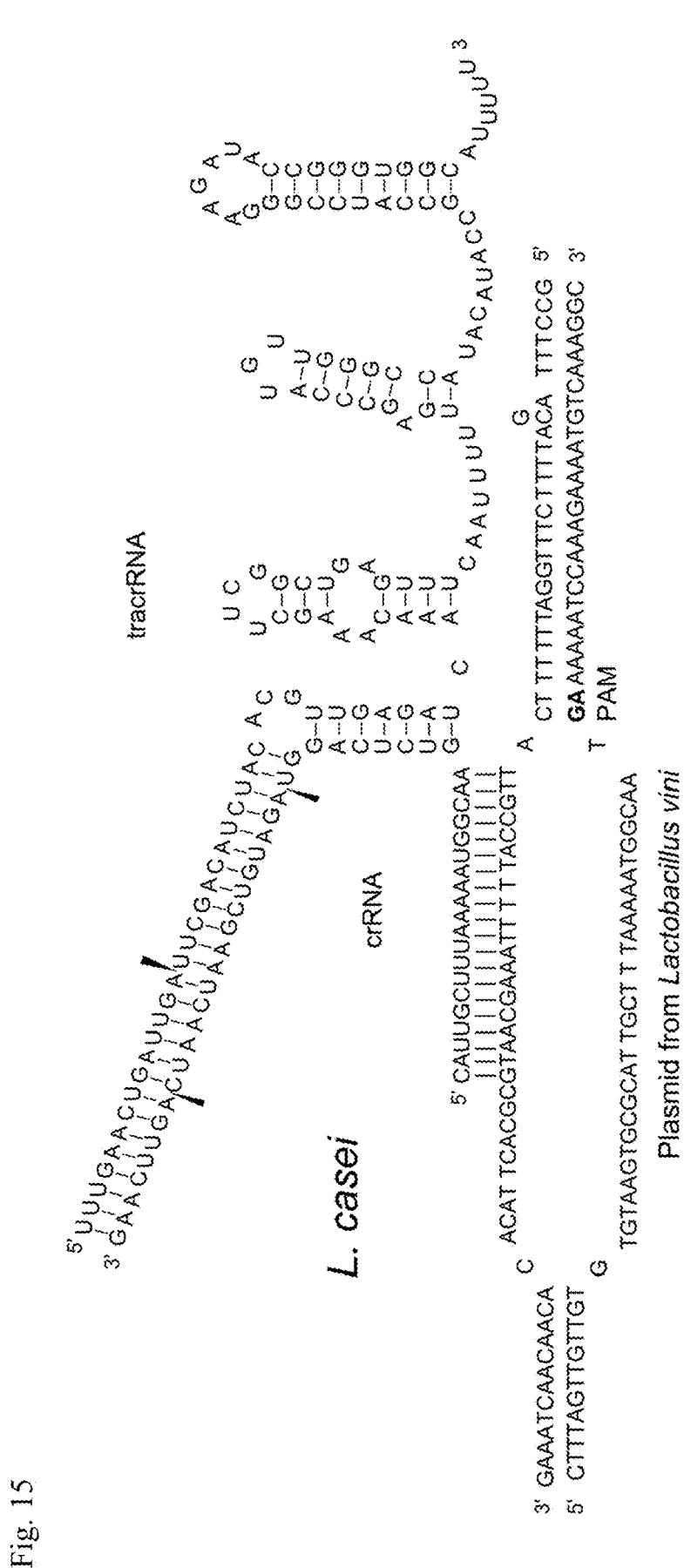
FIG. 15. The Type II guides of *Lactobacillus casei*. The first structure is the predicted guide (crRNA:SEQ ID NO:23; tracrRNA:SEQ ID NO:24; plasmid from *L. vini*, upper strand: SEQ ID NO:26; lower strand: SEQ ID NO:25). The second figure is the correct dual guide crRNA (SEQ ID NO:23):tracrRNA (SEQ ID NO:24) as confirmed by RNA Sequencing (plasmid from *L. vini*, upper strand: SEQ ID NO:26; lower strand: SEQ ID NO:25). The third figure is an example of a predicted artificial single guide (SEQ ID NO:28; plasmid from *L. vini*, upper strand: SEQ ID NO:26; lower strand: SEQ ID NO:25).

Example 11. Targeted Killing of *Lactobacillus casei* Using a Type II CRISPR-Cas System Exemplary CRISPR-Cas Type II guides of *L. Casei* are provided in FIG. 15. The first structure provides a predicted guide, while the second structure shows an exemplary dual guide structure and the third structure shows an exemplary single guide structure.

Figure 16:
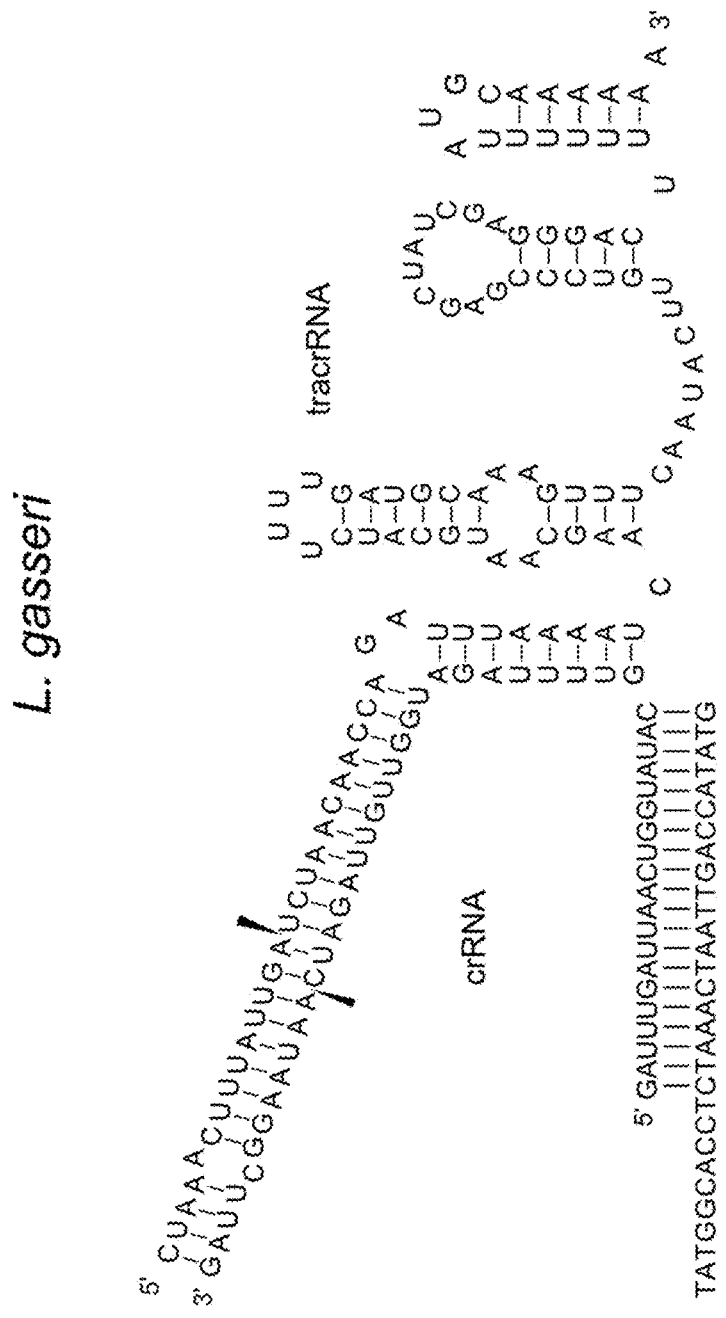
FIG. 16 provides exemplary Type II guides of *Lactobacillus gasseri*. The first structure is the predicted guide (crRNA:SEQ ID NO:29; tracrRNA:SEQ ID NO:30; protospacer: SEQ ID NO:31). The second figure is the correct dual guide crRNA (SEQ ID NO:29):tracrRNA (SEQ ID NO:32) as confirmed by RNA Sequencing. The third figure is an example of a predicted artificial single guide (SEQ ID NO:35; target DNA, upper strand: SEQ ID NO:37; lower strand: SEQ ID NO:36).

Example 12. Targeted Killing of *Lactobacillus gasseri* Using a Type II CRISPR-Cas System Exemplary Type II guides for targeted killing of *L. gasseri* are provided in FIG. 16. The first structure provides the predicted guide, while the second structure provides the correct dual guide crRNA:tracrRNA (confirmed by RNA sequencing) and the third structure provides an exemplary predicted single guide.

Figure 19:
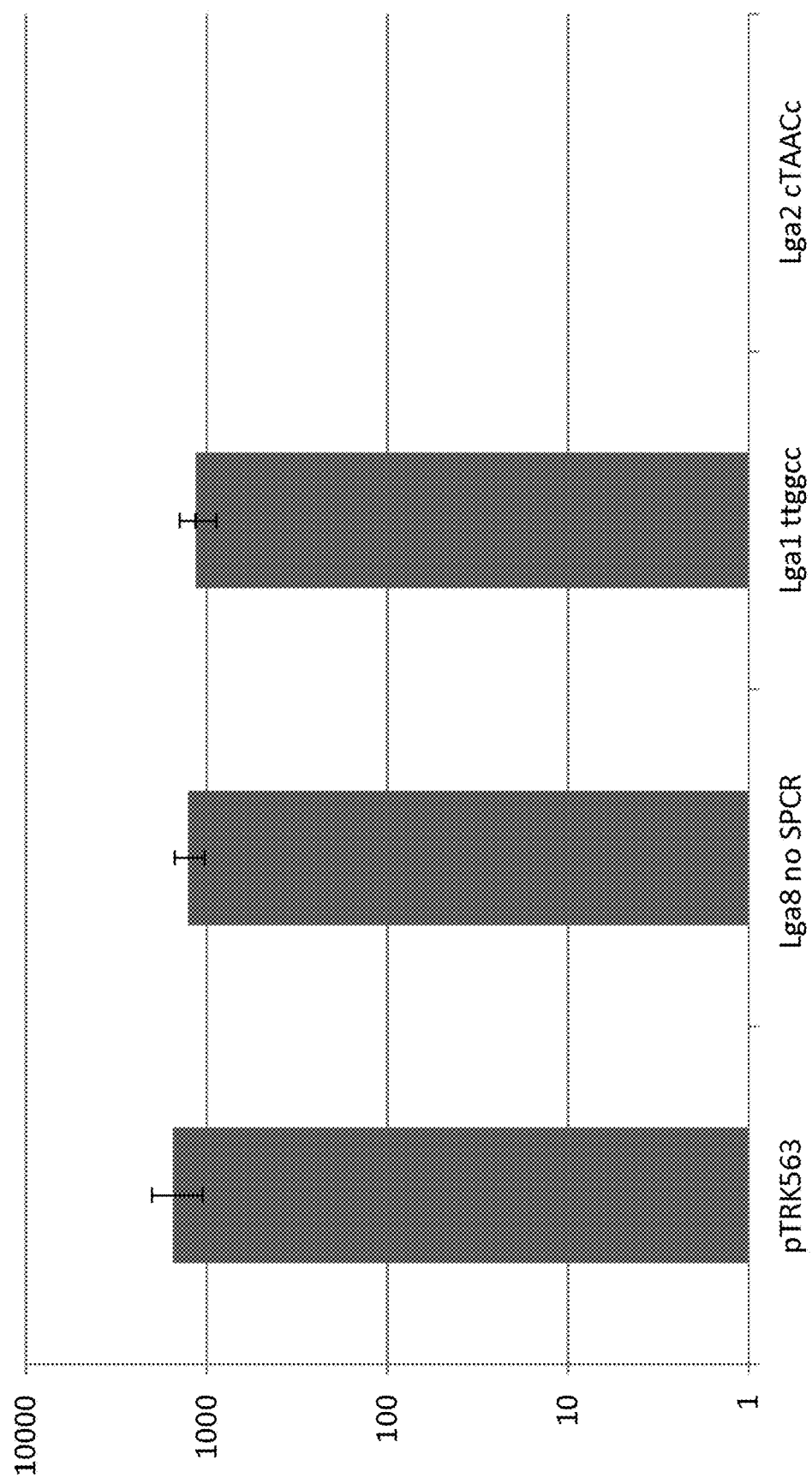
FIG. 19 shows the results of transformation of plasmids containing a protospacer that matches the most highly transcribe crRNA in the native *L. gasseri* Type II CRISP SR array. From left to right, four different plasmids were transformed into *L gasseri*: an empty pTRK563 vector, a construct with the correct protospacer but an incorrect PAM, the correct PAM but a protospacer that is not in the array, and the correct protospacer with the PAM that demonstrated the most interference targeting and cell death. The reported values represent the mean±SEM of three independent replicates.

Plasmids were transformed into *L. gasseri* each carrying different constructs as follows: an empty pTRK563 vector, a construct with the correct protospacer but an incorrect PAM, the correct PAM but a protospacer that is not in the array, and the correct protospacer with the PAM. The results are shown in FIG. 19. The plasmid having the correct protospacer and correct PAM showed significantly more interference targeting and cell death.

Figure 17:
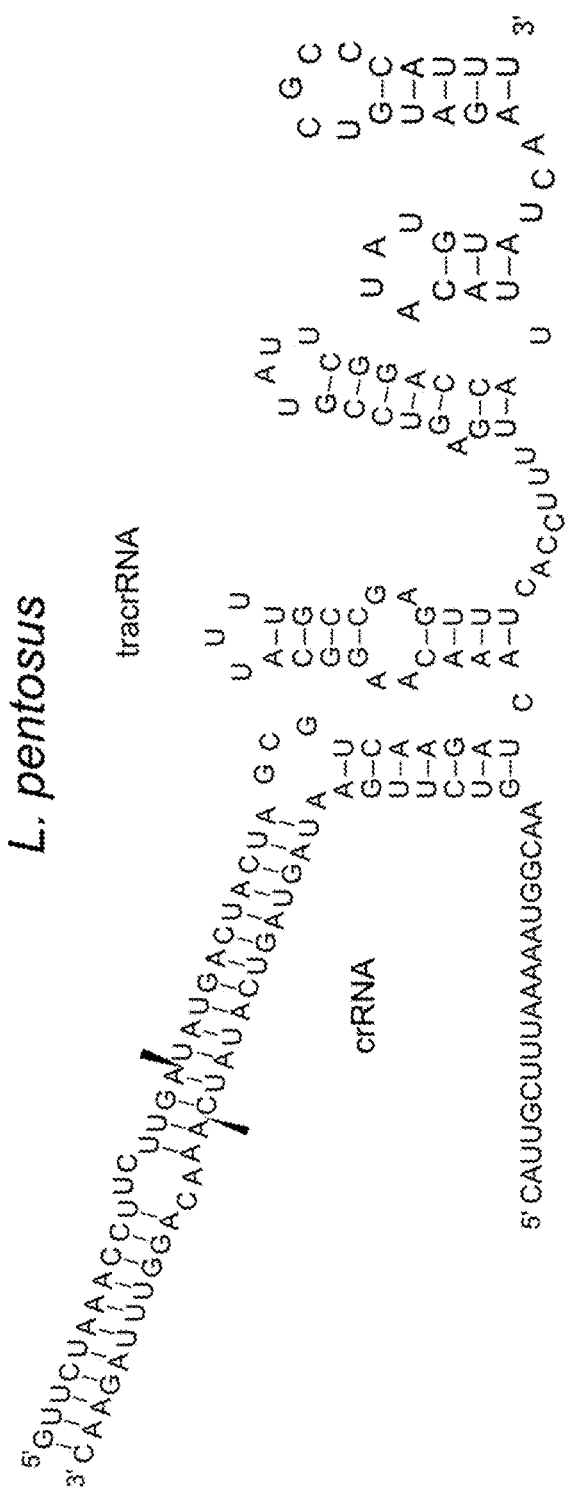
FIG. 17 provides exemplary Type II guides of *Lactobacillus pentosus*. The first structure is the predicted guide (crRNA:SEQ ID NO:38; tracrRNA:SEQ ID NO:39. The second figure is the correct dual guide crRNA (SEQ ID NO:38):tracrRNA (SEQ ID NO:40) as confirmed by RNA Sequencing. The third figure is an example of a predicted artificial single guide (SEQ ID NO:43; target DNA, upper strand: SEQ ID NO:42; lower strand: SEQ ID NO:41).

Example 13. Targeted Killing of *Lactobacillus pentosus* Using a Type II CRISPR-Cas System Exemplary Type II guides for targeted killing of *L. pentosus* are provided in FIG. 17. The first structure shows the predicted guide. The second structure is the correct dual guide crRNA:tracrRNA (confirmed by RNA Sequencing) and the third structure is an exemplary predicted artificial single guide.

Figure 20:
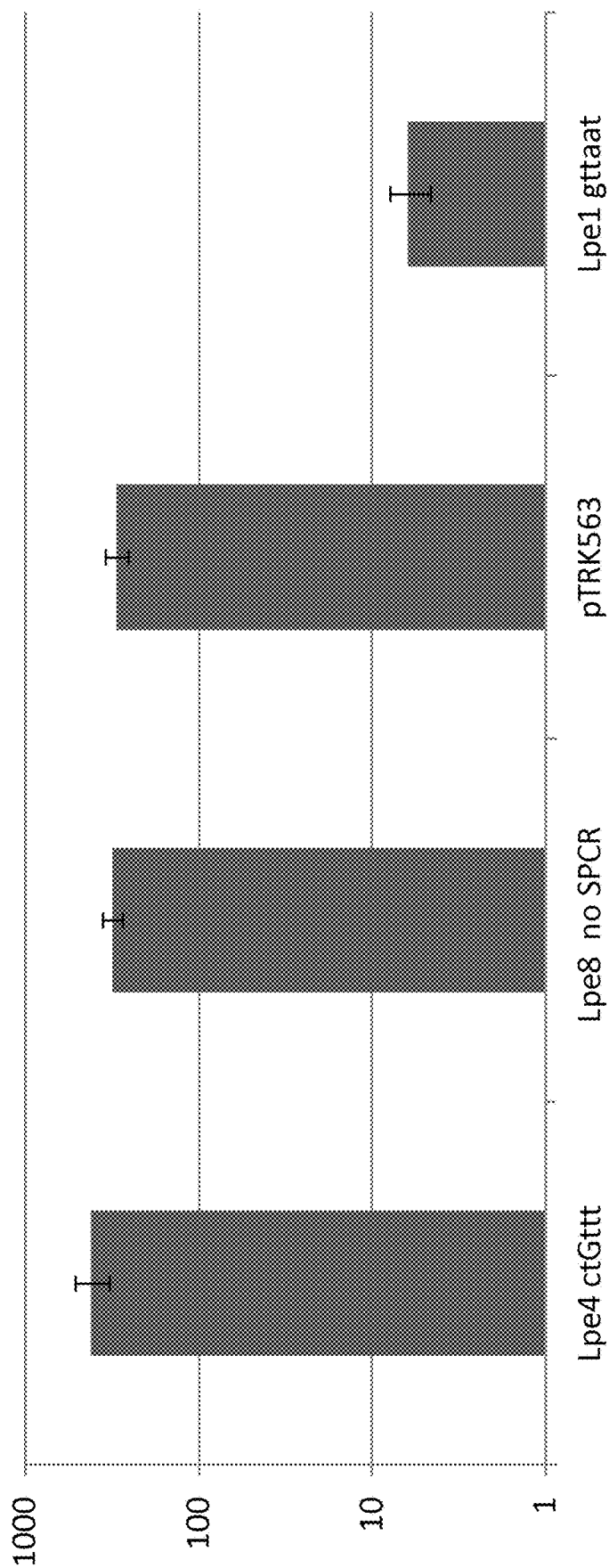
FIG. 20 shows transformation of plasmids containing a protospacer that matches the most highly transcribe crRNA in the native *L. pentosus* Type II CRISPSR array. From left to right, four different plasmids were transformed into *L. pentosus*: a construct with the correct protospacer but an incorrect PAM (Lpe4 ctGttt), the correct PAM but a protospacer that is not in the array (Lpe8 noSPCR), an empty pTRK563 vector (pTRK563), and a plasmid with the correct protospacer and correct PAM (Lpe1 gttaat). The reported values represent the mean±SEM of three independent replicates.

Plasmids were transformed into *L. pentosus*, each plasmid carrying different constructs as follows: a construct with the correct protospacer but an incorrect PAM, a construct with a correct PAM but a protospacer that is not in the array, an empty pTRK563 vector, and a correct protospacer with a correct PAM. The results are shown in FIG. 20. The plasmid having a correct protospacer and correct PAM (Lpe1 gttaat) showed significantly more interference targeting and cell death.

Figure 18:
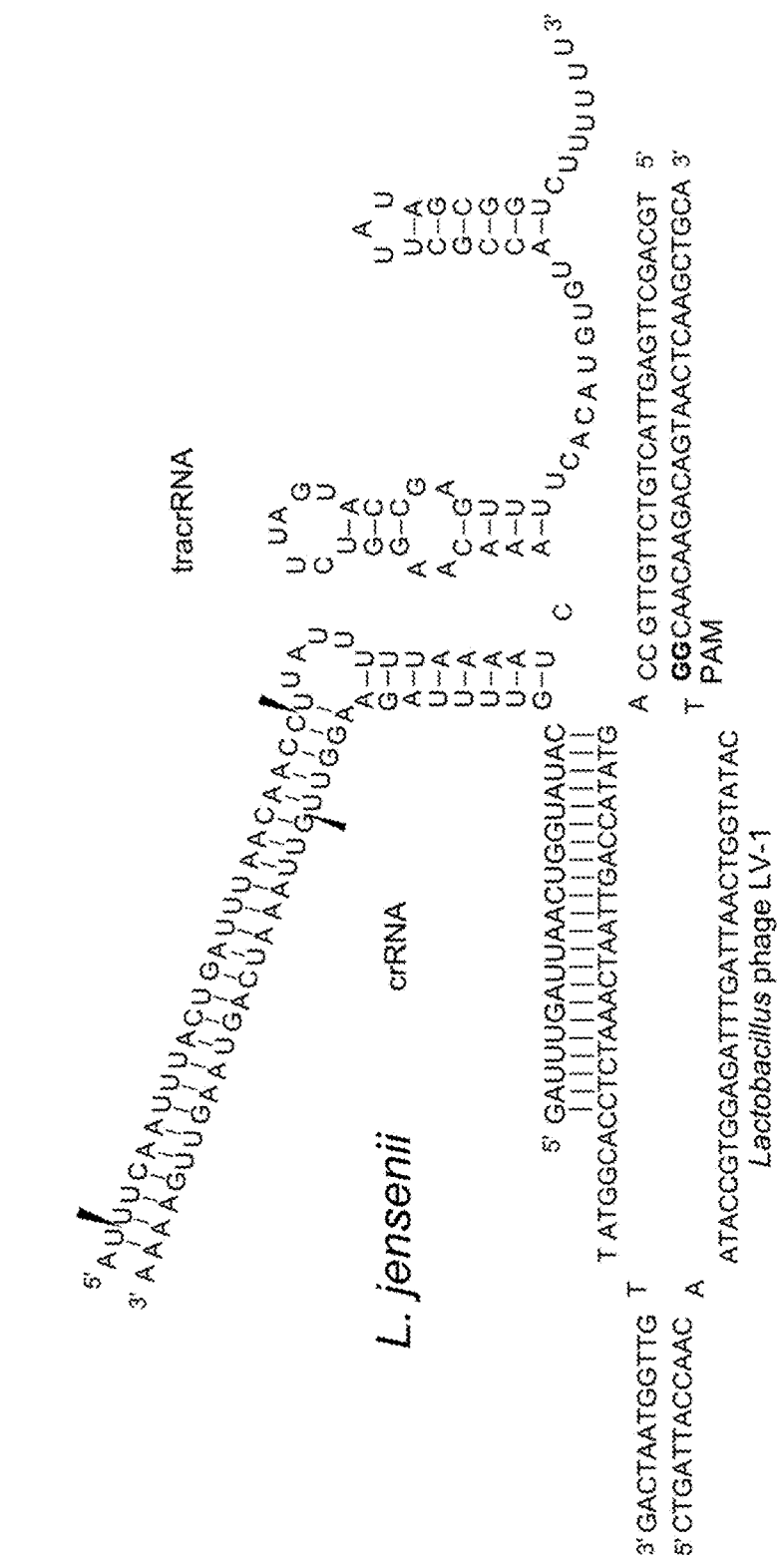
FIG. 18 provides exemplary Type II guides of *Lactobacillus jensenii*. The first figure is the correct dual guide crRNA (SEQ ID NO:44):tracrRNA (SEQ ID NO:45) as confirmed by RNA Sequencing (*Lactobacillus* phage LV-1, upper strand: SEQ ID NO:47, lower strand: SEQ ID NO:46). The bottom figure provides an example of a predicted artificial single guide (SEQ ID NO:48; *Lactobacillus* phage LV-1, upper strand: SEQ ID NO:47, lower strand: SEQ ID NO:46).

Example 14. Targeted Killing of *Lactobacillus jensenii* Using a Type II CRISPR-Cas system FIG. 18 provides exemplary CRISPR-Cas Type II guides. The first structure is the correct dual guide crRNA:tracrRNA as confirmed by RNA sequencing and the second structure is an exemplary predicted artificial single guide.

Figure 22:
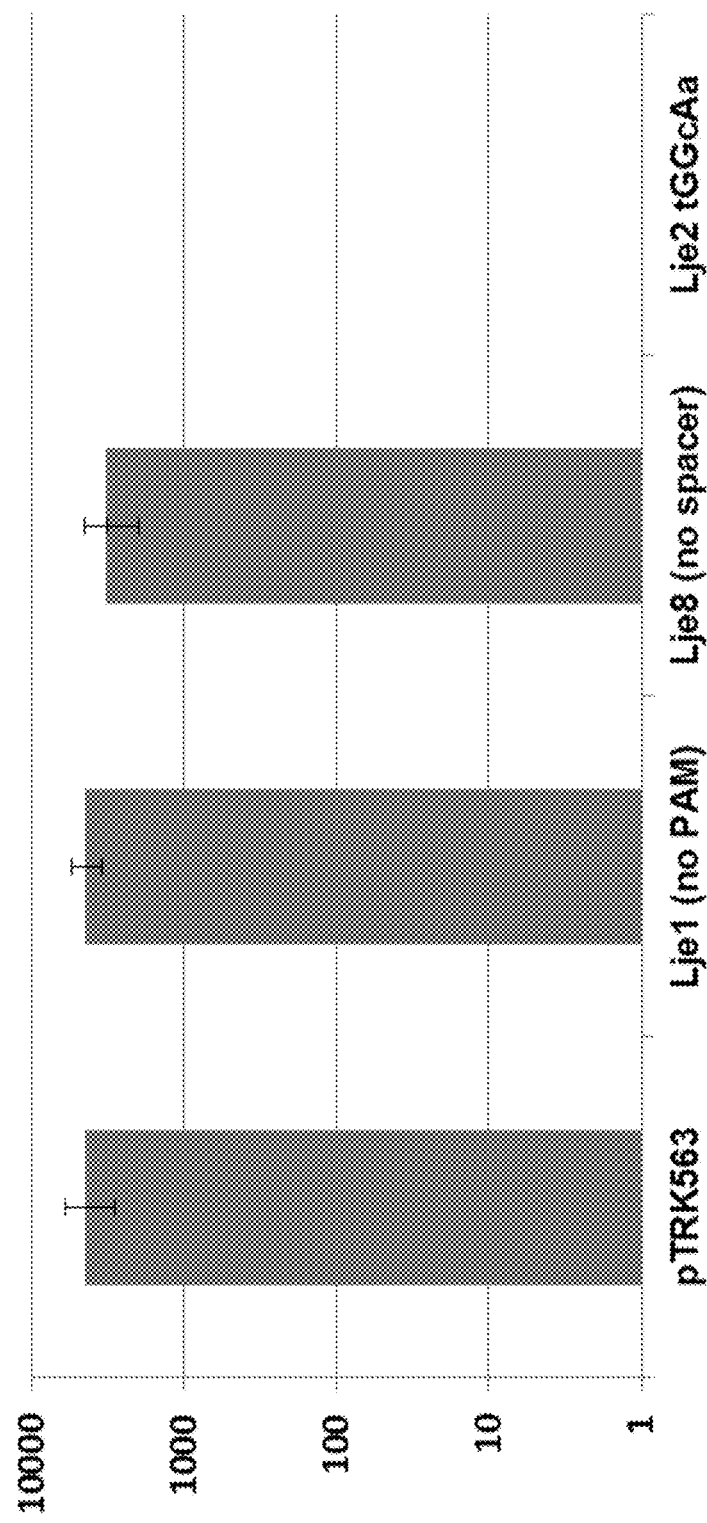
FIG. 22 shows transformation of plasmids containing a protospacer that matches the most highly transcribe crRNA in the native *L. jensenii* Type II CRISPSR array. From left to right, four different plasmids were transformed into *L jensenii*: an empty pTRK563 vector, a construct with the correct protospacer but an incorrect PAM, the correct PAM but a protospacer that is not in the array, and the correct protospacer with the PAM that demonstrated the most interference targeting and cell death.
Figure 23:
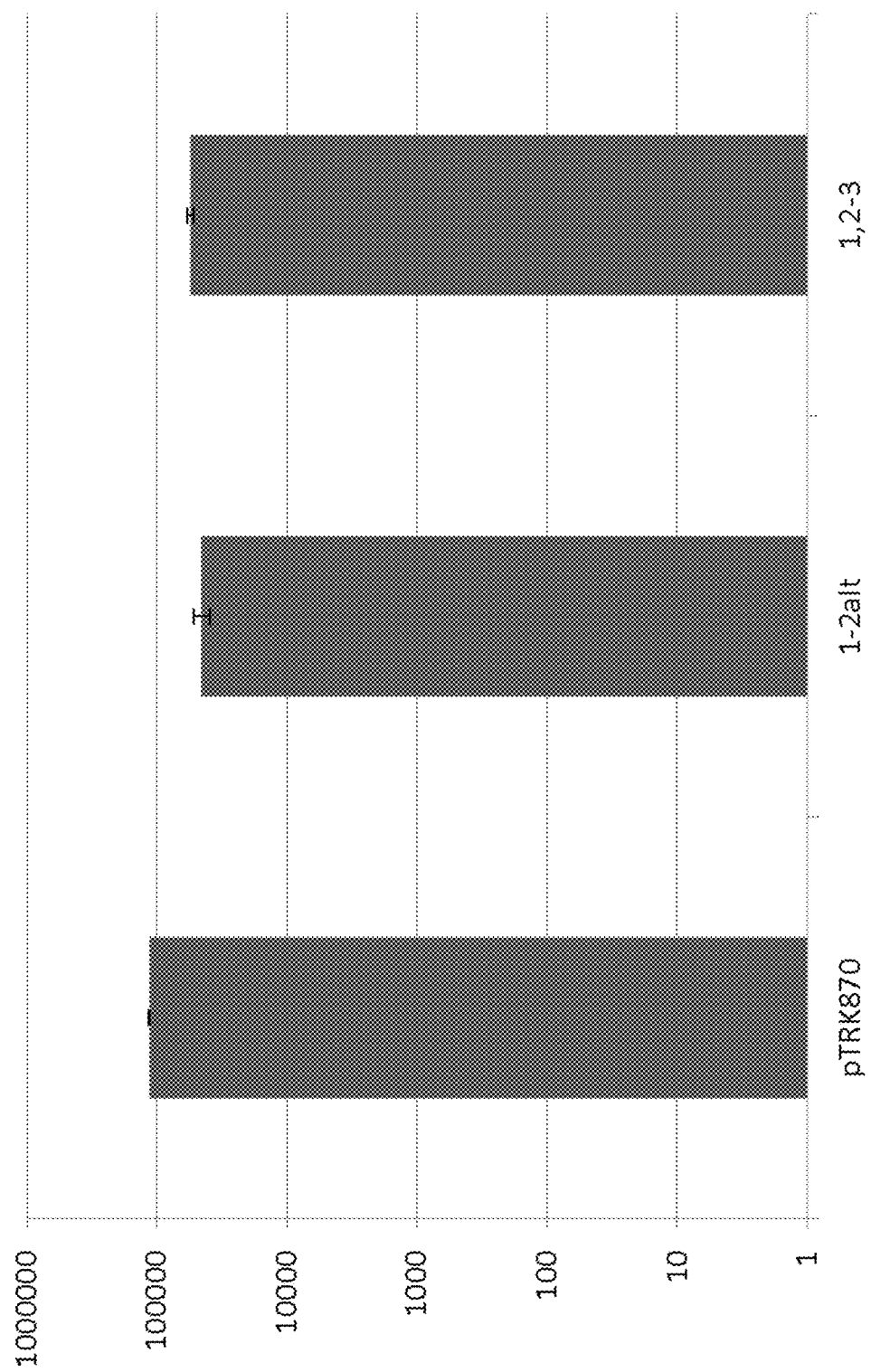
FIG. 23 shows targeted self-killing using the native Type I system in *Lactobacillus casei* NCK 125. Two targets were designed in the 16s rDNA gene. The PAM 5'-YAA-3' was predicted using the native spacer sequences in the organism. An artificial array containing the native Type I leader, repeats and the selected spacers was cloned into pTRK870. The constructs introduced included an empty vector (pTRK563) and two different artificial arrays: one containing a single spacer targeting the + strand in the 16s gene (1-2 alt) and the other array containing the original spacer targeting the + strand but containing an additional spacer targeting the − strand in the 16s gene (1, 2-3). The reported values represent the mean±SEM of three independent replicates.

Plasmids were transformed into *L. jensenii* each carrying different constructs as follows: a construct comprising an empty pTRK563 vector, a construct with the correct protospacer but an incorrect PAM, a construct with a correct PAM but a protospacer that is not in the array, and a construct having a correct protospacer with a correct PAM. The results are shown in FIG. 22. The plasmid having a correct protospacer and correct PAM showed substantially more interference targeting and cell death.

Example 15. Targeted Killing of *Lactobacillus casei* NCK 125 Using a Type I CRISPR-Cas System FIG. 21 provides an exemplary Type I CRISPR-Cas guide for *L. casei*, which comprises the sequence of the native Type I leader and repeat found in *L. casei* NCK 125. PAM 5'-YAA-3' was predicted using the native spacer sequences in the organism. The artificial array contains a spacer that targets the 16s rDNA gene in the host genome. The results are provided in FIG. 22, which shows a significant reduction between the empty vector and two different artificial arrays: one of which contains a single spacer targeting the + strand in the 16s gene (1-2 alt) and the other containing the original spacer targeting the + strand but containing an additional spacer targeting the − strand in the 16s gene (1, 2-3).

CRISPR-Cas systems as described herein may be used for, for example, (i) targeted reduction of pathogens in the case of either medical intervention (e.g., pathogens including but not limited to, fungi, nematodes, protozoa (e.g., malaria), cestodes, coccidia (microsporidia), trematodes, pentastomids, acanthocephalans, arthropods, and the like); (ii) for protection of consumables (food systems, animals, crops); (iii) for control and/or removal of undesirable organisms from industrial fermentative processes (raw materials, processing equipment, starter cultures) and (iv) for control of environmental microbial consortia to impact ecosystems and/or chemical cycles as well as for remediation.

TABLE 1

Bacterial Strains and Plasmids

| | Description | Original Reference |
|---|---|---|
| Strain designation | | |
| *E. coli* EC1000 | Host for pORI plasmids, chromosomal repA+ (pWVO1), Km$^R$ Host for pTRK935 | 47 |
| *S. thermophilus* LMD-9 | Wild-type | 40 |
| *S thermophilus* LMD-9 with pTRK669 | Wild-type, RepA+ and Cm$^R$ conferred by pTRK669 | This study |
| Plasmids | | |
| pORI28 | Broad range non-replicative vector, Em$^R$ | 47 |
| pTRK669 | Ts-helper plasmid repA+, Cm$^R$ | 44 |
| pCRISPR1::lacZ | pORI28::CRISPR1-Leader-RSR-lacZ N-terminus spacer | This study |
| pCRISPR3::lacZ | pORI28::CRISPR1-Leader-RSR-lacZ active site spacer | This study |
| pCRISPR3::ABC | pORI28::CRISPR1-Leader-RSR-ABC spacer | This study |
| pCRISPR3::Cu | pORI28::CRISPR1-Leader-RSR-Cu efflux spacer | This study |
| pCRISPR3::prts | pORI28::CRISPR1-Leader-RSR-prts spacer | This study |
| pCRISPR3::lacZ | pORI28::CRISPR3-Leader-RSR-lacZ N-terminus spacer | This study |
| pCRISPR1::Non-self | pORI28::CRISPR1-Leader-RSR-non self spacer | This study |

TABLE 2

Primers

| Primer Name | Sequence | Function |
|---|---|---|
| C1_N-term_F | CAAGAACAGTTATTGATTTTATAATCACTATGTGGGTATGAAAATCTCAAAAATCATTTGAGGTTTT TGTACTCTCAAGATTTAAGTAACTGTACAACATTAAGAGATTGTCTTAACTT SEQ ID NO: 51 | Template for SOE-PCR |
| C3_N-term | AGCGGATAACAATTTCACGTTTTGGAACCATTCGAAACAACACAGCTCTAAAACTCAGAAAATTCTT CAAGAGATTCAAAATACTGTTTTGGAACCATTCGAAACAACACAGCTCTAAAACCTCGTAGGATATC TTTTCTAC SEQ ID NO: 52 | Template for SOE-PCR |
| C1_N-term_R | AGCGGATAACAATTTCACGTTGTACAGTTACTTAAATCTTGAGAGTACAAAAACAGGGGAGATGAAG TTAAGACAATCTCTTAATGT SEQ ID NO: 53 | Template for SOE-PCR |
| C3_A-site | AGCGGATAACAATTTCACGTTTTGGAACCATTCGAAACAACACAGCTCTAAAACGAAGTCTTGGTCT TCCAACCAGCTTGCTGTAGTTTTGGAACCATTCGAAACAACACAGCTCTAAAACCTCGTAGGATATC TTTTCTAC SEQ ID NO: 54 | Template for SOE-PCR |
| C3_ABC | AGCGGATAACAATTTCACGTTTTGGAACCATTCGAAACAACACAGCTCTAAAACGATAACACGAGATAA AACATCCAGCCCACCGTTTTGGAACCATTCGAAACAACACAGCTCTAAAACctcgtaggatatcttttc tac SEQ ID NO: 55 | |
| C3_prtS | AGCGGATAACAATTTCACGTTTTGGAACCATTCGAAACAACACAGCTCTAAAACGTTGTAGCTTTGAGG TCTGAGAATACACGCGTTTTGGAACCATTCGAAACAACACAGCTCTAAAACctcgtaggatatctttc tac SEQ ID NO: 56 | |
| C3_Cu | AGCGGATAACAATTTCACGTTTTGGAACCATTCGAAACAACACAGCTCTAAAACGATTGCTCAATCA ATCGTTTCAGCTGCTAAGTTTTGGAACCATTCGAAACAACACAGCTCTAAAACctcgtaggatatct tttctac SEQ ID NO: 57 | |
| C3LF | AGCAGGGATCCTGGTAATAAGTATAGATAGTCTTG SEQ ID NO: 58 | Amplify Sth3 Leader from gDNA |
| C3LR | CTCGTAGGATATCTTTTCTAC SEQ ID NO: 59 | Amplify Sth3 Leader from gDNA |
| C1F | AGCAGGGATCCCAAGAACAGTTATTGATTTTATAATC SEQ ID NO: 60 | CRISPR1 SOE-PCR Forward |
| C3F | AGCAGGGATCCTGGTAATAAGTATAGATAGTCTTG SEQ ID NO: 61 | CRISPR3 SOE-PCR Foward |
| C1C3R | TGCTGGAGCTCGTGAAATTGTTATCCGCT SEQ ID NO: 62 | CRISPR1 and CRISPR3 SOE-PCR Reverse |

TABLE 2-continued

Primers

| Primer Name | Sequence | | Function |
|---|---|---|---|
| 1193F | TTGAACACTAGGAACCTCATA | SEQ ID NO: 63 | Deletion junction amplification |
| 1193R | CGTAAGGTTTTGATGACTCAAG | SEQ ID NO: 64 | Deletion junction amplification |
| pORI28F | TTGGTTGATAATGAACTGTGCTG | SEQ ID NO: 65 | Sequencing MCS of pORI28 |
| pORI28R | TTGTTGTTTTTATGATTACAAAGTGA | SEQ ID NO: 66 | Sequencing MCS of pORI28 |

TABLE 3

Putative expendable genomic islands and islets.

| Genomic island | ORF region | Length kbp | GC content % | Notable genes | IS family |
|---|---|---|---|---|---|
| 1 | STER_139-STER_148 | 7.81 | 37.1 | Oligopeptide transporters | IS6 |
| 2 | STER_840-STER_848 | 10.29 | 39.9 | Proteinase PrtS | ISSth16/IS1167 |
| 3 | STER_881-STER_888 | 8.71 | 39.3 | Copper efflux | IS1191 |
| 4 | STER_1277-STER_1380 | 101.76 | 37.2 | Lactose catabolism, 2-component reg., bacteriocin synthesis, ABC transporters | IS1193 |

TABLE 4

Homologues to about 239 essential ORFs identified in S. thermophilus.

| Genome_part | STER | start | stop | direction | |
|---|---|---|---|---|---|
| CSTER | 1 | 101 | 1465 | + | chromosomal replication initiation prot. DnaA |
| CSTER | 2 | 1620 | 2756 | + | DNA polymerase III subunit beta |
| CSTER | 6 | 5818 | 6387 | + | Peptidyl-tRNA hydrolase |
| CSTER | 9 | 10331 | 10702 | + | cell-cycle prot. |
| CSTER | 12 | 12122 | 13387 | + | tRNA(Ile)-lysidine synthetase, MesJ |
| CSTER | 13 | 13469 | 14011 | + | Hypoxanthine-guanine phosphoribosyltransferase |
| CSTER | 40 | 25595 | 26425 | + | Cell shape-determining protein MreC |
| CSTER | 43 | 28617 | 29582 | + | ribose-phosphate pyrophosphokinase |
| CSTER | 47 | 32842 | 33846 | + | put. glycerol-3-phosphate acyltransferase |
| CSTER | 48 | 33846 | 34091 | + | acyl carrier prot. |
| CSTER | 65 | 53036 | 54727 | − | Arginyl-tRNA synthetase |
| CSTER | 95 | 72798 | 77192 | + | DNA polymerase III PolC |
| CSTER | 105 | 82956 | 83723 | + | 30S ribosomal prot. S2 |
| CSTER | 106 | 83841 | 84881 | + | Translation elongation factor Ts |
| CSTER | 117 | 97363 | 98706 | + | Cysteinyl-tRNA synthetase |
| CSTER | 127 | 104406 | 104852 | + | 50S ribosomal prot. L13 |
| CSTER | 128 | 104880 | 105272 | + | 30S ribosomal prot. S9 |
| CSTER | 193 | 159363 | 160967 | + | CTP synthetase |
| CSTER | 199 | 166439 | 166897 | − | conserv. hyp. prot. |
| CSTER | 208 | 176203 | 176472 | + | 30S ribosomal prot. S15 |
| CSTER | 217 | 183028 | 184185 | + | undecaprenyl pyrophosphate phosphatase |
| CSTER | 218 | 184346 | 185116 | + | ABC transporter ATPase |
| CSTER | 219 | 185153 | 186415 | + | hyp. prot. |
| CSTER | 220 | 186469 | 187701 | + | put. aminotransferase (class V) |
| CSTER | 221 | 187688 | 188122 | + | NifU fam. prot. |
| CSTER | 245 | 208199 | 208993 | + | phosphatidate cytidylyltransferase |
| CSTER | 247 | 210343 | 212205 | + | Prolyl-tRNA synthetase |
| CSTER | 252 | 215735 | 216022 | + | Co-chaperonin GroES (HSP10) |
| CSTER | 253 | 216071 | 217690 | + | Chaperonin GroEL (HSP60 family) |
| CSTER | 261 | 224055 | 224204 | + | 50S ribosomal prot. L33 |
| CSTER | 262 | 224216 | 224392 | + | Preprotein translocase subunit SecE |
| CSTER | 268 | 227616 | 230117 | + | Leucyl-tRNA synthetase |

TABLE 4-continued

Homologues to about 239 essential ORFs identified in S. thermophilus.

| CSTER | 273 | 232342 | 233796 | + | nicotinate phosphoribosyltransferase |
|---|---|---|---|---|---|
| CSTER | 274 | 233808 | 234629 | + | NAD synthetase |
| CSTER | 286 | 248252 | 249580 | + | UDP-N-acetylmuramate-alanine ligase |
| CSTER | 302 | 260849 | 261664 | + | Glutamate racemase |
| CSTER | 307 | 264328 | 265041 | + | segregation and condensation prot. A |
| CSTER | 308 | 265034 | 265615 | + | segregation and condensation prot. B |
| CSTER | 313 | 269788 | 270297 | + | rRNA methytransferase |
| CSTER | 349 | 303983 | 305959 | + | Transketolase |
| CSTER | 357 | 312857 | 314032 | + | chromosome replication initiation/membrane attachment protein DnaB |
| CSTER | 358 | 314036 | 314938 | + | primosomal prot. DnaI |
| CSTER | 359 | 315044 | 316354 | + | GTP-binding prot. EngA |
| CSTER | 368 | 321054 | 322394 | − | Seryl-tRNA synthetase |
| CSTER | 376 | 329673 | 330116 | + | conserved hyp. prot. |
| CSTER | 380 | 332545 | 333732 | + | Transcription elongation factor |
| CSTER | 383 | 334363 | 337194 | + | Translation initiation factor IF-2 |
| CSTER | 387 | 339864 | 341309 | − | UDP-N-acetylmuramoylalanyl-D-glutamate--2,6-diaminopimelate ligase |
| CSTER | 419 | 364962 | 365894 | + | put. manganese-dependent inorganic pyrophosphatase |
| CSTER | 430 | 375355 | 375579 | + | acyl carrier prot. |
| CSTER | 432 | 376667 | 377593 | + | acyl-carrier-protein S-malonyltransferase |
| CSTER | 433 | 377606 | 378340 | + | 3-ketoacyl-(acyl-carrier-protein) reductase |
| CSTER | 434 | 378401 | 379633 | + | 3-oxoacyl-(acyl carrier protein) synthase II |
| CSTER | 435 | 379637 | 380125 | + | acetyl-CoA carboxylase biotin carboxyl carrier protein subunit |
| CSTER | 437 | 380667 | 382037 | + | acetyl-CoA carboxylase biotin carboxylase subunit |
| CSTER | 438 | 382043 | 382909 | + | acetyl-CoA carboxylase subunit beta |
| CSTER | 439 | 382906 | 383676 | + | acetyl-CoA carboxylase subunit alpha |
| CSTER | 442 | 385819 | 387417 | + | conserved hyp. prot. |
| CSTER | 455 | 402156 | 402470 | + | 50S ribosomal prot. L21 |
| CSTER | 456 | 402507 | 402797 | + | 50S ribosomal prot. L27 |
| CSTER | 460 | 405038 | 405805 | + | Dihydrodipicolinate reductase |
| CSTER | 461 | 405802 | 407010 | + | tRNA CCA-pyrophosphorylase |
| CSTER | 475 | 422256 | 422813 | + | Ribosome recycling factor |
| CSTER | 485 | 430547 | 432550 | + | Methyonyl-tRNA synthetase |
| CSTER | 492 | 438748 | 439890 | + | protease maturation prot. precursor |
| CSTER | 493 | 440232 | 442850 | + | Alanyl-tRNA synthetase |
| CSTER | 513 | 460453 | 463104 | + | Valyl-tRNA synthetase |
| CSTER | 523 | 469888 | 471168 | + | cell division prot. FtsW |
| CSTER | 524 | 471406 | 472602 | + | elongation factor Tu |
| CSTER | 525 | 472851 | 473609 | + | Triosephosphate isomerase |
| CSTER | 526 | 473848 | 474477 | + | Thymidylate kinase |
| CSTER | 527 | 474486 | 475361 | + | DNA polymerase III subunit delta' |
| CSTER | 539 | 484827 | 485744 | + | Glycyl-tRNA synthetase, alpha subunit |
| CSTER | 540 | 486028 | 488064 | + | Glycyl-tRNA synthetase, beta subunit |
| CSTER | 567 | 512413 | 512916 | + | 50S ribosomal prot. L10 |
| CSTER | 568 | 512991 | 513359 | + | 50S ribosomal prot. L7/L12 |
| CSTER | 603 | 548926 | 550308 | + | N-acetylglucosamine-1-phosphate uridyltransferase |
| CSTER | 623 | 566278 | 566781 | + | Dihydrofolate reductase |
| CSTER | 626 | 568210 | 568809 | + | GTPase EngB |
| CSTER | 632 | 573613 | 574254 | − | put. glycerol-3-phosphate acyltransferase PlsY |
| CSTER | 633 | 574392 | 576341 | + | DNA topoisomerase IV subunit B |
| CSTER | 634 | 576969 | 579434 | + | DNA topoisomerase IV subunit A |
| CSTER | 660 | 598871 | 599725 | + | methylenetetrahydrofolate dehydrogenase/methenyltetrahydrofolate cyclohydrolase |
| CSTER | 668 | 605570 | 606469 | + | GTPase Era |
| CSTER | 670 | 607313 | 607927 | + | Dephospho-CoA kinase |
| | 672 | 609192 | 609338 | | 50S ribosomal prot. L33 |

TABLE 4-continued

Homologues to about 239 essential ORFs identified in *S. thermophilus*.

| CSTER | 684 | 620012 | 621316 | + | Enolase |
|---|---|---|---|---|---|
| CSTER | 731 | 664470 | 665690 | − | put. cytosine-C5 specific DNA methylase |
| CSTER | 733 | 666939 | 668429 | − | Lysyl-tRNA synthetase (class II) |
| CSTER | 761 | 694548 | 695582 | + | DNA polymerase III delta subunit |
| CSTER | 773 | 704704 | 706056 | + | UDP-N-acetylmuramoyl-L-alanyl-D-glutamate synthetase |
| CSTER | 774 | 706060 | 707130 | + | N-acetylglucosaminyl transferase |
| CSTER | 775 | 707140 | 708264 | + | Cell division protein FtsQ |
| CSTER | 776 | 708388 | 709764 | + | Cell division protein FtsA |
| CSTER | 777 | 709793 | 711115 | + | Cell division protein FtsZ |
| CSTER | 783 | 714803 | 717592 | + | Isoleucyl-tRNA synthetase |
| CSTER | 787 | 720193 | 720459 | − | 50S ribosomal protein L31 |
| CSTER | 793 | 725315 | 726394 | + | Peptide chain release factor 1 |
| CSTER | 796 | 727911 | 729161 | + | serine hydroxymethyltransferase |
| CSTER | 833 | 760678 | 762396 | − | put. phosphoglucomutase |
| CSTER | 850 | 783500 | 783736 | − | 30S ribosomal prot. S20 |
| CSTER | 864 | 797961 | 799307 | + | Asparaginyl-tRNA synthetases |
| CSTER | 903 | 833853 | 835661 | + | D-fructose-6-phosphate amidotransferase |
| CSTER | 915 | 845349 | 846911 | + | Signal recognition particle prot. |
| CSTER | 919 | 848991 | 849845 | + | ribosomal biogenesis GTPase |
| CSTER | 923 | 852605 | 854749 | + | DNA topoisomerase I |
| CSTER | 994 | 915311 | 917623 | + | ATP-dependent DNA helicase PcrA |
| CSTER | 1034 | 959843 | 961231 | − | branched-chain alpha-keto acid dehydrogenase subunit E2 |
| CSTER | 1036 | 962412 | 963383 | − | acetoin dehydrogenase complex, E1 component, alpha subunit |
| CSTER | 1087 | 1007529 | 1007888 | − | 50S ribosomal prot. L20 |
| CSTER | 1088 | 1007945 | 1008145 | − | 50S ribosomal prot. L35 |
| CSTER | 1089 | 1008184 | 1008714 | − | Translation initiation factor 3 (IF-3) |
| CSTER | 1102 | 1017867 | 1018880 | − | Peptide chain release factor 2 |
| CSTER | 1115 | 1029796 | 1031136 | − | sensor histidine kinase |
| CSTER | 1116 | 1031129 | 1031836 | − | two-component response regulator |
| CSTER | 1123 | 1036555 | 1037826 | − | UDP-N-acetylglucosamine 1-carboxyvinyltransferase |
| CSTER | 1135 | 1049456 | 1050649 | − | S-adenosylmethionine synthetase |
| CSTER | 1136 | 1050929 | 1051867 | + | biotin-(acetyl-CoA carboxylase) ligase |
| CSTER | 1138 | 1052266 | 1053918 | − | DNA polymerase III, gamma/tau subunit |
| CSTER | 1144 | 1056546 | 1056893 | − | 50S ribosomal prot. L19 |
| CSTER | 1164 | 1073225 | 1074244 | − | 6-phosphofructokinase |
| CSTER | 1165 | 1074337 | 1077447 | − | DNA polymerase III, alpha subunit DnaE |
| CSTER | 1166 | 1077600 | 1078385 | − | Putative translation factor (SUA5) |
| CSTER | 1175 | 1085950 | 1086225 | − | histone-like DNA-binding prot. |
| CSTER | 1182 | 1091629 | 1092501 | − | Geranylgeranyl pyrophosphate synthase |
| CSTER | 1188 | 1095764 | 1096462 | − | DNA replication prot. DnaD |
| CSTER | 1193 | 1101272 | 1102201 | − | ribonuclease Z |
| CSTER | 1197 | 1105450 | 1106877 | − | cell division prot. |
| CSTER | 1230 | 1131390 | 1132742 | − | Phosphoglucosamine mutase |
| CSTER | 1248 | 1154457 | 1156616 | + | ribonucleotide-diphosphate reductase, alpha subunit |
| CSTER | 1249 | 1156775 | 1157737 | + | ribonucleotide-diphosphate reductase, beta subunit |
| CSTER | 1256 | 1161831 | 1164284 | − | DNA gyrase, A subunit |
| CSTER | 1267 | 1174041 | 1176449 | − | phenylalanyl-tRNA synthetase, beta subunit |
| CSTER | 1270 | 1177285 | 1178328 | − | Phenylalanyl-tRNA synthetase alpha subunit |
| CSTER | 1271 | 1178950 | 1182483 | − | chromosome segregation ATPase, SMC prot. |
| CSTER | 1272 | 1182486 | 1183175 | − | ribonuclease III |
| CSTER | 1273 | 1183332 | 1184267 | − | Dihydrodipicolinate synthase |
| CSTER | 1274 | 1184605 | 1185681 | − | Aspartate-semialdehyde dehydrogenase |
| CSTER | 1382 | 1293065 | 1294063 | − | Thioredoxin reductase |
| CSTER | 1383 | 1294065 | 1294784 | − | tRNA (guanine-N(1)-)-methyltransferase |
| CSTER | 1395 | 1303326 | 1304261 | − | methionyl-tRNA formyltransferase |
| CSTER | 1396 | 1304279 | 1306675 | − | primosome assembly protein PriA |
| CSTER | 1398 | 1307153 | 1307782 | − | Guanylate kinase |
| CSTER | 1399 | 1308015 | 1309406 | − | cell division prot. FtsY |
| CSTER | 1422 | 1330503 | 1331339 | − | inorganic polyphosphate/ATP-NAD kinase |

TABLE 4-continued

Homologues to about 239 essential ORFs identified in *S. thermophilus*.

| | | | | | |
|---|---|---|---|---|---|
| CSTER | 1425 | 1333019 | 1333990 | + | ribose-phosphate pyrophosphokinase |
| CSTER | 1426 | 1333994 | 1335106 | + | put. cysteine desulfurase |
| CSTER | 1448 | 1355769 | 1356878 | − | RNA polymerase sigma factor RpoD |
| CSTER | 1449 | 1356882 | 1358693 | − | DNA primase |
| CSTER | 1451 | 1359076 | 1359252 | − | 30S ribosomal prot. S21 |
| CSTER | 1464 | 1371306 | 1372619 | − | GTPase ObgE |
| CSTER | 1480 | 1387053 | 1389005 | − | DNA gyrase subunit B |
| CSTER | 1497 | 1401241 | 1402143 | − | UDP-N-acetylenolpyruvoylglucosamine reductase |
| CSTER | 1506 | 1409996 | 1410268 | − | 30S ribosomal prot. S16 |
| CSTER | 1512 | 1415065 | 1416078 | − | put. lipid kinase |
| CSTER | 1513 | 1416088 | 1418034 | − | NAD-dependent DNA ligase |
| CSTER | 1516 | 1419659 | 1420519 | − | methionine aminopeptidase |
| CSTER | 1519 | 1422447 | 1423709 | − | UDP-N-acetylglucosamine 1-carboxyvinyltransferase |
| CSTER | 1522 | 1426828 | 1427583 | − | 1-acyl-sn-glycerol-3-phosphate acyltransferase |
| CSTER | 1534 | 1439747 | 1441120 | − | UDP-N-acetylmuramoyl-tripeptide--D-alanyl-D-alanine ligase |
| CSTER | 1544 | 1447537 | 1448583 | − | D-alanyl-alanine synthetase A |
| CSTER | 1583 | 1483475 | 1484107 | − | nicotinic acid mononucleotide adenylyltransferase |
| CSTER | 1584 | 1484211 | 1484528 | − | put. RNA-binding prot. |
| CSTER | 1585 | 1484767 | 1485885 | − | GTP-binding prot. YqeH |
| CSTER | 1590 | 1488021 | 1489463 | − | aspartyl/glutamyl-tRNA amidotransferase subunit B |
| CSTER | 1591 | 1489463 | 1490929 | − | aspartyl/glutamyl-tRNA amidotransferase subunit A |
| CSTER | 1592 | 1490929 | 1491231 | − | aspartyl/glutamyl-tRNA amidotransferase subunit C |
| CSTER | 1615 | 1511378 | 1512298 | − | Thioredoxin reductase |
| CSTER | 1665 | 1554189 | 1555211 | − | phospho-N-acetylmuramoyl-pentapeptide-transferase |
| CSTER | 1666 | 1555213 | 1557480 | − | put. penicillin-binding protein 2X |
| CSTER | 1667 | 1557484 | 1557804 | − | cell division prot. FtsL |
| CSTER | 1701 | 1591284 | 1592387 | − | Alanine racemase |
| CSTER | 1702 | 1592408 | 1592767 | − | put. 4'-phosphopantetheinyl transferase |
| CSTER | 1705 | 1594955 | 1597504 | − | preprotein translocase subunit SecA |
| CSTER | 1726 | 1616337 | 1616576 | − | 30S ribosomal prot. S18 |
| CSTER | 1727 | 1616618 | 1617136 | − | single-strand DNA-binding prot. |
| CSTER | 1728 | 1617148 | 1617438 | − | 30S ribosomal prot. S6 |
| CSTER | 1745 | 1633808 | 1634821 | − | put. O-sialoglycoprotein endopeptidase |
| CSTER | 1747 | 1635236 | 1635922 | − | put. glycoprotein endopeptidase |
| CSTER | 1749 | 1636421 | 1638103 | + | mRNA degradation ribonucleases J1/J2 |
| CSTER | 1755 | 1642501 | 1643700 | − | phosphoglycerate kinase |
| CSTER | 1762 | 1648240 | 1650321 | − | translation elongation factor G |
| CSTER | 1763 | 1650542 | 1651012 | − | 30S ribosomal prot. S7 |
| CSTER | 1764 | 1651031 | 1651444 | − | 30S ribosomal prot. S12 |
| CSTER | 1770 | 1656078 | 1656950 | − | ribosome-associated GTPase |
| CSTER | 1776 | 1660099 | 1660413 | − | put. thioredoxin |
| CSTER | 1787 | 1670058 | 1670192 | − | 50S ribosomal prot. L34 |
| CSTER | 1790 | 1673060 | 1673395 | − | ribonuclease P |
| CSTER | 1793 | 1677296 | 1678750 | − | Glutamyl-tRNA synthetases |
| CSTER | 1797 | 1681106 | 1681795 | − | 50S ribosomal prot. L1 |
| CSTER | 1809 | 1690036 | 1691058 | + | Glycerol-3-phosphate dehydrogenase |
| CSTER | 1813 | 1693298 | 1694431 | − | Metal-dependent amidase/aminoacylase/carboxypeptidase |
| CSTER | 1814 | 1694510 | 1695208 | − | put. 2,3,4,5-tetrahydropyridine-2-carboxylate N-succinyltransferase |
| CSTER | 1821 | 1699209 | 1699601 | − | single-strand binding prot. |
| CSTER | 1844 | 1713286 | 1716924 | − | DNA-directed RNA polymerase subunit beta' |
| CSTER | 1845 | 1717025 | 1720606 | − | DNA-directed RNA polymerase subunit beta |
| CSTER | 1847 | 1723493 | 1724749 | + | Tyrosyl-tRNA synthetase |
| CSTER | 1876 | 1751169 | 1752050 | − | fructose-bisphosphate aldolase |
| CSTER | 1880 | 1755102 | 1755488 | − | 50S ribosomal prot. L17 |
| CSTER | 1881 | 1755506 | 1756444 | − | DNA-directed RNA polymerase alpha subunit |
| CSTER | 1882 | 1756493 | 1756876 | − | 30S ribosomal prot. S11 |

TABLE 4-continued

Homologues to about 239 essential ORFs identified in *S. thermophilus*.

| | | | | | |
|---|---|---|---|---|---|
| CSTER | 1883 | 1756904 | 1757269 | − | 30S ribosomal prot. S13 |
| CSTER | 1884 | 1757290 | 1757403 | − | 50S ribosomal prot. L36 |
| CSTER | 1885 | 1757429 | 1757647 | − | Translation initiation factor 1 (IF-1) |
| CSTER | 1886 | 1757765 | 1758421 | − | Adenylate kinase |
| CSTER | 1887 | 1758553 | 1759848 | − | preprot. translocase subunit SecY |
| CSTER | 1888 | 1759865 | 1760305 | − | 50S ribosomal prot. L15 |
| CSTER | 1889 | 1760433 | 1760615 | − | 50S ribosomal prot. L30 |
| CSTER | 1890 | 1760630 | 1761124 | − | 30S ribosomal prot. S5 |
| CSTER | 1891 | 1761143 | 1761499 | − | 50S ribosomal prot. L18 |
| CSTER | 1892 | 1761589 | 1762125 | − | 50S ribosomal prot. L6 |
| CSTER | 1893 | 1762252 | 1762650 | − | 30S ribosomal prot. S8 |
| CSTER | 1894 | 1762773 | 1762958 | − | 30S ribosomal prot. S14 |
| CSTER | 1895 | 1762976 | 1763518 | − | 50S ribosomal prot. L5 |
| CSTER | 1896 | 1763545 | 1763850 | − | 50S ribosomal prot. L24 |
| CSTER | 1897 | 1763931 | 1764299 | − | 50S ribosomal prot. L14 |
| CSTER | 1898 | 1764324 | 1764584 | − | 30S ribosomal prot. S17 |
| CSTER | 1899 | 1764612 | 1764818 | − | 50S ribosomal prot. L29 |
| CSTER | 1900 | 1764828 | 1765241 | − | 50S ribosomal prot. L16 |
| CSTER | 1901 | 1765245 | 1765898 | − | 30S ribosomal prot. S3 |
| CSTER | 1902 | 1765911 | 1766255 | − | 50S ribosomal prot. L22 |
| CSTER | 1903 | 1766271 | 1766549 | − | 30S ribosomal prot. S19 |
| CSTER | 1904 | 1766643 | 1767476 | − | 50S ribosomal prot. L2 |
| CSTER | 1905 | 1767494 | 1767790 | − | 50S ribosomal prot. L23 |
| CSTER | 1906 | 1767790 | 1768413 | − | 50S ribosomal prot. L4 |
| CSTER | 1907 | 1768438 | 1769064 | − | 50S ribosomal prot. L3 |
| CSTER | 1908 | 1769181 | 1769489 | − | 30S ribosomal prot. S10 |
| CSTER | 1936 | 1795296 | 1795484 | + | 50S ribosomal prot. L28 |
| CSTER | 1948 | 1805428 | 1807179 | − | Aspartyl-tRNA synthetase |
| CSTER | 1950 | 1807719 | 1808999 | − | Histidyl-tRNA synthetase |
| CSTER | 1953 | 1810651 | 1810833 | + | 50S ribosomal prot. L32 |
| CSTER | 1954 | 1810849 | 1810998 | + | 50S ribosomal prot. L33 |
| CSTER | 1973 | 1823718 | 1824329 | − | 30S ribosomal prot. S4 |
| CSTER | 1975 | 1824852 | 1826213 | − | replicative DNA helicase |
| CSTER | 1976 | 1826257 | 1826715 | − | 50S ribosomal prot. L9 |
| CSTER | 1979 | 1830931 | 1832052 | − | tRNA (5-methylaminomethyl-2-thiouridylate)-methyltransferase |
| CSTER | 1986 | 1838183 | 1838725 | − | Phosphatidylglycerophosphate synthase |
| CSTER | 1992 | 1843910 | 1845391 | − | inositol-5-monophosphate dehydrogenase |
| CSTER | 1993 | 1845568 | 1846590 | − | Tryptophanyl-tRNA synthetase II |

| Genome part | STER | query cover | e-value | aa id | *Bacillus subtilis* annotation |
|---|---|---|---|---|---|
| CSTER | 1 | 98% | 4.00E−124 | 44% | Chromosomal replication initiator protein DnaA |
| CSTER | 2 | 99% | 1.00E−88 | 39% | DNA polymerase III subunit beta dnan |
| CSTER | 6 | 97% | 1.00E−61 | 51% | |
| CSTER | 9 | 94% | 1.00E−05 | 22% | Cell division protein DivIC |
| CSTER | 12 | 92% | 3.00E−40 | 32% | tRNA(Ile)-lysidine synthase tils |
| CSTER | 13 | 99% | 2.00E−82 | 63% | Hypoxanthine-guanine phosphoribosyltransferase hprt |
| CSTER | 40 | 94% | 1.00E−22 | 28% | Cell shape-determining protein MreC |
| CSTER | 43 | 97% | 3.00E−145 | 65% | Ribose-phosphate pyrophosphokinase prs |
| CSTER | 47 | 94% | 9.00E−124 | 54% | Phosphate acyltransferase PlsX |
| CSTER | 48 | 76% | 1.00E−08 | 40% | Acyl carrier protein |
| CSTER | 65 | 98% | 6.00E−52 | 28% | |
| CSTER | 95 | 99% | 0.00E+00 | 51% | DNA polymerase III PolC-type |
| CSTER | 105 | 96% | 1.00E−118 | 69% | |
| CSTER | 106 | 97% | 8.00E−72 | 44% | |
| CSTER | 117 | 99% | 1.00E−178 | 54% | |
| CSTER | 127 | 99% | 9.00E−57 | 57% | |
| CSTER | 128 | 100% | 3.00E−59 | 68% | |
| CSTER | 193 | 99% | 0.00E+00 | 68% | CTP synthase pyrg |
| CSTER | 199 | 81% | 2.00E−07 | 28% | Protein NrdI |
| CSTER | 208 | 100% | 6.00E−38 | 63% | |
| CSTER | 217 | 98% | 2.00E−68 | 38% | Probable undecaprenyl-phosphate N-acetylglucosaminyl 1-phosphate transferase tagO |
| CSTER | 218 | 95% | 8.00E−130 | 71% | Vegetative protein 296 sufC |
| CSTER | 219 | 97% | 4.00E−111 | 42% | FeS cluster assembly protein SufD |
| CSTER | 220 | 98% | 0.00E+00 | 60% | Cysteine desulfurase SufS |
| CSTER | 221 | 95% | 3.00E−48 | 51% | Zinc-dependent sulfurtransferase SufU |
| CSTER | 245 | 98% | 3.00E−67 | 41% | Phosphatidate cytidylyltransferase |

TABLE 4-continued

Homologues to about 239 essential ORFs identified in S. thermophilus.

| CSTER | 247 | 98% | 0.00E+00 | 50% | |
|---|---|---|---|---|---|
| CSTER | 252 | 97% | 1.00E−18 | 43% | |
| CSTER | 253 | 98% | 0.00E+00 | 75% | |
| CSTER | 261 | 97% | 9.00E−12 | 50% | |
| CSTER | 262 | 81% | 1.40E+00 | 21% | Protein translocase subunit SecE |
| CSTER | 268 | 99% | 0.00E+00 | 70% | |
| CSTER | 273 | 97% | 0.00E+00 | 63% | Nicotinate phosphoribosyltransferase pncb |
| CSTER | 274 | 100% | 9.00E−109 | 59% | NH(3)-dependent NAD(+) synthetase nade |
| CSTER | 286 | 99% | 3.00E−170 | 55% | UDP-N-acetylmuramate--L-alanine ligase murC |
| CSTER | 302 | 94% | 7.00E−83 | 48% | Glutamate racemase 1 racE |
| CSTER | 307 | 93% | 5.00E−37 | 39% | Segregation and condensation protein A |
| CSTER | 308 | 94% | 9.00E−36 | 40% | Segregation and condensation protein B |
| CSTER | 313 | 96% | 3.00E−58 | 51% | rRNA methyltransferase |
| CSTER | 349 | 98% | 0.00E+00 | 58% | Transketolase tkt |
| CSTER | 357 | 63% | 3.00E−02 | 18% | Replication initiation and membrane attachment protein |
| CSTER | 358 | 99% | 7.00E−58 | 35% | Primosomal protein DnaI |
| CSTER | 359 | 100% | 0.00E+00 | 67% | GTPase Der |
| CSTER | 368 | 100% | 0.00E+00 | 63% | |
| CSTER | 376 | 89% | 6.00E−33 | 43% | tRNA threonylcarbamoyladenosine biosynthesis protein TsaE |
| CSTER | 380 | 90% | 2.00E−113 | 46% | Transcription termination/antitermination protein NusA |
| CSTER | 383 | 99% | 0.00E+00 | 55% | |
| CSTER | 387 | 92% | 3.00E−52 | 29% | UDP-N-acetylmuramoyl-L-alanyl-D-glutamate--2,6-diaminopimelate ligase murE |
| CSTER | 419 | 99% | 3.00E−125 | 58% | Manganese-dependent inorganic pyrophosphatase ppac |
| CSTER | 430 | 93% | 5.00E−14 | 49% | Acyl carrier protein |
| CSTER | 432 | 95% | 3.00E−86 | 47% | Malonyl CoA-acyl carrier protein transacylase |
| CSTER | 433 | 99% | 6.00E−79 | 47% | 3-oxoacyl-[acyl-carrier-protein] reductase FabG |
| CSTER | 434 | 99% | 1.00E−133 | 48% | 3-oxoacyl-[acyl-carrier-protein] synthase 2 |
| CSTER | 435 | 98% | 9.00E−26 | 37% | Biotin carboxyl carrier protein of acetyl-CoA carboxylase |
| CSTER | 437 | 98% | 0.00E+00 | 60% | Biotin carboxylase 1 |
| CSTER | 438 | 94% | 8.00E−98 | 51% | Acetyl-coenzyme A carboxylase carboxyl transferase subunit beta |
| CSTER | 439 | 76% | 2.00E−81 | 53% | Acetyl-coenzyme A carboxylase carboxyl transferase subunit alpha |
| CSTER | 442 | 98% | 0.00E+00 | 58% | Ribonuclease Y ymda |
| CSTER | 455 | 99% | 2.00E−44 | 66% | |
| CSTER | 456 | 95% | 5.00E−47 | 79% | |
| CSTER | 460 | 98% | 7.00E−95 | 53% | 4-hydroxy-tetrahydrodipicolinate reductase dapb |
| CSTER | 461 | 98% | 6.00E−86 | 40% | CCA-adding enzyme |
| CSTER | 475 | 100% | 2.00E−68 | 56% | |
| CSTER | 485 | 98% | 0.00E+00 | 58% | |
| CSTER | 492 | 91% | 6.00E−11 | 26% | Foldase protein PrsA |
| CSTER | 493 | 99% | 0.00E+00 | 52% | |
| CSTER | 513 | 99% | 0.00E+00 | 63% | |
| CSTER | 523 | 93% | 4.00E−59 | 34% | Putative lipid II flippase FtsW |
| CSTER | 524 | 99% | 0.00E+00 | 76% | |
| CSTER | 525 | 97% | 8.00E−109 | 62% | Triosephosphate isomerase tpia |
| CSTER | 526 | 96% | 4.00E−73 | 55% | Thymidylate kinase tmk |
| CSTER | 527 | 96% | 8.00E−41 | 33% | DNA polymerase III subunit delta' |
| CSTER | 539 | 97% | 4.00E−169 | 74% | |
| CSTER | 540 | 97% | 0.00E+00 | 45% | |
| CSTER | 567 | 100% | 7.00E−61 | 57% | |
| CSTER | 568 | 100% | 4.00E−38 | 67% | |
| CSTER | 603 | 97% | 3.00E−164 | 52% | Bifunctional protein GlmU |
| CSTER | 623 | 94% | 8.00E−34 | 38% | Dihydrofolate reductase dfra |
| CSTER | 626 | 96% | 7.00E−92 | 63% | Probable GTP-binding protein EngB |
| CSTER | 632 | 90% | 3.00E−40 | 46% | Glycerol-3-phosphate acyltransferase plsy |
| CSTER | 633 | 97% | 0.00E+00 | 71% | DNA topoisomerase 4 subunit B |
| CSTER | 634 | 95% | 0.00E+00 | 54% | DNA topoisomerase 4 subunit |
| CSTER | 660 | 99% | 2.00E−109 | 56% | Bifunctional protein FolD |
| CSTER | 668 | 98% | 5.00E−143 | 64% | GTPase Era |

TABLE 4-continued

Homologues to about 239 essential ORFs identified in *S. thermophilus*.

| | | | | | |
|---|---|---|---|---|---|
| CSTER | 670 | 95% | 2.00E−50 | 45% | Dephospho-CoA kinase coae |
| | 672 | 97% | 1.00E−16 | 52% | |
| CSTER | 684 | 100% | 0.00E+00 | 70% | Enolase eno |
| CSTER | 731 | 60% | 5.00E−16 | 31% | Probable BsuMI modification methylase subunit YdiO |
| CSTER | 733 | 97% | 0.00E+00 | 64% | |
| CSTER | 761 | 84% | 2.00E−37 | 33% | Uncharacterized protein YqeN |
| CSTER | 773 | 98% | 8.00E−147 | 49% | UDP-N-acetylmuramoylalanine--D-glutamate ligase murD |
| CSTER | 774 | 95% | 3.00E−30 | 27% | UDP-N-acetylglucosamine--N-acetylmuramyl-(pentapeptide) pyrophosphoryl-undecaprenol N-acetylglucosamine transferase murG |
| CSTER | 775 | 79% | 4.00E−15 | 26% | Cell division protein DivIB |
| CSTER | 776 | 84% | 4.00E−103 | 44% | Cell division protein FtsA |
| CSTER | 777 | 92% | 2.00E−123 | 53% | Cell division protein FtsZ |
| CSTER | 783 | 99% | 0.00E+00 | 58% | |
| CSTER | 787 | 100% | 1.00E−22 | 50% | |
| CSTER | 793 | 99% | 6.00E−158 | 59% | |
| CSTER | 796 | 97% | 2.00E−171 | 60% | Serine hydroxymethyltransferase glya |
| CSTER | 833 | 98% | 0.00E+00 | 47% | Phosphoglucomutase pgm |
| CSTER | 850 | 94% | 1.00E−13 | 46% | |
| CSTER | 864 | 99% | 4.00E−180 | 56% | |
| CSTER | 903 | 100% | 0.00E+00 | 59% | Glutamine--fructose-6-phosphate aminotransferase [isomerizing] glmS |
| CSTER | 915 | 95% | 2.00E−178 | 57% | Signal recognition particle protein |
| CSTER | 919 | 98% | 8.00E−101 | 50% | Ribosome biogenesis GTPase rbga |
| CSTER | 923 | 98% | 0.00E+00 | 64% | DNA topoisomerase 1 |
| CSTER | 994 | 99% | 0.00E+00 | 54% | ATP-dependent DNA helicase PcrA |
| CSTER | 1034 | 99% | 5.00E−69 | 34% | Dihydrolipoyllysine-residue succinyltransferase component of 2-oxoglutarate dehydrogenase complex odhb |
| CSTER | 1036 | 81% | 3.00E−33 | 28% | Pyruvate dehydrogenase E1 component subunit alpha pdha |
| CSTER | 1087 | 85% | 2.00E−56 | 80% | |
| CSTER | 1088 | 100% | 1.00E−23 | 62% | |
| CSTER | 1089 | 98% | 2.00E−63 | 60% | |
| CSTER | 1102 | 91% | 2.00E−137 | 57% | |
| CSTER | 1115 | 97% | 4.00E−117 | 71% | Transcriptional regulatory protein YycF |
| CSTER | 1116 | 68% | 2.00E−120 | 47% | Sensor histidine kinase YycG |
| CSTER | 1123 | 96% | 2.00E−172 | 59% | UDP-N-acetylglucosamine 1-carboxyvinyltransferase 1 muraa |
| CSTER | 1135 | 97% | 0.00E+00 | 67% | S-adenosylmethionine synthase metk |
| CSTER | 1136 | 92% | 4.00E−44 | 33% | Bifunctional ligase/repressor BirA |
| CSTER | 1138 | 93% | 3.00E−137 | 44% | DNA polymerase III subunit gamma/tau Dnax |
| CSTER | 1144 | 100% | 2.00E−61 | 77% | |
| CSTER | 1164 | 93% | 4.00E−124 | 61% | ATP-dependent 6-phosphofructokinase pfka |
| CSTER | 1165 | 96% | 0.00E+00 | 35% | DNA polymerase III subunit alpha dnae |
| CSTER | 1166 | 42% | 3.00E−04 | 24% | ywlC unknown conserved protein with a putative RNA binding motif TW |
| CSTER | 1175 | 95% | 4.00E−40 | 72% | DNA-binding protein HU 1 |
| CSTER | 1182 | 89% | 5.00E−58 | 44% | Farnesyl diphosphate synthase ispa yqid |
| CSTER | 1188 | 85% | 1.00E−07 | 22% | DNA replication protein DnaD |
| CSTER | 1193 | 99% | 2.00E−105 | 50% | Ribonuclease Z rnz |
| CSTER | 1197 | 88% | 2.00E−57 | 38% | Rod shape-determining protein RodA |
| CSTER | 1230 | 100% | 0.00E+00 | 63% | Phosphoglucosamine mutase ybbt glnM |
| CSTER | 1248 | 98% | 0.00E+00 | 47% | Ribonucleoside-diphosphate reductase subunit alpha nrde |
| CSTER | 1249 | 97% | 8.00E−98 | 49% | Ribonucleoside-diphosphate reductase subunit beta nrdf |
| CSTER | 1256 | 98% | 0.00E+00 | 62% | DNA gyrase subunit A |
| CSTER | 1267 | 99% | 0.00E+00 | 47% | |
| CSTER | 1270 | 98% | 3.00E−161 | 62% | |
| CSTER | 1271 | 99% | 0.00E+00 | 37% | Chromosome partition protein Smc |
| CSTER | 1272 | 89% | 4.00E−68 | 47% | Ribonuclease 3 |

TABLE 4-continued

Homologues to about 239 essential ORFs identified in *S. thermophilus*.

| | | | | | |
|---|---|---|---|---|---|
| CSTER | 1273 | 93% | 5.00E−88 | 47% | 4-hydroxy-tetrahydrodipicolinate synthase dapA |
| CSTER | 1274 | 99% | 1.00E−143 | 58% | Aspartate-semialdehyde dehydrogenase asd |
| CSTER | 1382 | 97% | 7.00E−113 | 50% | Ferredoxin--NADP reductase 2 yumc |
| CSTER | 1383 | 100% | 6.00E−87 | 56% | tRNA (guanine-N(1)-)-methyltransferase |
| CSTER | 1395 | 96% | 5.00E−98 | 49% | |
| CSTER | 1396 | 99% | 0.00E+00 | 48% | Primosomal protein N PriA |
| CSTER | 1398 | 98% | 5.00E−87 | 59% | Guanylate kinase gmk |
| CSTER | 1399 | 97% | 8.00E−121 | 55% | Signal recognition particle receptor FtsY |
| CSTER | 1422 | 100% | 5.00E−78 | 44% | NAD kinase 1 ppnk |
| CSTER | 1425 | 100% | 4.00E−113 | 54% | Ribose-phosphate pyrophosphokinase prs |
| CSTER | 1426 | 98% | 2.00E−115 | 47% | Putative cysteine desulfurase IscS |
| CSTER | 1448 | 93% | 6.00E−167 | 70% | RNA polymerase sigma factor SigA |
| CSTER | 1449 | 68% | 9.00E−86 | 37% | DNA primase DnaG |
| CSTER | 1451 | 98% | 3.00E−29 | 89% | |
| CSTER | 1464 | 100% | 0.00E+00 | 67% | GTPase ObgE |
| CSTER | 1480 | 100% | 0.00E+00 | 68% | DNA gyrase subunit B |
| CSTER | 1497 | 98% | 1.00E−66 | 40% | UDP-N-acetylenolpyruvoylglucosamine reductase murB |
| CSTER | 1506 | 100% | 5.00E−42 | 67% | |
| CSTER | 1512 | 95% | 1.00E−96 | 51% | Diacylglycerol kinase dagK |
| CSTER | 1513 | 97% | 0.00E+00 | 55% | DNA ligase LigA |
| CSTER | 1516 | 99% | 6.00E−56 | 37% | |
| CSTER | 1519 | 96% | 6.00E−125 | 46% | UDP-N-acetylglucosamine 1-carboxyvinyltransferase 1 muraa |
| CSTER | 1522 | 92% | 1.00E−29 | 32% | 1-acyl-sn-glycerol-3-phosphate acyltransferase plsC |
| CSTER | 1534 | 98% | 2.00E−98 | 38% | UDP-N-acetylmuramoyl-tripeptide--D-alanyl-D-alanine ligase murF |
| CSTER | 1544 | 98% | 2.00E−95 | 42% | D-alanine--D-alanine ligase ddl |
| CSTER | 1583 | 98% | 2.00E−62 | 44% | Nicotinate-nucleotide adenylyltransferase nadd |
| CSTER | 1584 | 95% | 1.00E−24 | 50% | Probable RNA-binding protein YqeI |
| CSTER | 1585 | 100% | 6.00E−163 | 59% | Uncharacterized protein YqeH |
| CSTER | 1590 | 99% | 0.00E+00 | 63% | |
| CSTER | 1591 | 99% | 0.00E+00 | 59% | |
| CSTER | 1592 | 97% | 1.00E−18 | 41% | |
| CSTER | 1615 | 95% | 3.00E−126 | 58% | Thioredoxin reductase trxb |
| CSTER | 1665 | 92% | 1.00E−66 | 41% | Phospho-N-acetylmuramoyl-pentapeptide-transferase mray |
| CSTER | 1666 | 90% | 9.00E−88 | 32% | Penicillin-binding protein 2B |
| CSTER | 1667 | | | | |
| CSTER | 1701 | 93% | 1.00E−98 | 43% | Alanine racemase 1 alr |
| CSTER | 1702 | 97% | 6.00E−29 | 41% | Holo-[acyl-carrier-protein] synthase |
| CSTER | 1705 | 100% | 0.00E+00 | 55% | Protein translocase subunit SecA |
| CSTER | 1726 | 100% | 5.00E−32 | 65% | |
| CSTER | 1727 | 93% | 1.00E−41 | 56% | Single-stranded DNA-binding protein B |
| CSTER | 1728 | 96% | 4.00E−40 | 61% | |
| CSTER | 1745 | 97% | 6.00E−130 | 55% | tRNA N6-adenosine threonylcarbamoyltransferase tsad |
| CSTER | 1747 | 100% | 6.00E−44 | 38% | tRNA threonylcarbamoyladenosine biosynthesis protein TsaB |
| CSTER | 1749 | 99% | 0.00E+00 | 62% | Ribonuclease J1 yqkc |
| CSTER | 1755 | 100% | 2.00E−124 | 50% | Phosphoglycerate kinase pgk |
| CSTER | 1762 | 100% | 0.00E+00 | 77% | |
| CSTER | 1763 | 100% | 1.00E−86 | 75% | |
| CSTER | 1764 | 98% | 3.00E−80 | 86% | |
| CSTER | 1770 | 99% | 5.00E−105 | 51% | Putative ribosome biogenesis GTPase RsgA |
| CSTER | 1776 | 92% | 1.00E−37 | 61% | Thioredoxin trxa |
| CSTER | 1787 | 100% | 1.00E−15 | 70% | |
| CSTER | 1790 | 95% | 1.00E−31 | 47% | Ribonuclease P protein component |
| CSTER | 1793 | 100% | 0.00E+00 | 55% | |
| CSTER | 1797 | 98% | 4.00E−99 | 65% | 50S ribosomal protein L1 |
| CSTER | 1809 | 94% | 4.00E−122 | 53% | Glycerol-3-phosphate dehydrogenase [NAD(P)+] gspA |
| CSTER | 1813 | 95% | 6.00E−120 | 47% | N-acetyldiaminopimelate deacetylase ykur |

TABLE 4-continued

Homologues to about 239 essential ORFs identified in *S. thermophilus*.

| | | | | | |
|---|---|---|---|---|---|
| CSTER | 1814 | 98% | 4.00E−86 | 60% | 2,3,4,5-tetrahydropyridine-2,6-dicarboxylate N-acetyltransferase dapH |
| CSTER | 1821 | 93% | 1.00E−25 | 40% | Single-stranded DNA-binding protein B |
| CSTER | 1844 | 97% | 0.00E+00 | 68% | DNA-directed RNA polymerase subunit beta |
| CSTER | 1845 | 98% | 0.00E+00 | 71% | DNA-directed RNA polymerase subunit beta' |
| CSTER | 1847 | 99% | 0.00E+00 | 58% | |
| CSTER | 1876 | 100% | 4.00E−83 | 45% | Probable fructose-bisphosphate aldolase fbaa |
| CSTER | 1880 | 100% | 2.00E−62 | 73% | |
| CSTER | 1881 | 99% | 7.00E−139 | 62% | DNA-directed RNA polymerase subunit alpha |
| CSTER | 1882 | 93% | 7.00E−69 | 87% | |
| CSTER | 1883 | 100% | 2.00E−58 | 73% | |
| CSTER | 1884 | 100% | 4.00E−16 | 84% | |
| CSTER | 1885 | 100% | 1.00E−38 | 78% | |
| CSTER | 1886 | 99% | 3.00E−89 | 59% | Adenylate kinase adk |
| CSTER | 1887 | 99% | 4.00E−140 | 49% | Protein translocase subunit SecY |
| CSTER | 1888 | 100% | 1.00E−70 | 72% | |
| CSTER | 1889 | 98% | 3.00E−20 | 62% | |
| CSTER | 1890 | 93% | 8.00E−70 | 76% | |
| CSTER | 1891 | 100% | 4.00E−55 | 73% | |
| CSTER | 1892 | 100% | 3.00E−69 | 60% | 50S ribosomal protein L6 |
| CSTER | 1893 | 100% | 1.00E−73 | 77% | |
| CSTER | 1894 | 100% | 1.00E−31 | 77% | |
| CSTER | 1895 | 99% | 3.00E−100 | 77% | |
| CSTER | 1896 | 99% | 7.00E−38 | 64% | |
| CSTER | 1897 | 100% | 5.00E−74 | 87% | |
| CSTER | 1898 | 97% | 4.00E−46 | 84% | |
| CSTER | 1899 | 78% | 1.00E−14 | 58% | |
| CSTER | 1900 | 93% | 1.00E−76 | 83% | |
| CSTER | 1901 | 100% | 1.00E−119 | 75% | |
| CSTER | 1902 | 96% | 7.00E−49 | 64% | |
| CSTER | 1903 | 100% | 2.00E−54 | 83% | |
| CSTER | 1904 | 100% | 5.00E−159 | 76% | 50S ribosomal protein L2 |
| CSTER | 1905 | 94% | 2.00E−31 | 60% | |
| CSTER | 1906 | 100% | 9.00E−92 | 60% | 50S ribosomal protein L4 |
| CSTER | 1907 | 99% | 4.00E−115 | 75% | 50S ribosomal protein L3 |
| CSTER | 1908 | 100% | 1.00E−58 | 78% | |
| CSTER | 1936 | 100% | 7.00E−26 | 69% | |
| CSTER | 1948 | 98% | 0.00E+00 | 57% | |
| CSTER | 1950 | 99% | 1.00E−140 | 49% | |
| CSTER | 1953 | 91% | 1.00E−10 | 48% | |
| CSTER | 1954 | 100% | 1.00E−14 | 55% | |
| CSTER | 1973 | 100% | 1.00E−95 | 69% | |
| CSTER | 1975 | 95% | 8.00E−176 | 56% | Replicative DNA helicase DnaC |
| CSTER | 1976 | 100% | 2.00E−39 | 55% | |
| CSTER | 1979 | 98% | 9.00E−177 | 70% | tRNA-specific 2-thiouridylase MnmA |
| CSTER | 1986 | 93% | 2.00E−45 | 52% | CDP-diacylglycerol--glycerol-3-phosphate 3-phosphatidyltransferase pgsA |
| CSTER | 1992 | 99% | 0.00E+00 | 68% | Inosine-5'-monophosphate dehydrogenase guab |
| CSTER | 1993 | 98% | 8.00E−42 | 35% | |

TABLE 5

List of differentially expressed genes identified in deletion strain GEI4.

| Operon | Putative pathway/ function | Regulator-effector | Gene | log$_2$ change | p-value |
|---|---|---|---|---|---|
| STER_0390-STER-0393 | Cysteine metabolism | Cmbr/Homr/Mtar | STER_0390 | −1.1 | 2.7E−23 |
| | | | STER_0391 | −1.3 | 2.2E−22 |
| | | | STER_0392 | −1.4 | 1.2E−32 |
| | | | STER_0393 | −1.2 | 2.8E−15 |
| STER_1016-STER_1017 | Maltodextrin metabolism | | STER_1016 | −1.0 | 0 |
| | | | STER_1017 | −0.8 | 7.50E−38 |
| STER_1548-STER_1555 | Aromatic amino acid biosynthesis | T-box RNA (Trp) | STER_1548 | −1.3 | 2.3E−37 |
| | | | STER_1549 | −1.0 | 1.5E−26 |
| | | | STER_1550 | −1.3 | 7.9E−38 |
| | | | STER_1551 | −1.3 | 1.2E−35 |
| | | | STER_1552 | −1.3 | 0 |
| | | | STER_1553 | −1.4 | 0 |
| | | | STER_1554 | −1.3 | 0 |
| | | | STER_1555 | −1.6 | 7.8E−73 |

TABLE 5-continued

List of differentially expressed genes identified in deletion strain GEI4.

| Operon | Putative pathway/ function | Regulator-effector | Gene | log$_2$ change | p-value |
|---|---|---|---|---|---|
| STER_1960-<br>STER_1963 | Membrane proteins | | STER_1960 | −0.9 | 0 |
| | | | STER_1961 | −1.0 | 0 |
| | | | STER_1962 | −1.0 | 8.3E−317 |
| | | | STER_1963 | −1.1 | 3.2E−965 |
| STER_0049-<br>STER_0054 | Purine biosynthesis | PurR | STER_0049 | 1.2 | 5.5E−34 |
| | | | STER_0050 | 1.1 | 1.4E−29 |
| | | | STER_0051 | 1.1 | 0 |
| | | | STER_0052 | 1.1 | 0 |
| | | | STER_0053 | 1.1 | 0 |
| | | | STER_0054 | 1.1 | 6.6E−40 |
| STER_0699-<br>STER_0701 | Ethanolamine metabolism | | STER_0699 | 1.6 | 0 |
| | | | STER_0700 | 2.1 | 9.5E−200 |
| | | | STER_0701 | 2.2 | 7.8E−329 |
| STER_1020-<br>STER_1024 | Twin arginine translocase | TatA | STER_1020 | 1.3 | 5.3E−14 |
| | | | STER_1021 | 1.3 | 8.8E−12 |
| | | | STER_1022 | 1.4 | 3.3E−12 |
| | | | STER_1023 | 1.0 | 9.6E−6 |
| | | | STER_1024 | 0.9 | 0.0022 |
| STER_1025-<br>STER_1028 | Iron homeostasis | PerR | STER_1025 | 1.1 | 1.9E−09 |
| | | | STER_1026 | 0.9 | 2.5E−6 |
| | | | STER_1027 | 1.2 | 3E−12 |
| | | | STER_1028 | 1.2 | 1.5E−17 |
| STER_1405-<br>STER_1409 | ABC Peptide Transport | Cody | STER_1405 | 1.6 | 9.5E−90 |
| | | | STER_1406 | 1.6 | 0 |
| | | | STER_1407 | 1.6 | 3.7E−59 |
| | | | STER_1408 | 1.5 | 0 |
| | | | STER_1409 | 1.4 | 4.2E−54 |
| STER_1821-<br>STER_1823 | Stress | | STER_1821 | 2.0 | 0 |
| | | | STER_1822 | 2.2 | 5.4E−98 |
| | | | STER_1823 | 2.0 | 0 |

REFERENCES

1. Darmon E, Leach D F. (2014) Bacterial Genome Instability. *Microbiol. Mol. Biol. Rev.* 78, 1-39.
2. Labrie S J, Samson J E, and Moineau S. (2010) Bacteriophage resistance mechanisms. *Nat. Rev. Microbiol.* 8, 317-327.
3. Barrangou R, Marraffini L A (2014) CRISPR-Cas systems: prokaryotes upgrade to adaptive immunity. *Mol Cell* 54(2):234-244.
4. Barrangou R, et al. (2007) CRISPR provides acquired resistance against viruses in prokaryotes. *Science* 315 (5819):1709-1712.
5. Brouns S J J, et al. (2008) Small CRISPR RNAs guide antiviral defense in prokaryotes. *Science* 321(5891):960-964.
6. Young J C et al. (2012) Phage-induced expression of CRISPR-associated proteins is revealed by shotgun proteomics in *Streptococcus thermophilus*. *PLoS ONE* 7(5): e38077.
7. Garneau J E, et al. (2010) The CRISPR/Cas bacterial immune system cleaves bacteriophage and plasmid DNA. *Nature* 468(7320):67-71.
8. Groenen P M, Bunschoten A E, Van Soolingen D, Van Embden J D (1993) Nature of DNA polymorphism in the direct repeat cluster of *Mycobacterium tuberculosis*; application for strain differentiation by a novel typing method. *Mol Microbiol* 10(5):1057-1065.
9. Yin S, et al. (2013) The evolutionary divergence of Shiga toxin-producing *Escherichia coli* is reflected in clustered regularly interspaced short palindromic repeat (CRISPR) spacer composition. *Appl Environ Microbiol* 79(18): 5710-5720.
10. Liu F, et al. (2011) Novel virulence gene and clustered regularly interspaced short palindromic repeat (CRISPR) multilocus sequence typing scheme for subtyping of the major serovars of *Salmonella enterica* subsp. *enterica*. *Appl Environ Microbiol* 77(6):1946-1956.
11. Barrangou R, Horvath P (2012) CRISPR: new horizons in phage resistance and strain identification. *Annu Rev Food Sci Technol* 3, 143-162.
12. Sander J D, and Joung J K. (2014) CRISPR-Cas systems for editing, regulating and targeting genomes. *Nat. Biotechnol.* 32, 347-355.
13. Bikard D, et al. (2013) Programmable repression and activation of bacterial gene expression using an engineered CRISPR-Cas system. *Nucleic Acids Res* 41(15): 7429-7437
14. Qi L S, et al. (2013) Repurposing CRISPR as an RNA-Guided Platform for Sequence-Specific Control of Gene Expression. *Cell* 152(5):1173-1183.
15. Gomaa A A, et al. (2014) Programmable Removal of Bacterial Strains by Use of Genome-Targeting CRISPR-Cas Systems. *mBio* 5(1):e00928-13.
16. Ishino Y, Shinagawa H, Makino K, Amemura M, Nakata A (1987) Nucleotide sequence of the iap gene, responsible for alkaline phosphatase isozyme conversion in *Escherichia coli*, and identification of the gene product. *J Bacteriol* 169(12):5429-5433.
17. Jansen R, Embden J D A van, Gaastra W, Schouls L M (2002) Identification of genes that are associated with DNA repeats in prokaryotes. *Mol Microbiol* 43(6):1565-1575.
18. Bolotin A, et al. (2004) Complete sequence and comparative genome analysis of the dairy bacterium *Streptococcus thermophilus*. *Nat Biotechnol* 22(12):1554-1558.
19. Horvath P, et al. (2008) Diversity, activity, and evolution of CRISPR loci in *Streptococcus thermophilus*. *J Bacteriol* 190(4):1401-1412.
20. Bolotin A, Quinguis B, Sorokin A, Ehrlich S D (2005) Clustered regularly interspaced short palindrome repeats (CRISPRs) have spacers of extrachromosomal origin. *Microbiology* 151(Pt 8):2551-2561.
21. Deveau H, et al. (2008) Phage response to CRISPR-encoded resistance in *Streptococcus thermophilus*. *J Bacteriol* 190(4): 1390-1400.
22. Paez-Espino D, et al. (2013) Strong bias in the bacterial CRISPR elements that confer immunity to phage. *Nat Commun* 4, 1430.
23. Sun C L, et al. (2013) Phage mutations in response to CRISPR diversification in a bacterial population. *Environ Microbiol* 15(2):463-470.
24. Sapranauskas R, et al. (2011) The *Streptococcus thermophilus* CRISPR/Cas system provides immunity in *Escherichia coli*. *Nucleic Acids Res* 39(21):9275-9282.
25. Gasiunas G, Barrangou R, Horvath P, Siksnys V (2012) Cas9-crRNA ribonucleoprotein complex mediates specific DNA cleavage for adaptive immunity in bacteria. *Proc Natl Acad Sci USA* 109(39):E2579-2586.
26. Briner A E, et al. (2014) Guide RNA Functional Modules Direct Cas9 Activity and Orthogonality. *Molecular Cell.* 56(2):333-339
27. Bondy-Denomy J, Davidson A R. (2014) To acquire or resist: the complex biological effects of CRISPR-Cas systems. *Trends Microbiol.* 22, 218-225.
28. Horvath P, et al. (2009) Comparative analysis of CRISPR loci in lactic acid bacteria genomes. *Int J Food Microbiol* 131(1): 62-70.

29. Jiang W, Bikard D, Cox D, Zhang F, Marraffini L A. (2013a) RNA-guided editing of bacterial genomes using CRISPR-Cas systems. *Nat Biotechnol* 31(3):233-239.
30. Vercoe R B, et al. (2013) Cytotoxic chromosomal targeting by CRISPR/Cas systems can reshape bacterial genomes and expel or remodel pathogenicity islands. *PLoS Genet* 9(4):e1003454.
31. Oh J H, van Pijkeren J P. (2014) CRISPR-Cas9-assisted recombineering in *Lactobacillus reuteri*. *Nucleic Acids Res* 10.1093/nar/gku623
32. Selle K, Barrangou R. (2015) Harnessing CRISPR-Cas systems for bacterial genome editing. *Trends Microbiol.* In press
33. Kobayashi K, et al. (2003) Essential *Bacillus subtilis* genes. *Proc. Natl. Acad. Sci. U.S.A.* 100, 4678-4683.
34. Mahillon J, Chandler M. (1998) Insertion sequences. *Microbiol Mol Biol Rev* 62(3):725-774.
35. Goh Y J, Goin C, O'Flaherty S, Altermann E, Hutkins R (2011) Specialized adaptation of a lactic acid bacterium to the milk environment; the comparative genomics of *Streptococcus thermophilus* LMD-9. *Microbial Cell Factories* 10 (Suppl 1):S22
36. Dandoy D, et al. (2011) The fast milk acidifying phenotype of *Streptococcus thermophilus* can be acquired by natural transformation of the genomic island encoding the cell-envelope proteinase PrtS. *Microb. Cell Fact.* 10 Suppl 1, S21.
37. Deltcheva E, et al. (2011) CRISPR RNA maturation by trans-activating small RNA and host factor RNase III. *Nature* 471, 602-607.
38. Aravind L, Koonin E V (2001) Prokaryotic homologs of the eukaryotic DNA-end-binding protein Ku, novel domains in the Ku protein and prediction of a prokaryotic double-strand break repair system. *Genome Res* 11(8): 1365-1374.
39. Koonin E V, Makarova K S (2007) Evolutionary genomics of lactic acid bacteria. *J Bacteriol* 189(4): 1199-1208
40. Makarova K S, et al. (2006) Comparative genomics of the lactic acid bacteria. *Proc Natl Acad Sci USA* 103(42): 15611-15616.
41. Goh Y J, et al. (2009) Development and application of a upp-based counterselective gene replacement system for the study of the S-layer protein SlpX of *Lactobacillus acidophilus* NCFM. *Appl Environ Microbiol* 75(10): 3093-3105.
42. Horton R M, Hunt H D, Ho S N, Pullen J K, Pease L R (1989) Engineering hybrid genes without the use of restriction enzymes: gene splicing by overlap extension. *Gene* 77(1):61-68.
43. Mojica F J M, C, Garcia-Martinez J, Almendros C (2009) Short motif sequences determine the targets of the prokaryotic CRISPR defence system. *Microbiology* 155 (Pt 3):733-740.
44. Russell W M, Klaenhammer T R (2001) Efficient System for Directed Integration into the *Lactobacillus acidophilus* and *Lactobacillus gasseri* Chromosomes via Homologous Recombination. *Appl Environ Microbiol* 67(9): 4361-4364.
45. Wei M-Q, et al. (1995) An improved method for the transformation of *Lactobacillus* strains using electroporation. *Journal of Microbiological Methods* 21(1):97-109.
46. Zhang X, Bremer H (1995) Control of the *Escherichia coli* rrnB p1 promoter strength by ppGpp. *Journal of Biological Chemistry* 270(19):11181-11189.
47. Law J, et al. (1995) A system to generate chromosomal mutations in *Lactococcus lactis* which allows fast analysis of targeted genes. *J Bacteriol* 177(24):7011-7018.

The foregoing is illustrative of the present invention, and is not to be construed as limiting thereof. The invention is defined by the following claims, with equivalents of the claims to be included therein.

---

That which is claimed is:

1. A method of selectively killing a specific bacterial subset within a mixed population of bacterial cells on the basis of the distinct genetic content in the bacterial subset, the method comprising:
    introducing into the mixed population of bacterial cells a heterologous nucleic acid construct comprising:
    (a) a CRISPR-Cas system, wherein the CRISPR-Cas system is a Type I CRISPR Cas system or a Type V CRISPR Cas system,
    wherein the Type I CRISPR-Cas system comprises (i) a heterologous nucleic acid construct encoding at least one Type I Cascade polypeptide, (ii) a Cas3, or a Cas3' and Cas3" polypeptide or a heterologous nucleic acid construct encoding a Cas3, or a Cas3' and Cas3" polypeptide, and (iii) a Type I CRISPR array comprising (5' to 3') a repeat-spacer-repeat sequence or at least one repeat-spacer sequence, wherein the spacer of the repeat-spacer-repeat sequence or the repeat-spacer sequence comprises a nucleotide sequence that is substantially complementary to a target region in a conserved genetic sequence of the specific bacterial subset that is distinct from other bacterial cells in the mixed population, the target region having at least 10 consecutive nucleotides adjacent to a protospacer-adjacent motif (PAM) recognized by the CRISPR-Cas system, and
    wherein the heterologous nucleic acid construct of (i) and the heterologous construct of (ii) of the Type I CRISPR Cas system do not integrate into the genome of the bacterial cells of the mixed population,
    wherein the Type V CRISPR-Cas system comprises (i) a heterologous nucleic acid construct encoding at least one Cpf1 polypeptide, (ii) a Cas1, or a Cas2, or a Cas4 polypeptide, and (iii) a Type V CRISPR array comprising (5' to 3') a repeat-spacer-repeat sequence or at least one repeat-spacer sequence, wherein the spacer of the repeat-spacer-repeat sequence or the repeat-spacer sequence comprises a nucleotide sequence that is substantially complementary to a target region in a conserved genetic sequence of the specific bacterial subset that is distinct from other bacterial cells in the mixed population, the target region having at least 10 consecutive nucleotides adjacent to a protospacer-adjacent motif (PAM) recognized by the CRISPR-Cas system, and wherein the heterologous nucleic acid construct of (i) and the heterologous construct of (ii) of the Type V CRISPR Cas system do not integrate into the genome of the bacterial cells of the mixed population, thereby selectively killing the specific bacterial subset that comprises the target region.

2. The method of claim 1, wherein at least one or more bacterial cells in the mixed population does not comprise the target region and, therefore, the at least one bacterial cell is not killed upon introduction of the CRISPR-Cas system.

3. The method of claim 1, wherein the spacer of the repeat-spacer-repeat sequence or the at least one repeat-spacer sequence comprises a nucleotide sequence that is 100% complementary to the target region.

4. The method of claim 1, wherein the repeat-spacer-repeat sequence or the at least one repeat-spacer sequence of the Type I CRISPR array comprises a repeat that is identical to a repeat from a wild-type Type I CRISPR array and the repeat-spacer-repeat sequence or the at least one repeat-spacer sequence of the Type V CRISPR array comprises a repeat that is identical to a repeat from a wild type Type V CRISPR array.

5. The method of claim 1, wherein the target region is within an essential gene.

6. The method of claim 1, wherein the target region is within a non-essential gene.

7. The method of claim 1, wherein the target region is selected from a gene, open reading frame or a putative open reading frame or an intergenic region.

8. A method of selecting from a population of bacterial cells at least one isolate that does not comprise in its genome a conserved target region that is present in the genome of one or more bacterial cells in the population, comprising:
  introducing into the population of bacterial cells a heterologous nucleic acid construct comprising:
   (a) a CRISPR-Cas system wherein the CRISPR-Cas system is a Type I or a Type V CRISPR Cas system,
   wherein the Type I CRISPR-Cas system comprises (i) a heterologous nucleic acid construct encoding at least one Type I Cascade polypeptide, (ii) a Cas3, or a Cas3' and Cas3" polypeptide or a heterologous nucleic acid construct encoding a Cas3, or a Cas3' and Cas3" polypeptide, and (iii) a Type I CRISPR array comprising (5' to 3') a repeat-spacer-repeat sequence or at least one repeat-spacer sequence, wherein the spacer of the repeat-spacer-repeat sequence or the repeat-spacer sequence comprises a nucleotide sequence that is substantially complementary to the conserved target region that is present in the genome of the one or more bacterial cells of the population, wherein the heterologous nucleic acid construct of (i) and the heterologous construct of (ii) of the Type I CRISPR Cas system do not integrate into the genome of the bacterial cells of the population, wherein the Type V CRISPR-Cas system comprises (i) a heterologous nucleic acid construct encoding at least one Cpf1 polypeptide, (ii) a Cas1, or a Cas2, or a Cas4 polypeptide, and (iii) a Type V CRISPR array comprising (5' to 3') a repeat-spacer-repeat sequence or at least one repeat-spacer sequence, wherein the spacer of the repeat-spacer-repeat sequence or the at least one repeat-spacer sequence comprises a nucleotide sequence that is substantially complementary to the conserved target region that is present in the genome of the one or more bacterial cells of the population, wherein cells comprising the conserved target region are killed, wherein the heterologous nucleic acid construct of (i) and the heterologous construct of (ii) of the Type V CRISPR Cas system do not integrate into the genome of the bacterial cells of the population, and selecting from the population of bacterial cells at least one isolate without the conserved target region in its genome.

9. The method of claim 8, further comprising growing individual bacterial colonies of the at least one isolate without the conserved target region in its genome.

10. The method of claim 8, wherein the repeat-spacer-repeat sequence or the at least one repeat-spacer sequence of the Type I CRISPR array comprises a repeat that is identical to a repeat from a wild-type Type I CRISPR array and the repeat-spacer-repeat sequence or the at least one repeat-spacer sequence of the Type V CRISPR array comprises a repeat that is identical to a repeat from a wild type Type V CRISPR array.

11. The method of claim 8, wherein the CRISPR array is a Type I CRISPR array and the repeat-spacer-repeat sequence or the at least one repeat-spacer sequence comprises a repeat that is identical to a repeat from a wild-type Type I CRISPR array and the CRISPR-Cas system comprises (i) a heterologous nucleic acid construct encoding at least one Type I Cascade polypeptide, and (ii) a Cas3, or a Cas3' and Cas3" polypeptide or a heterologous nucleic acid construct encoding a Cas3, or a Cas3' and Cas3" polypeptide.

12. The method of claim 8, wherein the CRISPR array is a Type V CRISPR array and the repeat-spacer-repeat sequence or the at least one repeat-spacer sequence comprises a repeat that is identical to a repeat from a wildtype Type V CRISPR array and the CRISPR-Cas system comprises: (i) a heterologous nucleic acid construct encoding at least one Cpf1 polypeptide, and (ii) a Cas1, or a Cas2, or a Cas4 polypeptide.

* * * * *

UNITED STATES PATENT AND TRADEMARK OFFICE
CERTIFICATE OF CORRECTION

PATENT NO. : 11,261,451 B2
APPLICATION NO. : 16/153052
DATED : March 1, 2022
INVENTOR(S) : Barrangou et al.

Page 1 of 1

It is certified that error appears in the above-identified patent and that said Letters Patent is hereby corrected as shown below:

On the Title Page

(56) References Cited, OTHER PUBLICATIONS, Page 3, Column 1, Line 64, Briner cite: Please correct "Bartangou R. "LactoPaclRjs. buchneri" to read -- Barrangou R. "Lactobacillus buchneri --

(56) References Cited, OTHER PUBLICATIONS, Page 3, Column 2, Line 27: Please correct "PCT/IB2015/052615" to read -- PCT/IB2015/052515 --

(56) References Cited, OTHER PUBLICATIONS, Page 3, Column 2, Line 63, Ajdic cite: Please correct "https://www.nobl.nlm.nlh.gov/protein/NP_721764.1/" to read
-- https://www.ncbi.nlm.nih.gov/protein/NP_721764.1/ --

In the Specification

Column 9, Line 65: Please correct "$\log_e$" to read -- $\log_2$ --

Column 32, Line 53: Please correct "$Lac^k$" to read -- $Lac^+$ --

Column 32, Line 55: Please correct "$Lac^k$" to read -- $Lac^+$ --

Column 40, Line 44: Please correct "a111473" to read -- all1473 --

Signed and Sealed this
Thirty-first Day of May, 2022

Katherine Kelly Vidal
*Director of the United States Patent and Trademark Office*

SEQUENCE LISTING

<160> NUMBER OF SEQ ID NOS: 66

<210> SEQ ID NO 1
<211> LENGTH: 102
<212> TYPE: DNA
<213> ORGANISM: Artificial
<220> FEATURE:
<223> OTHER INFORMATION: Exemplary S. thermophilus CRISPR1 target
      sequence

<400> SEQUENCE: 1
gtttttgtac tctcaagatt taagtaactg tacaacaatc cccatagcac gaacaatata      60
gttgttgttt ttgtactctc aagatttaag taactgtaca ac                        102

<210> SEQ ID NO 2
<211> LENGTH: 103
<212> TYPE: DNA
<213> ORGANISM: Artificial
<220> FEATURE:
<223> OTHER INFORMATION: Exemplary S. thermophilus CRISPR3 target
      sequence

<400> SEQUENCE: 2
gttttagagc tgtgttgttt cgaatggttc caaaacagta ttttgaatct cttgaagaat      60
tttctgagtt ttagagctgt gttgtttcga atggttccaa aac                       103

```
<210> SEQ ID NO 3
<211> LENGTH: 102
<212> TYPE: DNA
<213> ORGANISM: Artificial
<220> FEATURE:
<223> OTHER INFORMATION: Exemplary S. thermophilus CRISPR3 target
      sequence

<400> SEQUENCE: 3
gttttagagc tgtgttgttt cgaatggttc caaaacgata acacgagata aaacatccag      60
cccaccgttt tagagctgtg ttgtttcgaa tggttccaaa ac                        102

<210> SEQ ID NO 4
<211> LENGTH: 102
<212> TYPE: DNA
<213> ORGANISM: Artificial
<220> FEATURE:
<223> OTHER INFORMATION: Exemplary S. thermophilus CRISPR3 target
      sequence

<400> SEQUENCE: 4
gttttagagc tgtgttgttt cgaatggttc caaaacgttg tagctttgag gtctgagaat      60
acacgcgttt tagagctgtg ttgtttcgaa tggttccaaa ac                        102

<210> SEQ ID NO 5
<211> LENGTH: 102
<212> TYPE: DNA
<213> ORGANISM: Artificial
<220> FEATURE:
<223> OTHER INFORMATION: Exemplary S. thermophilus CRISPR3 target
      sequence

<400> SEQUENCE: 5
gttttagagc tgtgttgttt cgaatggttc caaaacgatt gctcaatcaa tcgtttcagc      60
tgctaagttt tagagctgtg ttgtttcgaa tggttccaaa ac                        102

<210> SEQ ID NO 6
<211> LENGTH: 35
<212> TYPE: DNA
<213> ORGANISM: Artificial
<220> FEATURE:
<223> OTHER INFORMATION: Exemplary S. thermophilus CRISPR3 spacer
      sequence

<400> SEQUENCE: 6
ggtgggctgg atgttttatc tcgtgttatc tgggg                                 35

<210> SEQ ID NO 7
<211> LENGTH: 35
<212> TYPE: DNA
<213> ORGANISM: Artificial
<220> FEATURE:
<223> OTHER INFORMATION: Exemplary S. thermophilus CRISPR3 spacer
      sequence

<400> SEQUENCE: 7
gcgtgtattc tcagacctca aagctacaac aggcg                                 35

<210> SEQ ID NO 8
<211> LENGTH: 35
<212> TYPE: DNA
<213> ORGANISM: Artificial
<220> FEATURE:
<223> OTHER INFORMATION: Exemplary S. thermophilus CRISPR3 spacer
      sequence
```

```
<400> SEQUENCE: 8
ttagcagctg aaacgattga ttgagcaatc gggtg                              35

<210> SEQ ID NO 9
<211> LENGTH: 36
<212> TYPE: DNA
<213> ORGANISM: Artificial
<220> FEATURE:
<223> OTHER INFORMATION: Exemplary S. thermophilus CRISPR3 spacer
      sequence

<400> SEQUENCE: 9
ctccagaagt cttggtcttc caaccagctt gctgta                             36

<210> SEQ ID NO 10
<211> LENGTH: 36
<212> TYPE: DNA
<213> ORGANISM: Artificial
<220> FEATURE:
<223> OTHER INFORMATION: Exemplary S. thermophilus CRISPR3 spacer
      sequence

<400> SEQUENCE: 10
ccccttcaga aaattcttca agagattcaa aatact                             36

<210> SEQ ID NO 11
<211> LENGTH: 38
<212> TYPE: DNA
<213> ORGANISM: Artificial
<220> FEATURE:
<223> OTHER INFORMATION: Exemplary S. thermophilus CRISPR1 spacer
      sequence

<400> SEQUENCE: 11
attaagagat tgtcttaact tcatctcccc ttcagaaa                           38

<210> SEQ ID NO 12
<211> LENGTH: 40
<212> TYPE: RNA
<213> ORGANISM: Streptococcus thermophilus

<400> SEQUENCE: 12
gucuuaacuu caucccccu guuuuuguac ucucaagauu                          40

<210> SEQ ID NO 13
<211> LENGTH: 73
<212> TYPE: RNA
<213> ORGANISM: Streptococcus thermophilus

<400> SEQUENCE: 13
aaucuugcag aagcuacaaa gauaaggcuu caugccgaaa ucaacacccu gucauuuuau   60
ggcagggugu uuu                                                      73

<210> SEQ ID NO 14
<211> LENGTH: 51
<212> TYPE: DNA
<213> ORGANISM: Artificial
<220> FEATURE:
<223> OTHER INFORMATION: Exemplary S. thermophilus CRISPR/Cas Type II
      target sequence

<400> SEQUENCE: 14
attaagagat tgtcttaact tcatctcccc ttcagaaaat tcttcaagag a            51
```

```
<210> SEQ ID NO 15
<211> LENGTH: 51
<212> TYPE: DNA
<213> ORGANISM: Artificial
<220> FEATURE:
<223> OTHER INFORMATION: Complement to exemplary S. thermophilus
      CRISPR/Cas Type II target squence

<400> SEQUENCE: 15
tctcttgaag aattttctga aggggagatg aagttaagac aatctcttaa t          51

<210> SEQ ID NO 16
<211> LENGTH: 38
<212> TYPE: RNA
<213> ORGANISM: Streptococcus thermophilus

<400> SEQUENCE: 16
ucucuugaag aauuuucuga guuuuagagc uguguugu                          38

<210> SEQ ID NO 17
<211> LENGTH: 71
<212> TYPE: RNA
<213> ORGANISM: Streptococcus thermophilus

<400> SEQUENCE: 17
acaacacagc gaguuaaaau aaggcuuagu ccguacucaa cuugaaaagg uggcaccgau  60
ucgguguuuu u                                                       71

<210> SEQ ID NO 18
<211> LENGTH: 51
<212> TYPE: DNA
<213> ORGANISM: Artificial
<220> FEATURE:
<223> OTHER INFORMATION: Exemplary S. thermophilus CRISPR/Cas Type II
      target sequence

<400> SEQUENCE: 18
agtattttga atctcttgaa gaattttctg aaggggagat gaagttaaga c           51

<210> SEQ ID NO 19
<211> LENGTH: 51
<212> TYPE: DNA
<213> ORGANISM: Artificial
<220> FEATURE:
<223> OTHER INFORMATION: Complement to exemplary S. thermophilus
      CRISPR/Cas Type II target sequence

<400> SEQUENCE: 19
gtcttaactt catctcccct tcagaaaatt cttcaagaga ttcaaaatac t           51

<210> SEQ ID NO 20
<211> LENGTH: 25
<212> TYPE: DNA
<213> ORGANISM: Artificial
<220> FEATURE:
<223> OTHER INFORMATION: Exemplary upstream IS1193 element sequence

<400> SEQUENCE: 20
tggagcttat attccactgg ctcgc                                        25

<210> SEQ ID NO 21
<211> LENGTH: 25
<212> TYPE: DNA
<213> ORGANISM: Artificial
<220> FEATURE:
<223> OTHER INFORMATION: Exemplary downstream IS1193 element sequence
```

```
<400> SEQUENCE: 21
aggatcttat atgctactag ttcgt                                          25

<210> SEQ ID NO 22
<211> LENGTH: 25
<212> TYPE: DNA
<213> ORGANISM: Artificial
<220> FEATURE:
<223> OTHER INFORMATION: Exemplary chimeric IS1193 deletion footprint
      sequence

<400> SEQUENCE: 22
tggagcttat atgctactag ttcgt                                          25

<210> SEQ ID NO 23
<211> LENGTH: 53
<212> TYPE: RNA
<213> ORGANISM: Lactobacillus casei

<400> SEQUENCE: 23
cauugcuuua aaauggcaa gucucaggua gaugucgaau caaucaguuc aag            53

<210> SEQ ID NO 24
<211> LENGTH: 122
<212> TYPE: RNA
<213> ORGANISM: Artificial
<220> FEATURE:
<223> OTHER INFORMATION: Exemplary L. casei CRISPR-Cas Type II tracrRNA
      sequence

<400> SEQUENCE: 24
uuugaacuga uugauucgac aucuacacgu ugagaucaaa caagcuucgg cugaguuuca    60
auuuuugagc ccauguuggg ccauacauac cgccauccgg gaagauaccg gguggcauuu   120
uu                                                                 122

<210> SEQ ID NO 25
<211> LENGTH: 73
<212> TYPE: DNA
<213> ORGANISM: Lactobacillus vini

<400> SEQUENCE: 25
ctttagttgt tgtgtgtaag tgcgcattgc tttaaaaatg gcaatgaaaa aatccaaaga    60
aaatgtcaaa ggc                                                      73

<210> SEQ ID NO 26
<211> LENGTH: 73
<212> TYPE: DNA
<213> ORGANISM: Lactobacillus vini

<400> SEQUENCE: 26
gcctttgaca tttctttgg attttttcat tgccattttt aaagcaatgc gcacttacac     60
acaacaacta aag                                                      73

<210> SEQ ID NO 27
<211> LENGTH: 88
<212> TYPE: RNA
<213> ORGANISM: Lactobacillus casei

<400> SEQUENCE: 27
uuugaacuga uugauucgac aucuacacgu ugagaucaaa caagcuucgg cugaguuuca    60
auuuuugagc ccauguuggg ccauacau                                      88
```

```
<210> SEQ ID NO 28
<211> LENGTH: 117
<212> TYPE: RNA
<213> ORGANISM: Artificial
<220> FEATURE:
<223> OTHER INFORMATION: Exemplary L. casei CRISPR-Cas Type II single
      guide sequence

<400> SEQUENCE: 28
cauugcuuua aaauggcaa gucucaggua gaugucgaaa caauucgaca ucuacacguu      60
gagaucaaac aagcuucggc ugaguucaa uuuugagcc cauguggc cauacau           117

<210> SEQ ID NO 29
<211> LENGTH: 53
<212> TYPE: RNA
<213> ORGANISM: Lactobacillus gasseri

<400> SEQUENCE: 29 gauugauua acgguauac guuuagaug guuguuagau caauaaggcu uag               53

<210> SEQ ID NO 30
<211> LENGTH: 109
<212> TYPE: RNA
<213> ORGANISM: Artificial
<220> FEATURE:
<223> OTHER INFORMATION: Exemplary L. gasseri CRISPR-Cas Type II
      tracrRNA sequence

<400> SEQUENCE: 30
cuaaacuuua uugaucuaac aaccagauuu aaaaucaagc aaugcaucuu uugaugcaaa     60 guucaauac uugucccgag cuacgaggg acuuuuuua ugcaaaaaa                    109

<210> SEQ ID NO 31
<211> LENGTH: 30
<212> TYPE: DNA
<213> ORGANISM: Artificial
<220> FEATURE:
<223> OTHER INFORMATION: Exemplary L. gasseri protospacer sequence

<400> SEQUENCE: 31
gtataccagt taatcaaatc tccacggtat                                      30

<210> SEQ ID NO 32
<211> LENGTH: 98
<212> TYPE: RNA
<213> ORGANISM: Lactobacillus gasseri

<400> SEQUENCE: 32
cuaaacuuua uugaucuaac aaccagauuu aaaaucaagc aaugcaucuu uugaugcaaa     60 guucaauac uugucccgag cuacgaggg acuuuuuu                               98

<210> SEQ ID NO 33
<211> LENGTH: 72
<212> TYPE: DNA
<213> ORGANISM: Artificial
<220> FEATURE:
<223> OTHER INFORMATION: Exemplary L. gasseri CRISPR-Cas Type II target
      sequence

<400> SEQUENCE: 33
ctgattacca acaataccgt ggagatttga ttaactggta tacttaacaa caagacagta     60
actcaagctg ca                                                         72
```

```
<210> SEQ ID NO 34
<211> LENGTH: 72
<212> TYPE: DNA
<213> ORGANISM: Artificial
<220> FEATURE:
<223> OTHER INFORMATION: Complement to exemplary L. gasseri CRISPR-Cas
      Type II target sequence

<400> SEQUENCE: 34
tgcagcttga gttactgtct tgttgttaag tataccagtt aatcaaatct ccacggtatt    60
gttggtaatc ag                                                        72

<210> SEQ ID NO 35
<211> LENGTH: 129
<212> TYPE: RNA
<213> ORGANISM: Artificial
<220> FEATURE:
<223> OTHER INFORMATION: Exemplary L. gasseri CRISPR/Cas Type II single
      guide sequence

<400> SEQUENCE: 35
gauuugauua acugguauac guuuuagaug guuguuagau cgaaaucuaa caaccagauu    60
uaaaaucaag caaugcaucu uuugaugcaa aguuucaaua cuugucccga gcuaucgagg   120
gacuuuuuu                                                           129

<210> SEQ ID NO 36
<211> LENGTH: 65
<212> TYPE: DNA
<213> ORGANISM: Artificial
<220> FEATURE:
<223> OTHER INFORMATION: Exemplary L. gasseri CRISPR-Cas Type II target
      sequence

<400> SEQUENCE: 36
ccaacaatac cgtggagatt tgattaactg gtatacttaa caacaagaca gtaactcaag    60
ctgca                                                                65

<210> SEQ ID NO 37
<211> LENGTH: 65
<212> TYPE: DNA
<213> ORGANISM: Artificial
<220> FEATURE:
<223> OTHER INFORMATION: Complement to exemplary L. gasseri CRISPR-Cas
      Type II target sequence

<400> SEQUENCE: 37
tgcagcttga gttactgtct tgttgttaag tataccagtt aatcaaatct ccacggtatt    60
gttgg                                                                65

<210> SEQ ID NO 38
<211> LENGTH: 56
<212> TYPE: RNA
<213> ORGANISM: Lactobacillus pentosus

<400> SEQUENCE: 38
cauugcuuua aaauggcaa gucuugaaua guagucauau caaacagguu uagaac         56

<210> SEQ ID NO 39
<211> LENGTH: 117
<212> TYPE: RNA
<213> ORGANISM: Artificial
<220> FEATURE:
<223> OTHER INFORMATION: Exemplary L. pentosus CRISPR-Cas Type II
      tracrRNA sequence
```

<400> SEQUENCE: 39
guucuaaacc uucuugauau gacuacuagc gucaagauca aacaaggcau uuugccgagu    60
uucaccuuuu gaguccguau ucggaccauu acauauguau caagaugucg cccauuu      117

<210> SEQ ID NO 40
<211> LENGTH: 90
<212> TYPE: DNA
<213> ORGANISM: Lactobacillus pentosus

<400> SEQUENCE: 40
guucuaaacc uucuugauau gacuacuagc gucaagauca aacaaggcau uuugccgagu    60
uucaccuuuu gaguccguau ucggaccauu                                     90

<210> SEQ ID NO 41
<211> LENGTH: 47
<212> TYPE: DNA
<213> ORGANISM: Artificial
<220> FEATURE:
<223> OTHER INFORMATION: Exemplary L. pentosus CRISPR/Cas Type II target
      sequence
<220> FEATURE:
<221> NAME/KEY: misc_feature
<222> LOCATION: (45)..(46)
<223> OTHER INFORMATION: n is a, c, g, t or u

<400> SEQUENCE: 41
ctttagttgt tctgtgtaag tgcgcattgc tttaaaaatg gcaanng                 47

<210> SEQ ID NO 42
<211> LENGTH: 47
<212> TYPE: DNA
<213> ORGANISM: Artificial
<220> FEATURE:
<223> OTHER INFORMATION: Complement of exemplary L. pentosus CRISPR/Cas
      Type II target sequence
<220> FEATURE:
<221> NAME/KEY: misc_feature
<222> LOCATION: (2)..(3)
<223> OTHER INFORMATION: n is a, c, g, t or u

<400> SEQUENCE: 42
cnnttgccat ttttaaagca atgcgcactt acacagaaca actaaag                 47

<210> SEQ ID NO 43
<211> LENGTH: 118
<212> TYPE: RNA
<213> ORGANISM: Artificial
<220> FEATURE:
<223> OTHER INFORMATION: Exemplary L. pentosus CRISPR/Cas Type II single
      guide sequence

<400> SEQUENCE: 43
cauugcuuua aaauggcaa gucuugaaua guagucauau cgaaaugau cuacuagcgu      60 caagaucaaa caaggcauuu ugccgaguuu caccuuuga guccguauuc ggaccauu      118

<210> SEQ ID NO 44
<211> LENGTH: 54
<212> TYPE: RNA
<213> ORGANISM: Lactobacillus jensenii

<400> SEQUENCE: 44 gauugauua acugguauac guuuuagaag guuguuaaau caguaaguug aaaa           54

```
<210> SEQ ID NO 45
<211> LENGTH: 95
<212> TYPE: RNA
<213> ORGANISM: Lactobacillus jensenii

<400> SEQUENCE: 45
auuucaauuu acugauuuaa caaccuuauu uuuaaaauca acaaggucu uaguaccgag      60 uuuucacaug uguaccgcuu auagcggucu uuuuu                               95

<210> SEQ ID NO 46
<211> LENGTH: 71
<212> TYPE: DNA
<213> ORGANISM: Lactobacillus phage LV-1

<400> SEQUENCE: 46
ctgattacca acaataccgt ggagatttga ttaactggta tactggcaac aagacagtaa    60
ctcaagctgc a                                                         71

<210> SEQ ID NO 47
<211> LENGTH: 71
<212> TYPE: DNA
<213> ORGANISM: Lactobacillus phage LV-1

<400> SEQUENCE: 47
tgcagcttga gttactgtct tgttgccagt ataccagtta atcaaatctc cacggtattg    60
ttggtaatca g                                                         71

<210> SEQ ID NO 48
<211> LENGTH: 111
<212> TYPE: RNA
<213> ORGANISM: Artificial
<220> FEATURE:
<223> OTHER INFORMATION: Exemplary L.jensenii CRISPR/Cas Type II single
      guide sequence

<400> SEQUENCE: 48
gauuugauua acugguauac guuuuagaag guugaaaaac cuuauuuuua aaaucaaaca    60
aggucuuagu accgaguuuu cacaugugua ccgcuuauag cggucuuuuu u            111

<210> SEQ ID NO 49
<211> LENGTH: 21
<212> TYPE: DNA
<213> ORGANISM: Lactobacillus casei

<400> SEQUENCE: 49
atgggatagg gattttttag t                                              21

<210> SEQ ID NO 50
<211> LENGTH: 89
<212> TYPE: DNA
<213> ORGANISM: Lactobacillus casei

<400> SEQUENCE: 50
gttttccccg cacatgcggg ggtgatccgg cgatgatacg tagccgaact gagaggttga    60
tgttttcccc gcacatgcgg gggtgatcc                                      89

<210> SEQ ID NO 51
<211> LENGTH: 119
<212> TYPE: DNA
<213> ORGANISM: Artificial
<220> FEATURE:
<223> OTHER INFORMATION: PCR primer sequence
```

<400> SEQUENCE: 51
caagaacagt tattgattt ataatcacta tgtgggtatg aaaatctcaa aaatcatttg        60 aggttttgt actctcaaga tttaagtaac tgtacaacat taagagattg tcttaactt       119

<210> SEQ ID NO 52
<211> LENGTH: 142
<212> TYPE: DNA
<213> ORGANISM: Artificial
<220> FEATURE:
<223> OTHER INFORMATION: PCR primer sequence

<400> SEQUENCE: 52
agcggataac aatttcacgt tttggaacca ttcgaaacaa cacagctcta aaactcagaa        60
aattcttcaa gagattcaaa atactgtttt ggaaccattc gaaacaacac agctctaaaa       120
cctcgtagga tatcttttct ac                                                142

<210> SEQ ID NO 53
<211> LENGTH: 87
<212> TYPE: DNA
<213> ORGANISM: Artificial
<220> FEATURE:
<223> OTHER INFORMATION: PCR primer sequence

<400> SEQUENCE: 53
agcggataac aatttcacgt tgtacagtta cttaaatctt gagagtacaa aaacaggga        60 gatgaagtta agacaatctc ttaatgt                                            87

<210> SEQ ID NO 54
<211> LENGTH: 142
<212> TYPE: DNA
<213> ORGANISM: Artificial
<220> FEATURE:
<223> OTHER INFORMATION: PCR primer sequence

<400> SEQUENCE: 54
agcggataac aatttcacgt tttggaacca ttcgaaacaa cacagctcta aaacgaagtc        60
ttggtcttcc aaccagcttg ctgtagtttt ggaaccattc gaaacaacac agctctaaaa       120
cctcgtagga tatcttttct ac                                                142

<210> SEQ ID NO 55
<211> LENGTH: 141
<212> TYPE: DNA
<213> ORGANISM: Artificial
<220> FEATURE:
<223> OTHER INFORMATION: PCR primer sequence

<400> SEQUENCE: 55
agcggataac aatttcacgt tttggaacca ttcgaaacaa cacagctcta aaacgataac        60
acgagataaa acatccagcc caccgttttg gaaccattcg aaacaacaca gctctaaaac       120
ctcgtaggat atcttttcta c                                                 141

<210> SEQ ID NO 56
<211> LENGTH: 141
<212> TYPE: DNA
<213> ORGANISM: Artificial
<220> FEATURE:
<223> OTHER INFORMATION: PCR primer sequence

<400> SEQUENCE: 56
agcggataac aatttcacgt tttggaacca ttcgaaacaa cacagctcta aaacgttgta    60
gctttgaggt ctgagaatac acgcgttttg gaaccattcg aaacaacaca gctctaaaac   120
ctcgtaggat atcttttcta c                                            141

<210> SEQ ID NO 57
<211> LENGTH: 141
<212> TYPE: DNA
<213> ORGANISM: Artificial
<220> FEATURE:
<223> OTHER INFORMATION: PCR primer sequence

<400> SEQUENCE: 57
agcggataac aatttcacgt tttggaacca ttcgaaacaa cacagctcta aaacgattgc    60
tcaatcaatc gtttcagctg ctaagttttg gaaccattcg aaacaacaca gctctaaaac   120
ctcgtaggat atcttttcta c                                            141

<210> SEQ ID NO 58
<211> LENGTH: 35
<212> TYPE: DNA
<213> ORGANISM: Artificial
<220> FEATURE:
<223> OTHER INFORMATION: PCR primer sequence

<400> SEQUENCE: 58
agcagggatc ctggtaataa gtatagatag tcttg                              35

<210> SEQ ID NO 59
<211> LENGTH: 21
<212> TYPE: DNA
<213> ORGANISM: Artificial
<220> FEATURE:
<223> OTHER INFORMATION: PCR primer sequence

<400> SEQUENCE: 59
ctcgtaggat atcttttcta c                                             21

<210> SEQ ID NO 60
<211> LENGTH: 37
<212> TYPE: DNA
<213> ORGANISM: Artificial
<220> FEATURE:
<223> OTHER INFORMATION: PCR primer sequence

<400> SEQUENCE: 60
agcagggatc ccaagaacag ttattgattt tataatc                            37

<210> SEQ ID NO 61
<211> LENGTH: 35
<212> TYPE: DNA
<213> ORGANISM: Artificial
<220> FEATURE:
<223> OTHER INFORMATION: PCR primer sequence

<400> SEQUENCE: 61
agcagggatc ctggtaataa gtatagatag tcttg                              35

<210> SEQ ID NO 62
<211> LENGTH: 29
<212> TYPE: DNA
<213> ORGANISM: Artificial
<220> FEATURE:
<223> OTHER INFORMATION: PCR primer sequence

```
<400> SEQUENCE: 62
tgctggagct cgtgaaattg ttatccgct                                    29

<210> SEQ ID NO 63
<211> LENGTH: 21
<212> TYPE: DNA
<213> ORGANISM: Artificial
<220> FEATURE:
<223> OTHER INFORMATION: PCR primer sequence

<400> SEQUENCE: 63
ttgaacacta ggaacctcat a                                            21

<210> SEQ ID NO 64
<211> LENGTH: 22
<212> TYPE: DNA
<213> ORGANISM: Artificial
<220> FEATURE:
<223> OTHER INFORMATION: PCR primer sequence

<400> SEQUENCE: 64
cgtaaggttt tgatgactca ag                                           22

<210> SEQ ID NO 65
<211> LENGTH: 23
<212> TYPE: DNA
<213> ORGANISM: Artificial
<220> FEATURE:
<223> OTHER INFORMATION: PCR primer sequence

<400> SEQUENCE: 65
ttggttgata atgaactgtg ctg                                          23

<210> SEQ ID NO 66
<211> LENGTH: 26
<212> TYPE: DNA
<213> ORGANISM: Artificial
<220> FEATURE:
<223> OTHER INFORMATION: PCR primer sequence

<400> SEQUENCE: 66
ttgttgtttt tatgattaca aagtga                                       26
```